(12) United States Patent
Hoelscher et al.

(10) Patent No.: US 12,083,350 B2
(45) Date of Patent: *Sep. 10, 2024

(54) ACCESSORY-BASED STORAGE FOR USE WITH A MEDICAL DEVICE

(71) Applicant: ZOLL Medical Corporation, Chelmsford, MA (US)

(72) Inventors: Jochen H. Hoelscher, Schwabmuenchen (DE); Paolo Giacometti, North Grafton, MA (US); Mohamed Abdelaziz, Nashua, NH (US); Annemarie E. Silver, Bedford, MA (US); Gary A. Freeman, Waltham, MA (US)

(73) Assignee: ZOLL Medical Corporation, Chelmsford, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/330,820

(22) Filed: Jun. 7, 2023

(65) Prior Publication Data
US 2023/0390568 A1 Dec. 7, 2023

Related U.S. Application Data

(63) Continuation of application No. 17/098,676, filed on Nov. 16, 2020, now Pat. No. 11,712,574.
(Continued)

(51) Int. Cl.
*A61N 1/39* (2006.01)
*A61H 31/00* (2006.01)
*A61N 1/04* (2006.01)

(52) U.S. Cl.
CPC ....... *A61N 1/39044* (2017.08); *A61H 31/005* (2013.01); *A61N 1/046* (2013.01);
(Continued)

(58) Field of Classification Search
CPC .......................... A61N 1/39044; A61N 1/3925
See application file for complete search history.

(56) References Cited

U.S. PATENT DOCUMENTS 6,360,120 B1 * 3/2002 Powers ................ A61N 1/3925
600/510
6,366,809 B1 * 4/2002 Olson .................. A61N 1/3975
607/29
(Continued)

*Primary Examiner* — Eric D. Bertram
(74) *Attorney, Agent, or Firm* — Finch & Maloney PLLC

(57) ABSTRACT

A patient-coupled resuscitation device for use with a plurality of medical devices is provided. The resuscitation device includes a portion configured to provide treatment, a connector configured to connect the resuscitation device to one of a first medical device and a second medical device, and a housing including a memory and associated circuitry. The memory and associated circuitry is configured to store a device identifier to identify the resuscitation device; receive medical treatment information from the first medical device, the medical treatment information including at least one of: patient physiological data, patient characteristic data, and rescuer performance data; receive timing information of the medical treatment information from the first medical device; record the medical treatment information and the timing information; and transfer, upon detecting a connection to the second medical device, the medical treatment information and the timing information to the second medical device.

23 Claims, 33 Drawing Sheets

Related U.S. Application Data

(60) Provisional application No. 62/935,849, filed on Nov. 15, 2019.

(52) U.S. Cl.
CPC ......... *A61N 1/3925* (2013.01); *A61N 1/3975* (2013.01); *A61N 1/3987* (2013.01); *A61N 1/3993* (2013.01)

(56) References Cited

U.S. PATENT DOCUMENTS

| | | | |
|---|---|---|---|
| 7,016,726 B1* | 3/2006 | Picardo | A61N 1/048 607/63 |
| 8,676,311 B2* | 3/2014 | Cordaro | A61N 1/025 607/5 |
| 9,511,239 B2* | 12/2016 | Prew | A61N 1/3937 |
| 9,844,658 B2* | 12/2017 | Jensen | A61N 1/0492 |
| 10,702,701 B1* | 7/2020 | Bielstein | A61N 1/3987 |
| 11,712,574 B2* | 8/2023 | Hoelscher | A61B 5/346 607/5 |
| 2004/0162586 A1* | 8/2004 | Covey | A61N 1/0472 607/5 |
| 2013/0304143 A1* | 11/2013 | Banville | A61N 1/3993 607/60 |
| 2015/0094782 A1* | 4/2015 | Prew | A61N 1/046 607/142 |
| 2017/0266399 A1 | 9/2017 | Campana et al. | |
| 2018/0200142 A1* | 7/2018 | Freeman | A61H 31/007 |
| 2020/0360706 A1* | 11/2020 | Bielstein | A61N 1/36146 |
| 2021/0146146 A1* | 5/2021 | Hoelscher | A61N 1/3993 |
| 2021/0220660 A1* | 7/2021 | Danziger | A61N 1/3987 |
| 2021/0236804 A1* | 8/2021 | Jensen | A61N 1/0492 |

* cited by examiner

740

742 Establish Connection

744 Monitor Connection

746 Information Request? — NO (loop back to Monitor Connection)

YES

748 Determine Requested Information

750 Access Requested Information

752 Transfer Requested Information

FIG. 7C

Electrode Information Data Structure 800

| Data Identifier Fields 805 | Data Fields 1010 |
|---|---|
| Patient ID | ID Number |
| Pre-Treatment HR | 165bpm |
| Pre-Treatment Blood Pressure | 135/100 |
| Treatable Arrhythmia? | Yes |
| Treatment Shock Provided? | Yes |
| Number of Treatment Shocks | 2 |
| 1st Treatment Shock Info | Energy: 120J   Success: No |
| 2nd Treatment Shock Info | Energy: 150J   Success: Yes |
| Post-Treatment HR | 85bpm |
| Post-Treatment Blood Pressure | 125/90 |

FIG. 8A

| Chest Compression Information Data Structure 820 | |
|---|---|
| Data Identifier Fields 825 | Data Fields 830 |
| Patient ID | ID Number |
| CPR Administered? | Yes |
| Average Compression Rate | 106 Compressions/Minute |
| Average Compression Depth | 2.2 inches |
| Maximum Compression Depth | 2.5 inches |
| Minimum Compression Depth | 1.7 inches |
| Chest Compression Fraction | 76% |
| Percentage Within Target | 65% |
| Average Release Velocity | 315 mm/sec |
| Average Pre-Shock / Post-Shock Pause | 9.5 seconds / 30 seconds |

FIG. 8B

Airflow Sensor Information Data Structure 840

| Data Identifier Fields 845 | Data Fields 850 |
|---|---|
| Patient ID | ID Number |
| Breathing Assistance Administered | Yes |
| Pre-treatment Respiration Rate | 0 breaths/minute |
| Post-treatment Respiration Rate | 18 breaths/minute |
| Pre-Treatment End-Tidal CO2 | 0 mmHg |
| Post-Treatment End-Tidal CO2 | 40 mmHg |
| Average Tidal Volume | 500 mL |
| Average Minute Volume | 6.5 L |
| Average Ventilations Within Target | 11 ventilations |
| Device ID | IDX-001122 |

FIG. 8C

Battery Information Data Structure 860

| Data Identifier Fields 865 | Data Fields 870 |
|---|---|
| Battery ID | Serial Number |
| Energy Level | 81% |
| Self-Test Information | Complete: Yes  Errors: 0 |
| Last Alarm | 09:17 July 11, 2018 |
| Alarm Type | Battery Low |
| Shocks Delivered (Lifetime) | 8 |
| Shocks Delivered (Since Charged) | 0 |
| Device ID(s) | IDX-001122; IDX-001123 |

Transfer Recorded Data

910

Patient Name: [John Doe]

915

( Transfer All Data )

Patient ID: [XX-XXX-XXXX]

---

Available Patient Data ← 920

Please select one or more of:

○ Patient Physiological Data  ← 920a

---

○ Rescuer Performance Data  ← 920b

---

○ Treatment Data  ← 920c

---

● Device Operational Data  ← 920d

Output Format:
● PDF  ← 925
○ Text Document
○ Spreadsheet

930

( Submit )  ( Clear )  ( Cancel )

Top-Down View

Side View

ACCESSORY-BASED STORAGE FOR USE WITH A MEDICAL DEVICE

RELATED APPLICATION

This application is a continuation of U.S. patent application Ser. No. 17/098,676 (filed 16 Nov. 2020), now U.S. Pat. No. 11,712,574, which claims the benefit of U.S. Provisional Patent Application 62/935,849 (filed 15 Nov. 2019). All subject matter set forth in each of the above-referenced applications is hereby incorporated by reference in its entirety into the present application as if fully set forth herein.

BACKGROUND

Treatment of a subject experiencing cardiac distress can generally include one or more of clearing the subject's airway, assisting the subject's breathing, providing chest compressions, and providing defibrillation or other similar treatment shocks. The treatment can be provided using one or more medical devices and medical device accessories such as a patient-coupled resuscitation device.

Assisting the subject's breathing can be performed using, for example, a ventilator including a manual ventilation device such as a bag-valve mask or an automatic ventilation device. The ventilator can include one or more sensors to detect, for example, air flow rate into the subject's lungs. Providing chest compressions can be performed using a chest compression sensor configured to measure, for example, chest compression rate and depth of compression information. Defibrillation can be performed with the use of an automatic external defibrillator (AED) Several commercially available automatic external defibrillators are semi-automatic external defibrillators (SAED), which require a responder to press a button to initiate a defibrillation shock. After the defibrillator analyzes the subject's condition and determines that the subject's electrical heart rhythm is shockable, the defibrillator provides an indication that the rhythm is shockable yet refrains from providing a shock until the user intervenes (e.g., presses shock button). Fully automatic external defibrillators, on the other hand, do not wait for user intervention before applying shocks. As the term is used herein, automatic external defibrillators (AED) include semi-automatic external defibrillators (SAED). A defibrillator may have monitoring capabilities, and so can include one or more sensors configured to measure various physiological data for the patient as well as information related to any treatment shocks delivered to the patient. Each medical device and/or accessory associated with treatment of a subject can be configured to record information collected during treatment for later analysis, the information including specifics on what treatment the subject received and/or performance data about any medical personnel providing the treatment.

SUMMARY

In an example, a patient-coupled resuscitation device for use with a plurality of medical devices is provided. The patient-coupled resuscitation device includes a patient-coupled portion configured to provide resuscitative treatment to the patient, a connector configured to electrically connect the patient-coupled resuscitation device to at least one of a first medical device and a second medical device, and a housing including a non-volatile memory and associated circuitry. The non-volatile memory and associated circuitry is configured to store a device identifier readable by the first medical device and the second medical device to identify the patient-coupled resuscitation device; receive medical treatment information from the first medical device via the connector, the medical treatment information including at least one of: patient physiological data, patient characteristic data, and rescuer performance data; receive timing information of the medical treatment information from the first medical device via the connector; record the medical treatment information and the timing information; and transfer, upon detecting an electrical connection to the second medical device, the medical treatment information and the timing information to the second medical device.

Implementations of the patient-coupled resuscitation device for use with a plurality of medical devices can include one or more of the following features.

In examples of the patient-coupled resuscitation device, the medical treatment information can be recorded by the first medical device during monitoring of a patient prior to and/or during treatment of the patient.

In some examples of the patient-coupled resuscitation device, the patient-coupled resuscitation device can include a sensor configured to acquire at least a portion of the medical treatment information.

In examples of the patient-coupled resuscitation device, the device identifier can include type and serial information for at least one of the first medical device and the second medical device to record.

In examples of the patient-coupled resuscitation device, the device identifier can provide for authentication with at least one of the first medical device and the second medical device for secure transfer of the medical treatment information.

In examples of the patient-coupled resuscitation device, the timing information of the medical treatment information can include a time at which the medical treatment information was recorded by the first medical device. In some examples, the resuscitation device can include timing circuitry operable to independently track time elapsed since the time at which the medical treatment information was recorded by the first medical device. In some examples, the timing circuitry can include a power source and at least one of: a real-time clock and a counter.

In examples of the patient-coupled resuscitation device, the timing information of the medical treatment information can provide a basis for time alignment between the first medical device and the second medical device.

In examples of the patient-coupled resuscitation device, the non-volatile memory and associated circuitry can be configured to record the medical treatment information and the timing information from the first medical device before the transfer of the medical treatment information and the timing information to the second medical device. In some examples, the non-volatile memory and associated circuitry can be configured to record the medical treatment information and the timing information from the first medical device when the connector is engaged with the first medical device, and transfer of the medical treatment information and the timing information to the second medical device when the connector is engaged with the second medical device.

In examples of the patient-coupled resuscitation device, the timing information can include at least one of: a time at which the connector is engaged with the first medical device and a time at which the connector is engaged with the second medical device.

In examples of the patient-coupled resuscitation device, the medical treatment information can further include summary information recording critical patient events requiring treatment, shock information for any delivered shocks, pacing summary data, and indications of alarm events.

In some examples of the patient-coupled resuscitation device, the patient-coupled resuscitation device can include an electrode configured to be operably coupled with the first medical device via the connector during a first treatment event and to record at least one parameter associated with a treatment course delivered to the patient during the first treatment event to the non-volatile memory. In some examples, the electrode can be further configured to be decoupled from the first medical device and operably coupled to the second medical device via the connector such that the medical treatment information stored on the non-volatile memory is accessible to the second medical device. In some examples, the electrode can include a defibrillation electrode, the first medical device can include a first defibrillator and/or a first patient monitor and the second medical device can include a second defibrillator and/or a second patient monitor. In some examples, the patient physiological data can include electrocardiogram (ECG) data for the patient acquired prior to treatment, during treatment, and/or after treatment. In some examples, the ECG data can include ECG data associated with at least one of a treatable cardiac rhythm and a non-treatable cardiac rhythm.

In some examples of the patient-coupled resuscitation device, the patient-coupled resuscitation device can include a flow sensor configured to be operably coupled with the first medical device via the connector during a first treatment event and to record at least one parameter associated with the first treatment event to the memory.

In examples of the patient-coupled resuscitation device, the flow sensor can be configured to be decoupled from the first medical device via the connector and operably coupled to the second medical device such that the medical treatment information stored on the memory is accessible to the second medical device. In some examples, the first medical device can include a first defibrillator and/or a first patient monitor and the second medical device can include a second defibrillator, a second patient monitor and/or a ventilator. In some examples, the physiological data can include end-tidal CO2 data for the patient acquired prior to treatment, during treatment, and/or after treatment. In some examples, the first medical device can include a defibrillator and the second medical device can include a ventilator. In some examples, the first medical device can include a ventilator and the second medical device can include a defibrillator.

In examples of the patient-coupled resuscitation device, the first medical device can include a first defibrillator and the second medical device can include a second defibrillator.

In some examples of the patient-coupled resuscitation device, the patient-coupled resuscitation device can include a chest compression device configured to monitor one or more cardiopulmonary resuscitation (CPR) parameters associated with CPR being administered to the patient, and can be further configured to record the one or more CPR parameters to the memory. In some examples, the one or more CPR parameters can include one or more of chest compression rate information, chest compression depth information, and chest compression release information. In some examples, the chest compression monitoring device can further include a strap configured to be placed about a torso of the patient to maintain the chest compression monitoring device in position. In some examples, the strap can include one or more sensors configured to measure at least one additional parameter during monitoring and treatment of the patient. In some examples, the one or more sensors can include an accelerometer configured to measure compression depth information during treatment of the patient, and wherein the at least one additional parameter includes compression depth information.

In some examples of the patient-coupled resuscitation device, the patient-coupled resuscitation device can include a battery configured to operably couple with and provide power to any medical device of the plurality of medical devices. In some examples, the medical treatment information can include device operational information including information about the battery and the medical device being powered by the battery. In some examples, the device operational information can include one or more of a number of minutes the battery has been used, a number of defibrillation treatment shocks have been delivered by the device being powered by the battery, information related to additional operational modes performed by the device being powered by the battery, and errors associated with the device being powered by the battery.

In some examples of the patient-coupled resuscitation device, the patient-coupled resuscitation device can be configured to be operably removed from a first of the plurality of medical devices and operably coupled to a second of the plurality of medical devices.

In some examples of the patient-coupled resuscitation device, the patient-coupled resuscitation device can be configured to be operably removed from a first of the plurality of medical devices and operably coupled to a computing device.

In examples of the patient-coupled resuscitation device, the non-volatile memory and associated circuitry further configured to determine whether the resuscitation device is within a proximity of a remote device, establish, in response to a determination that the resuscitation device is within the proximity, an operable connection with the remote device, and transfer at least a portion of the medical treatment information to the remote device. In some examples, the transfer of at least a portion of the medical treatment information to the remote device can occur automatically when the operable connection is established between the resuscitation device and the remote device. In some examples, the transfer of at least a portion of the medical treatment information to the remote device can occur in response to a user-provided request to transfer subsequent to establishing the operable connection between the resuscitation device and the remote device.

In examples of the patient-coupled resuscitation device, the non-volatile memory can be integrated into the connector.

In examples of the patient-coupled resuscitation device, recording the medical treatment device information to the memory can include encrypting the medical treatment information prior to recording to the memory.

In examples of the patient-coupled resuscitation device, the patient physiological data can include one or more of patient ECG data, heart rate data, ECG waveform data, end-tidal CO2 data, CO2 waveform data, pulse oximetry data, blood oxygenation data, blood pressure data, and respiratory rate data.

In examples of the patient-coupled resuscitation device, the patient characteristic data can include one or more of patient height data, patient weight data, patient gender indication, patient physical measurement data, and patient history information.

In examples of the patient-coupled resuscitation device, the rescuer performance data can include one or more of chest compression performance data, ventilation performance data, rescuer treatment information, and drug infusion information.

In examples of the patient-coupled resuscitation device, the medical treatment information can include device operational data including one or more of defibrillation shock delivery information, defibrillation shock energy information, and ventilator flow information.

In another example, a second patient-coupled resuscitation device for use with a plurality of medical devices is provided. The second patient-coupled resuscitation device includes a patient-coupled portion configured to provide resuscitative treatment to the patient and a housing including a wireless communications interface and associated circuitry and a non-volatile memory and associated circuitry. The wireless communications interface and associated circuitry is configured to detect and establish a short-range wireless connection with a first medical device and detect and establish, at a subsequent time, a short-range wireless connection with a second medical device. The non-volatile memory and associated circuitry is configured to store a device identifier readable by the first medical device and the second medical device to identify the patient-coupled resuscitation device; receive and record, upon the short-range wireless connection with the first medical device being established, medical treatment information from the first medical device, the medical treatment information including at least one of patient physiological data, patient characteristic data, and rescuer performance data; and transfer, upon detecting the short-range wireless connection with the second medical device, the medical treatment information to the second medical device.

Implementations of the second patient-coupled resuscitation device for use with a plurality of medical devices can include one or more of the following features.

In examples of the second patient-coupled resuscitation device, the short-range wireless connection with the first medical device or the second medical device can include a wireless protocol involving at least one of Bluetooth, Zigbee, near field communication, ultra-wideband, and infrared.

In examples of the second patient-coupled resuscitation device, the medical treatment information can be recorded by the first medical device during monitoring of a patient prior to and/or during treatment of the patient.

In examples of examples of the second patient-coupled resuscitation device, the second patient-coupled resuscitation device can further include a sensor configured to acquire at least a portion of the medical treatment information.

In examples of the second patient-coupled resuscitation device, the device identifier can include type and serial information for at least one of the first medical device and the second medical device to record.

In examples of the second patient-coupled resuscitation device, the device identifier can provide for authentication with at least one of the first medical device and the second medical device for secure transfer of the medical treatment information.

In examples of the second patient-coupled resuscitation device, the non-volatile memory and associated circuitry can be configured to receive timing information of the medical treatment information from the first medical device via the wireless communications interface. In some examples, the timing information of the medical treatment information can include a time at which the medical treatment information was recorded by the first medical device. In some examples, the second patient-coupled resuscitation device can include timing circuitry operable to independently track time elapsed since the time at which the medical treatment information was recorded by the first medical device. In some examples, the timing circuitry can include a power source and at least one of: a real-time clock and a counter. In some examples, the timing information of the medical treatment information can provide a basis for time alignment between the first medical device and the second medical device. In some examples, the timing information can include at least one of: a time at which the short-range wireless connection is established with the first medical device and a time at which the short-range wireless connection is established with the second medical device.

In examples of the second patient-coupled resuscitation device, the non-volatile memory and associated circuitry can be configured to record the medical treatment information from the first medical device before the transfer of the medical treatment information to the second medical device. In some examples, the non-volatile memory and associated circuitry can be configured to record the medical treatment information from the first medical device when the short-range wireless connection is established with the first medical device, and transfer of the medical treatment information to the second medical device when the short-range wireless connection is established with the second medical device.

In examples of the second patient-coupled resuscitation device, the medical treatment information can further include summary information recording critical patient events requiring treatment, shock information for any delivered shocks, pacing summary data, and indications of alarm events.

In some examples of the second patient-coupled resuscitation device, the second patient-coupled resuscitation device can include an electrode configured to be operably coupled with the first medical device during a first treatment event and to record at least one parameter associated with a treatment course delivered to the patient during the first treatment event to the non-volatile memory. In some examples, the electrode can be further configured to be decoupled from the first medical device and operably coupled to the second medical device such that the medical treatment information stored on the non-volatile memory is accessible to the second medical device. In some examples, the electrode can include a defibrillation electrode, the first medical device can include a first defibrillator and/or a first patient monitor and the second medical device can include a second defibrillator and/or a second patient monitor. In some examples, the patient physiological data can include ECG data for the patient acquired prior to treatment, during treatment, and/or after treatment. In some examples, the ECG data can include ECG data associated with at least one of a treatable cardiac rhythm and a non-treatable cardiac rhythm.

In some examples of the second patient-coupled resuscitation device, the second patient-coupled resuscitation device can include a flow sensor configured to be operably coupled with the first medical device during a first treatment event and to record at least one parameter associated with the first treatment event to the memory. In some examples, the physiological data can include end-tidal CO2 data for the patient acquired prior to treatment, during treatment, and/or after treatment. In some examples, the flow sensor can be configured to be decoupled from the first medical device and operably coupled to the second medical device such that the medical treatment information stored on the memory is accessible to the second medical device. In some examples, the first medical device can include a first defibrillator a first patient monitor and/or a first ventilator, and the second medical device can include a second defibrillator, a second patient monitor and/or a second ventilator. In some examples, the first medical device can include a defibrillator and the second medical device can include a ventilator. In some examples, the first medical device can include a ventilator and the second medical device can include a defibrillator.

In examples of the second patient-coupled resuscitation device, the first medical device can include a first defibrillator and the second medical device can include a second defibrillator.

In some examples of the second patient-coupled resuscitation device, the second patient-coupled resuscitation device can include a chest compression device configured to monitor one or more cardiopulmonary resuscitation (CPR) parameters associated with CPR being administered to the patient, and further configured to record the one or more CPR parameters to the memory. In some examples, the one or more CPR parameters can include one or more of chest compression rate information, chest compression depth information, and chest compression release information. In some examples, the chest compression device can further include a strap configured to be placed about a torso of the patient to maintain the chest compression device in position. In some examples, the strap can include one or more sensors configured to measure at least one additional parameter during monitoring and treatment of the patient. In some examples, the one or more sensors can include an accelerometer configured to measure compression depth information during treatment of the patient, and wherein the at least one additional parameter includes compression depth information.

In some examples of the second patient-coupled resuscitation device, the second patient-coupled resuscitation device can include a battery configured to operably couple with and provide power to any medical device of the plurality of medical devices. In some examples, the medical treatment information can include device operational information including information about the battery and the medical device being powered by the battery. In some examples, the device operational information can include one or more of a number of minutes the battery has been used, a number of defibrillation treatment shocks have been delivered by the device being powered by the battery, information related to additional operational modes performed by the device being powered by the battery, and errors associated with the device being powered by the battery.

In some examples of the second patient-coupled resuscitation device, the second patient-coupled resuscitation device can be further configured to be operably removed from a first of the plurality of medical devices and operably coupled to a second of the plurality of medical devices.

In some examples of the second patient-coupled resuscitation device, the second patient-coupled resuscitation device can be further configured to be operably removed from a first of the plurality of medical devices and operably coupled to a computing device.

In examples of the second patient-coupled resuscitation device, the non-volatile memory and associated circuitry can be further configured to determine whether the resuscitation device is within a proximity of a remote device, establish, in response to a determination that the resuscitation device is within the proximity, an operable connection with the remote device, and transfer at least a portion of the medical treatment information to the remote device. In some examples, the transfer of at least a portion of the medical treatment information to the remote device can occur automatically when the operable connection is established between the resuscitation device and the remote device. In some examples, the transfer of at least a portion of the medical treatment information to the remote device can occur in response to a user-provided request to transfer subsequent to establishing the operable connection between the resuscitation device and the remote device.

In examples of the second patient-coupled resuscitation device, recording the medical treatment device information to the memory can include encrypting the medical treatment information prior to recording to the memory.

In examples of the second patient-coupled resuscitation device, the patient physiological data can include one or more of patient ECG data, heart rate data, ECG waveform data, end-tidal CO2 data, CO2 waveform data, pulse oximetry data, blood oxygenation data, blood pressure data, and respiratory rate data.

In examples of the second patient-coupled resuscitation device, the patient characteristic data can include one or more of patient height data, patient weight data, patient gender indication, patient physical measurement data, and patient history information.

In examples of the second patient-coupled resuscitation device, the rescuer performance data can include one or more of chest compression performance data, ventilation performance data, rescuer treatment information, and drug infusion information.

In examples of the second patient-coupled resuscitation device, the medical treatment information can include device operational data including one or more of defibrillation shock delivery information, defibrillation shock energy information, and ventilator flow information.

In examples of the second patient-coupled resuscitation device, the wireless communications interface and associated circuitry can be configured to establish the short-range wireless connections with the first medical device and the second device successively.

In examples of the second patient-coupled resuscitation device, the wireless communications interface and associated circuitry can be configured to establish the short-range wireless connections with the first medical device and the second device simultaneously.

In another example, a medical treatment device for managing medical treatment information is provided. The medical treatment device includes at least one sensor configured to obtain medical data, a battery including a non-volatile memory and associated circuitry configured to store medical device information, a receptacle to which the battery is removably coupled and configured to draw power from the battery, and at least one processor coupled to the at least one sensor and the battery. The at least one processor is configured to receive the medical data from the at least one sensor, process the medical data to generate medical treatment information, the medical treatment information including at least one of: patient physiological data, patient characteristic data, and rescuer performance data, and record the medical treatment information to the non-volatile memory of the battery.

Implementations of the medical treatment device for managing medical treatment information can include one or more of the following features.

In examples of the medical treatment device, the medical treatment device information can further include device operational information. In some examples, the device operational information can include one or more of a number of minutes the battery has been used, a number of treatment shocks have been delivered by the medical treatment device when powered by the battery, information related to additional operational modes performed by the medical treatment device when powered by the battery, and errors associated with the medical treatment device when powered by the battery.

In examples of the medical treatment device, the at least one sensor can include a defibrillation electrode configured to be operably coupled with the monitor during a first treatment event and to record at least one parameter associated with the first treatment event. In some examples, the patient physiological data can include ECG data for the patient acquired prior to treatment, during treatment, and/or after treatment. In some examples, the ECG data can include ECG data associated with at least one of a treatable cardiac rhythm and a non-treatable cardiac rhythm.

In examples of the medical treatment device, the at least one sensor can include a chest compression monitoring device configured to monitor one or more CPR parameters associated with CPR being administered to the patient. In some examples, the at least one processor can be further configured to record the one or more CPR parameters to the memory. In some examples, the one or more CPR parameters can include at least one of chest compression rate information, chest compression depth information, and chest compression release information.

In examples of the medical treatment device, the memory can be configured to be operably removed from the battery and operably coupled to a second device.

In examples of the medical treatment device, the at least one processor can be further configured to determine if the medical treatment device is within a proximity of a remote device, establish an operable connection with the remote device, and transfer at least a portion of the medical treatment device information from the memory to the remote device. In some examples, the transfer of at least a portion of the medical treatment device information to the remote device can occur automatically when the operable connection is established between the medical treatment device and the remote device. In some examples, the transfer of at least a portion of the medical treatment device information to the remote device can occur in response to a user-provided request to transfer when the operable connection is established between the medical treatment device and the remote device.

In examples of the medical treatment device, the memory can be integrated into a connector of the battery.

In another example, a standalone chest compression device for use with a plurality of medical treatment devices is provided. The chest compression device includes a housing, a non-volatile memory and associated circuitry disposed in the housing, at least one motion sensor configured to detect chest motion information during performance of chest compressions by a rescuer, a communication circuit disposed in the housing and configured to establish a communicative connection with a medical device, and at least one processor disposed in the housing and operably coupled to the non-volatile memory, the at least one motion sensor, and the communication circuit. The at least one processor is configured to receive the chest motion information from the at least one motion sensor; establish the communicative connection with the medical device; receive medical treatment information from the medical device, the medical treatment information including at least one of: patient physiological data, patient characteristic data and rescuer performance data; record the chest motion information and the medical treatment information to the non-volatile memory; and transfer the chest motion information to the medical device.

Implementations of the standalone chest compression device for use with a plurality of medical treatment devices can include one or more of the following features.

In examples of the standalone chest compression device, the at least one processor can be configured to receive the medical treatment information from the medical device via the communicative connection.

In some examples of the standalone chest compression device, the standalone chest compression device can include at least one computing device configured to store the medical treatment information, and the at least one processor can be configured to establish a communicative connection with the at least one computing device to receive and record the medical treatment information to the memory. In some examples, the at least one computing device can include a user interface for inputting the medical treatment information.

In some examples of the standalone chest compression device, the standalone chest compression device can include a connector coupled with the communication circuit and for mechanical coupling and decoupling with the medical device, and for establishing the communicative connection with the medical device.

In some examples of the standalone chest compression device, the standalone chest compression device can include a wireless communications interface and associated circuitry coupled with the communication circuit and configured to detect and establish a short-range wireless connection with the medical device. In some examples, the short-range wireless connection with the medical device can include a wireless protocol involving at least one of: Bluetooth, Zigbee, near field communication, ultra-wideband, and infrared.

In examples of the standalone chest compression device, the at least one processor can be configured to generate one or more CPR parameters based on the chest motion information. In some examples, the at least one processor is configured to compare the one or more CPR parameters with desired target parameters to generate a comparison and provide an indication of CPR quality based on the comparison. In some examples, the standalone chest compression device can include a feedback device configured to provide an indication of the one or more CPR parameters. In some examples, the standalone chest compression device can include a feedback device configured to provide an indication of the comparison between the one or more CPR parameters and the desired target parameters. In some examples, the one or more CPR parameters can include at least one of chest compression rate information, chest compression depth information, and chest compression release information.

In examples of the standalone chest compression device, the at least one processor can be provided within space enclosed by the housing.

In examples of the standalone chest compression device, the at least one processor can be provided with the medical device.

In some examples of the standalone chest compression device, the standalone chest compression device can further include a strap configured to be placed about a torso of the patient to hold the chest compression device in position. In some examples, the strap can include one or more second sensors configured to measure at least one additional parameter during monitoring and treatment of the patient. In some examples, the one or more second sensors can include a strain gauge configured to measure expansion and contraction of the patient's torso during monitoring and treatment of the patient, and wherein the at least one additional parameter includes chest expansion and contraction information. In some examples, the at least one processor can be further configured to record the chest expansion and contraction information to the memory. In some examples, the at least one processor can be further configured to determine respiration information for the patient based upon the chest expansion and contraction information and record the respiration information to the memory. In some examples, the strain gauge can include a potentiometer configured to measure changes in a length of at least a portion of the strap when positioned about the torso of the patient. In some examples, the strap can include an adjustable connector to alter a length of the strap to position the one or more second sensors on an opposite side of the patient from the at least one sensor. In some examples, the adjustable connector can include at least one of a buckle, an elastic portion, an adjustable hook-and-loop fastener, a slidable connector, a snap connector, and a ratcheting connector. In some examples, the strap can include a receptacle configure to receive at least a portion of the chest compression device to secure the chest compression device against the torso of the patient.

In some examples of the standalone chest compression device, the standalone chest compression device can be configured to be activated upon removal from a package.

In some examples of the standalone chest compression device, the standalone chest compression device can be configured to be activated in response to a force being exerted on at least a portion of the chest compression device.

In some examples of the standalone chest compression device, the standalone chest compression device can be configured to be activated in response to a user-actuation of at least a portion of the chest compression device.

In some examples of the standalone chest compression device, the standalone chest compression device can be configured to be activated in response to being moved into proximity of a defibrillation device.

In examples of the standalone chest compression device, the patient characteristic data can include one or more of patient height data, patient weight data, patient gender indication, and patient physical measurement data. In some examples, the at least one processor can be further configured to determine target compression and/or ventilation parameters based upon the patient characteristic data. In some examples, the at least one processor is configured to compare one or more CPR parameters with the target compression and/or ventilation parameters to generate a comparison and provide an indication of CPR quality based on the comparison.

In another example, a defibrillation electrode for use with a plurality of defibrillation devices is provided. The defibrillation electrode includes a connector configured to operably couple the defibrillation electrode to at least one of a first defibrillation device and a second defibrillation device, a skin contacting portion configured to contact skin of a patient, and a housing including non-volatile memory and associated circuitry. The non-volatile memory and associated circuitry are configured to store a device identifier readable by the first defibrillation device and the second defibrillation device to identify the defibrillation electrode; receive medical treatment information from the first defibrillation device via the connector, the medical treatment information including at least one of: patient physiological data, patient characteristic data, and rescuer performance data; record the medical treatment information; and transfer, upon detecting an electrical connection to the second defibrillation device, the medical treatment information to the second defibrillation device.

Implementation of the defibrillation electrode for use with a plurality of defibrillation devices can include one or more of the following features.

In examples of the defibrillation electrode, the medical treatment information can be recorded by the first defibrillation device during monitoring of a patient prior to and/or during treatment of the patient.

In examples of the defibrillation electrode, the device identifier can include type and serial information for at least one of the first defibrillation device and the second defibrillation device to record.

In examples of the defibrillation electrode, the device identifier can provide for authentication with at least one of the first defibrillation device and the second defibrillation device for secure transfer of the medical treatment information.

In examples of the defibrillation electrode, the non-volatile memory and associated circuitry can be configured to receive timing information of the medical treatment information from the first defibrillation device via the connector. In some examples, the timing information of the medical treatment information can include a time at which the medical treatment information was recorded by the first defibrillation device. In some examples, the defibrillation electrode can further include timing circuitry operable to independently track time elapsed since the time at which the medical treatment information was recorded by the first defibrillation device.

In examples of the defibrillation electrode, the non-volatile memory and associated circuitry can be configured to record the medical treatment information from the first defibrillation device before the transfer of the medical treatment information to the second defibrillation device. In some examples, the non-volatile memory and associated circuitry can be configured to record the medical treatment information from the first defibrillation device when the connector is engaged with the first defibrillation device, and transfer of the medical treatment information to the second defibrillation device when the connector is engaged with the second defibrillation device.

In examples of the defibrillation electrode, the medical treatment information can further include summary information recording critical patient events requiring treatment, shock information for any delivered shocks, pacing summary data, and indications of alarm events.

In some examples of the defibrillation electrode, the defibrillation electrode can be configured to be operably removed from a first of the plurality of defibrillation devices and operably coupled to a computing device.

In examples of the defibrillation electrode, the non-volatile memory and associated circuitry can be further configured to determine whether the defibrillation electrode is within a proximity of a remote device, establish, in response to a determination that the defibrillation electrode is within the proximity, an operable connection with the remote device, and transfer at least a portion of the medical treatment information to the remote device. In some examples, the transfer of at least a portion of the medical treatment information to the remote device can occur automatically when the operable connection is established between the defibrillation electrode and the remote device. In some examples, the transfer of at least a portion of the medical treatment information to the remote device can occur in response to a user-provided request to transfer subsequent to establishing the operable connection between the defibrillation electrode and the remote device.

In examples of the defibrillation electrode, recording the medical treatment device information to the memory can include encrypting the medical treatment information prior to recording to the memory.

In examples of the defibrillation electrode, the patient physiological data can include one or more of patient ECG data, heart rate data, ECG waveform data, end-tidal $CO_2$ data, $CO_2$ waveform data, pulse oximetry data, blood oxygenation data, blood pressure data, and respiratory rate data.

In examples of the defibrillation electrode, the patient characteristic data can include one or more of patient height data, patient weight data, patient gender indication, patient physical measurement data, and patient history information.

In examples of the defibrillation electrode, the rescuer performance data can include one or more of chest compression performance data, ventilation performance data, rescuer treatment information, and drug infusion information.

In examples of the defibrillation electrode, the medical treatment information can include device operational data including one or more of defibrillation shock delivery information, defibrillation shock energy information, and ventilator flow information.

In examples of the defibrillation electrode, the connector can be configured to be operably coupled to the defibrillation device during a first treatment event and the at least one of a processor operably coupled to the memory and software is further configured to record at least one parameter associated with the first treatment event to the memory. In some examples, the connector can be further configured to be decoupled from the defibrillation device and operably coupled to a second defibrillation device such that the medical treatment information stored on the memory is accessible to the second defibrillation device.

In examples of the defibrillation electrode, the memory can be configured to be operably removed from the defibrillation electrode and operably coupled to a second defibrillation electrode.

In examples of the defibrillation electrode, the memory can be configured to be operably removed from the defibrillation electrode and operably coupled to a computing device.

In examples of the defibrillation electrode, the memory can be integrated into the connector.

In examples of the defibrillation electrode, at least a portion of the skin contacting portion can be further configured to deliver a defibrillation shock to the patient during treatment.

In another example, a system for assisting in medical treatment of a patient and for managing medical treatment information is provided. The system includes a patient-coupled resuscitation device including a non-volatile memory and associated circuitry configured to store a device identifier readable by a plurality of medical devices to identify the patient-coupled resuscitation device and record medical treatment information including at least one of: patient physiological data, patient characteristic data, and rescuer performance data; a first medical device including at least one first processor configured to receive and record the medical treatment information including at least one of: patient physiological data, patient characteristic data, and rescuer performance data, establish a first communicative connection with the patient-coupled resuscitation device, transfer the medical treatment information to the patient-coupled resuscitation device via the first communicative connection; and a second medical device including at least one second processor configured to establish a second communicative connection with the patient-coupled resuscitation device and receive and record the medical treatment information from the patient-coupled resuscitation device via the second communicative connection.

Implementations of the system for assisting in medical treatment and for managing medical treatment information can include one or more of the following features.

In examples of the system, the patient-coupled resuscitation device can include a connector configured to electrically connect the patient-coupled resuscitation device to at least one of the first medical device and the second medical device.

In examples of the system, the patient-coupled resuscitation device can include a wireless communications interface and associated circuitry configured to detect and establish a short-range wireless connection with the first medical device and detect and establish a short-range wireless connection with the second medical device.

In some examples, the wireless communications interface and associated circuitry can be configured to establish the short-range wireless connections with the first medical device and the second device successively. In some examples, the wireless communications interface and associated circuitry can be configured to establish the short-range wireless connections with the first medical device and the second device simultaneously. In some examples, the non-volatile memory and associated circuitry of the patient-coupled resuscitation device can be configured to receive timing information of the medical treatment information from the first medical device via the wireless communications interface. In some examples, the system can include timing circuitry operable to independently track time elapsed since the time at which the medical treatment information was recorded by the first medical device.

In examples of the system, the medical treatment information can be recorded by the first medical device during monitoring of a patient prior to and/or during treatment of the patient.

In examples of the system, the medical treatment information can further include summary information recording critical patient events requiring treatment, shock information for any delivered shocks, pacing summary data, and indications of alarm events.

In examples of the system, the patient-coupled resuscitation device can include an electrode configured to be operably coupled with the first medical device during a first treatment event and to record at least one parameter associated with a treatment course delivered to the patient during the first treatment event to the non-volatile memory. In some examples, the electrode can include a defibrillation electrode, the first medical device can include a first defibrillator and/or a first patient monitor and the second medical device can include a second defibrillator and/or a second patient monitor.

In examples of the system, the patient physiological data can include ECG data for the patient acquired prior to treatment, during treatment, and/or after treatment.

In examples of the system, the patient-coupled resuscitation device can include a flow sensor configured to be operably coupled with the first medical device during a first treatment event and to record at least one parameter associated with the first treatment event to the memory. In some examples, the first medical device can include a first defibrillator and/or a first patient monitor and the second medical device can include a second defibrillator, a second patient monitor and/or a ventilator.

In examples of the system, the first medical device can include a first defibrillator and the second medical device can include a second defibrillator.

In examples of the system, the patient-coupled resuscitation device can include a chest compression device configured to monitor one or more CPR parameters associated with CPR being administered to the patient, and further configured to record the one or more CPR parameters to the memory.

In examples of the system, the patient-coupled resuscitation device can include a battery configured to operably couple with and provide power to any of the first medical device and the second medical device. In some examples, the medical treatment information can include device operational information including information about the battery and the medical device being powered by the battery.

In examples of the system, the patient physiological data can include one or more of patient ECG data, heart rate data, ECG waveform data, end-tidal CO2 data, CO2 waveform data, pulse oximetry data, blood oxygenation data, blood pressure data, and respiratory rate data.

In examples of the system, the patient characteristic data can include one or more of patient height data, patient weight data, patient gender indication, patient physical measurement data, and patient hi story information.

In examples of the system, the rescuer performance data can include one or more of chest compression performance data, ventilation performance data, rescuer treatment information, and drug infusion information.

BRIEF DESCRIPTION OF THE DRAWINGS

Various aspects of at least one example are discussed below with reference to the accompanying figures, which are not intended to be drawn to scale. The figures are included to provide an illustration and a further understanding of the various aspects and examples disclosed herein and are incorporated in and constitute a part of this specification. However, the figures are not intended to limit the scope of the disclosure. The figures, together with the remainder of the specification, serve to explain principles and operations of the described and claimed aspects and examples. In the figures, each identical or nearly identical component that is illustrated in various figures is represented by a like numeral. For purposes of clarity, not every component may be labeled in every figure.

FIG. 7C is a flow diagram illustrating a process of transferring recorded information from a medical device accessory-based memory, in accordance with at least one example disclosed herein.

FIGS. 8A-8D are illustrative data structures showing data stored in a medical device accessory-based memory, in accordance with at least one example disclosed herein.

FIG. 9A is a user interface screen for controlling transfer of information from a medical device accessory-based memory, in accordance with at least one example disclosed herein.

FIG. 9B is a user interface screen for viewing information stored on a medical device accessory-based memory, in accordance with at least one example disclosed herein.

DETAILED DESCRIPTION

Figure 1:
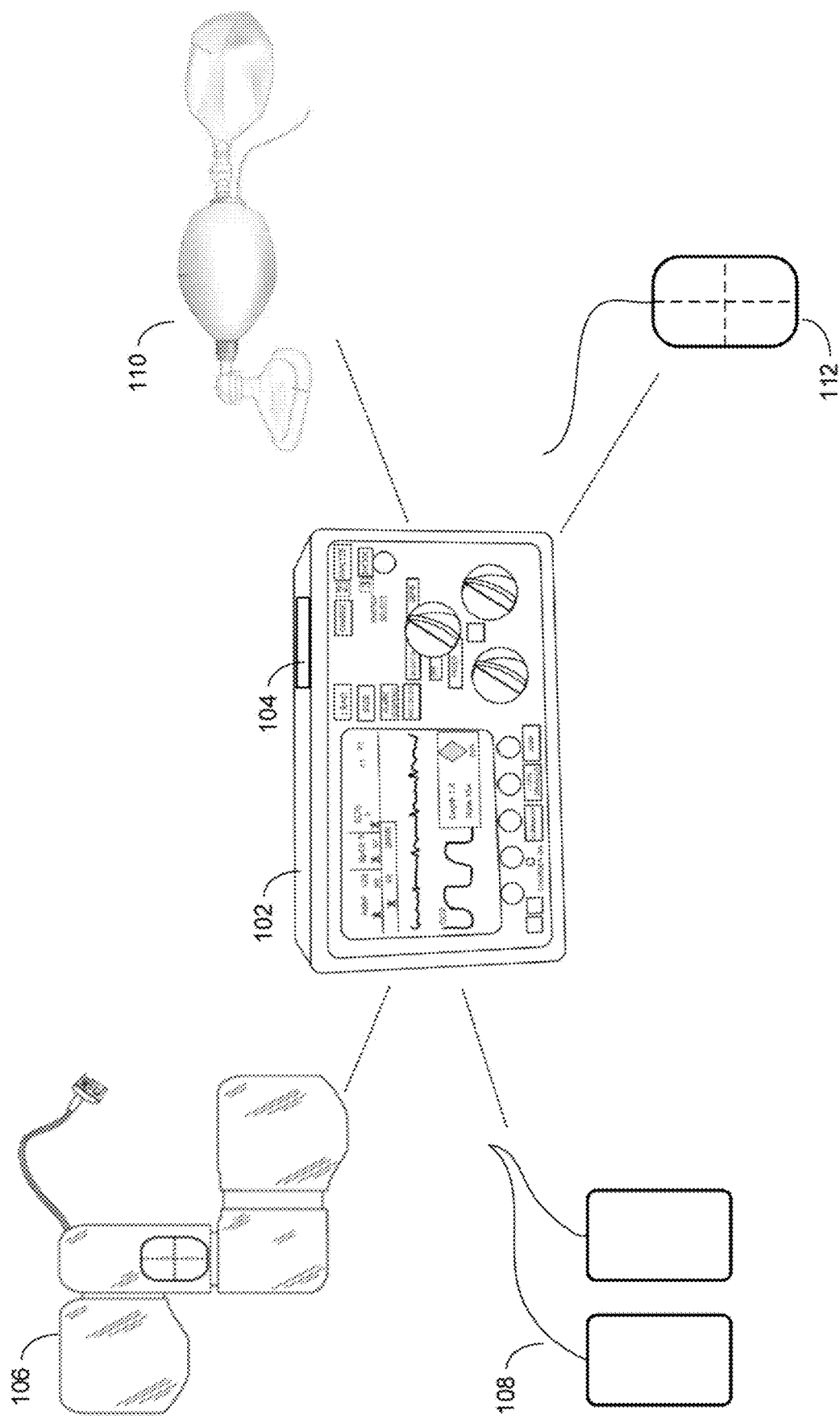
FIG. 1 is a schematic diagram showing a sample medical device and a set of medical device accessories, in accordance with at least one example disclosed herein.

Typically, when a cardiac patient experiences a cardiac event such as an arrhythmia, the quicker the patient is provided treatment the greater the chances of survival. As such, many public places are equipped with wall mounted or otherwise portable and readily available automatic external defibrillators (AEDs). A wall mounted AED may include a defibrillator device and an integrated therapy pad that includes sensing and treatment electrodes as well as a chest compression sensor. In general, the surface of the integrated therapy pads present printed instructions describing where to position the pad on the patient's body and how to begin/administer treatment to the patient.

In most instances, unless the patient experiences the cardiac event in close range to trained emergency responders, first responders to the patient will typically be bystanders such as family or friends of the patient or strangers who happen to be near the patient when the cardiac event occurred. As such, treatment of the patient is generally begun by the first responders prior to arrival of trained emergency responders using, for example, a wall mounted AED as described above.

In time, the trained emergency responders will arrive on the scene to treat the patient. The trained emergency responders will typically bring their own medical devices, such as a defibrillation device and/or an automated ventilator. Often such devices used by trained responders contain more advanced capabilities than the more basic medical device(s) (e.g. public access AEDs) more readily available to the first responder(s). Rather than using the more basic medical device(s) that are first applied to the patient, the trained emergency responders will use devices that typically have more advanced monitoring and treatment capabilities compared to the initial AED. However, rather than removing all of the equipment that has already been applied to the patient, such as electrodes and chest compression sensor, depending upon the manufacturer and compatibility, for example, the trained emergency responders may be able to simply disconnect the existing equipment on the victim from the initial AED and connect it directly to their, more familiar and possibly more advanced defibrillation device.

However, one potential problem with such an approach is that the trained emergency responders may be uninformed about specific details of the situation such as physiological information of the patient prior to arrival, timing information, what treatment information has already been provided to the patient, the patient's response to the treatment, whether the treatment was successful or not, responder actions during treatment, how well the responder performed certain actions such as chest compressions and/or ventilations, and other similar details. The time spent determining these details can further delay proper diagnosis and treatment of the patient.

Aspects of the present disclosure are designed to reduce or eliminate uncertainty on the parts of the trained emergency responders by providing, for example, memory integrated into an accessory such as a patient-coupled resuscitation device that is configured to record information about the patient prior to, during, and after treatment. In such an examples, the patient-coupled resuscitation device can act as a store of information related to the patient's care and treatment that migrates and transfers such information between devices. For instance, relevant medical information recorded by a first medical device may be stored directly on the patient-coupled resuscitation device or another similar accessory, so that when the second (more advanced) medical device arrives, the patient-coupled resuscitation device or another similar accessory having all the relevant information stored thereon may be decoupled from the first medical device and then coupled to the second medical device, so as to transfer the relevant information to the second medical device, immediately making such information readily available to the trained emergency responder. This way, the trained emergency responder no longer has to find the first medical device and retrieve the relevant medical information therefrom.

As an example, the integrated therapy pad as described above can be modified to include a non-volatile memory as described herein that is configured to record various information such as patient physiological information (e.g., ECG waveforms, $CO_2$ waveforms/information, oxygen saturation data, etc.), operational information for the AED during treatment, patient response to the treatment, patient characteristic data, rescuer performance data (e.g., CPR performance), amongst other relevant medical information. Upon disconnection of the integrated therapy pad from the initial AED and connection of the pad to the trained emergency responders' defibrillation device (which may be configured to act as a patient monitor), the information stored on the memory can be automatically transferred to the defibrillation device, thereby updating the defibrillation device with all collected and available information. The defibrillation device can then immediately continue the monitoring and/or treatment of the patient as was being performed by the initial AED.

As another use scenario, in a hospital setting, a patient may require CPR in the form of chest compressions and/or ventilations, however, the defibrillator/monitor may not always be readily available. Traditionally, chest compression feedback is provided with the defibrillator/monitor, however this system that includes the defibrillator/monitor is often later arriving, and so unfortunately, chest compressions are often provided without proper feedback. Hence, it may be desirable for there to be a mechanism for providing chest compression and/or ventilation feedback before the defibrillator/monitor arrives. Accordingly, a standalone chest compression monitoring device or sensor may be provided nearby a patient (e.g., in the room, at the bedside, on a wall or shelf, etc.), along with a bag-valve mask, so that chest compressions and/or ventilations, with feedback, may be provided to the patient, despite the absence in the moment of a defibrillator/monitor. The standalone chest compression monitoring device may have non-volatile memory that is able to record and store patient physiological data, patient characteristics data, and rescuer performance data. When a later arriving defibrillator and/or monitoring medical device arrives, the standalone chest compression monitoring device may be able to establish a communicative connection (e.g., wireless or wired) with the medical device and, hence, provide the later arriving medical device with all the relevant patient, treatment, rescuer performance, medical information that had been previously recorded. The standalone chest compression device may provide feedback for a rescuer providing manual compressions to adjust the manner in which chest compressions are given. For example, the compression device may be able to provide, on the device itself and/or on a companion interface (e.g., tablet screen, other display and/or speaker) an indication of the compression depth, rate, release velocity and/or other parameter that the rescuer is applying, and whether or not the compression parameter(s) are within desired target range(s).

Similarly the case with a bag-valve mask (BVM) with flow sensing capabilities, which may be provided with non-volatile memory that is able to record and store patient physiological data, patient characteristics data, and rescuer performance data. When the later arriving defibrillator and/or monitoring medical device arrives, the flow sensor device may be able to establish a communicative connection (e.g., wireless or wired) with the medical device and provide the later arriving medical device with all the relevant patient, treatment, rescuer performance, medical information that had been previously recorded. The BVM and/or flow sensor device may provide feedback for a rescuer providing manual ventilations to adjust the manner in which ventilations are given. For example, the flow sensing device may be able to provide, on the device itself and/or on a companion interface (e.g., tablet screen, other display and/or speaker) an indication of the tidal volume, ventilation rate, minute volume and/or other parameter that the rescuer is applying, and whether or not the ventilation parameter(s) are within desired target range(s).

Thus, and in accordance with at least some of the examples as described herein, resuscitation accessories such as patient-coupled resuscitation devices for use with various medical devices having integrated memory for storing information about the operation of the medical devices are described. In some examples, the resuscitation accessory optionally includes a sensor configured to acquire medical information, the medical information comprising at least one of: patient physiological data, patient characteristic data, and rescuer performance data. The accessory can further include a memory and at least one processor operably coupled to the memory and the sensor. The at least one processor can be configured to receive the medical treatment device information acquired by the sensor during monitoring of a patient prior to and/or during treatment of the patient and record the medical treatment device information to the memory. In some examples, the processor is further configured to automatically transfer the medical treatment device information to another device upon connection of the accessory to the device. In some examples, the processor can be configured to respond to a request for a transfer of the medical treatment device information to another device.

In some examples, patient-coupled resuscitation devices for use with a plurality of medical devices are described. In at least one example, a patient-coupled resuscitation device can include a patient-coupled portion configured to provide resuscitative treatment to the patient, a connector configured to electrically connect the patient-coupled resuscitation device to at least one of a first medical device and a second medical device, and a housing including a non-volatile memory and associated circuitry. In some examples, the non-volatile memory and associated circuitry can be configured to store a device identifier readable by the first medical device and the second medical device to identify the patient-coupled resuscitation device, receive medical treatment information from the first medical device via the connector, the medical treatment information comprising at least one of: patient physiological data, patient characteristic data, and rescuer performance data, receive timing information of the medical treatment information from the first medical device via the connector, record the medical treatment information and the timing information, and transfer, upon detecting an electrical connection to the second medical device, the medical treatment information and the timing information to the second medical device.

In some examples, a patient-coupled resuscitation device can include a defibrillation electrode configured for use with a plurality of defibrillation devices. The electrode can include a memory, a connector configured to operably couple the defibrillation electrode to one of the plurality of defibrillation devices, a skin contacting portion configured to contact skin of a patient, and at least one processor operably coupled to the memory. The processor can be configured to determine patient physiological data based upon signals collected by the skin contacting portion during monitoring of a patient prior to and during treatment. The processor can also be configured to determine device operational data related to operation of the one of the plurality of defibrillation devices operably coupled to the defibrillation electrode prior to and during treatment. The processor can further be configured to record the patient physiological data and the device operational data to the memory.

In some examples, additional patient-coupled resuscitation devices for use with a plurality of medical devices are described. An additional patient-coupled resuscitation device can include a patient-coupled portion configured to provide resuscitative treatment to the patient and a housing including a wireless communications interface and associated circuitry and a non-volatile memory and associated circuitry. In some examples, the wireless communications interface and associated circuitry can be configured to detect and establish a short-range wireless connection with a first medical device, and detect and establish, at a subsequent time, a short-range wireless connection with a second medical device. In some examples, the non-volatile memory and associated circuitry can be configured to store a device identifier readable by the first medical device and the second medical device to identify the patient-coupled resuscitation device, receive and record, upon the short-range wireless connection with the first medical device being established, medical treatment information from the first medical device, the medical treatment information comprising at least one of patient physiological data, patient characteristic data, and rescuer performance data, and transfer, upon detecting the short-range wireless connection with the second medical device, the medical treatment information to the second medical device.

In some examples, medical treatment devices for managing medical treatment information are described. A medical treatment device can include at least one sensor configured to obtain medical data, a battery comprising a non-volatile memory and associated circuitry configured to store medical device information, a receptacle to which the battery is removably coupled and configured to draw power from the battery, and at least one processor coupled to the at least one sensor and the battery. The at least one processor can be configured to receive the medical data from the at least one sensor, process the medical data to generate medical treatment information, the medical treatment information comprising at least one of: patient physiological data, patient characteristic data, and rescuer performance data, and record the medical treatment information to the non-volatile memory of the battery.

In some examples, systems for assisting in medical treatment of a patient and for managing medical treatment information are described. An example system can include a patient-coupled resuscitation device comprising a non-volatile memory and associated circuitry configured to store a device identifier readable by a plurality of medical devices to identify the patient-coupled resuscitation device and record medical treatment information comprising at least one of patient physiological data, patient characteristic data, and rescuer performance data, and a first medical device comprising at least one first processor configured to receive and record the medical treatment information comprising at least one of: patient physiological data, patient characteristic data, and rescuer performance data, establish a first communicative connection with the patient-coupled resuscitation device, and transfer the medical treatment information to the patient-coupled resuscitation device via the first communicative connection. The example system can further include a second medical device comprising at least one second processor configured to establish a second communicative connection with the patient-coupled resuscitation device, and receive and record the medical treatment information from the patient-coupled resuscitation device via the second communicative connection.

In some situations as described herein, a medical device accessory such as a patient-coupled resuscitation device can include a chest compression sensor. However, a typical chest compression sensor can be inappropriate for use in some scenarios. For example, when treating a neo-natal patient, a typical chest compression sensor may be too big to properly be positioned on and monitor such a small patient. Additionally, with a newborn patient, the baby is typically covered in fluid that may make positioning and securing a chest compression sensor difficult. As time is a factor in saving a patient, cleaning the baby is typically unfeasible.

Aspects of the present disclosure are designed to provide a chest compression sensor that is adapted to or suitable for use with a neonatal patient. For example, as described herein, a chest compression sensor can include an elastic strap that is configured to be positioned about the patient's torso, thereby holding the chest compression sensor in proper position during treatment such as cardiopulmonary resuscitation (CPR). In some examples, the strap can include an adjustable closure such as a ratchet or buckle that provides for an adjustable fit about the torso of the patient, increasing the reliability of information collected by the chest compression sensor.

Example Medical Devices

As noted above, a medical device can be configured to record information related to treatment of the patient for later review and analysis. In some examples, the medical device can be configured to record this information onto a removable storage device such as memory integrated into a removable battery. Information related to the operation of the medical device as well as information obtained from or related to the operation of any accessories connected to or otherwise associated with the medical device can be recorded onto the memory. For example, as shown in FIG. 1, a medical device such as defibrillator 102 can include a removable battery 104 that is configured to provide power to the defibrillator as well as to record information about operation of the defibrillator as described herein.

As further shown in FIG. 1, the defibrillator 102 can be configured to operate with various resuscitation accessories. For example, the defibrillator 102 can include an electrical connector that is configured to operably couple to one or more accessories such as integrated therapy pad 106 including a combination set of electrodes/chest compression sensor, a set of standalone monitoring/treatment electrodes 108. The defibrillator can also be configured to couple to a bag-valve-mask (BVM) 110 including, for example, a ventilation bag, which is connected to a ventilation valve and a mask, as well as an integrated flow sensor. In some examples, the defibrillator 102 can be further configured to couple to a standalone chest compression sensor 112 that has functionality to provide chest compression feedback without requiring the defibrillator. In certain implementations, the defibrillator 102 can be configured to couple to the chest compression sensor 112 via a wired or wireless connection.

Depending upon which patient-coupled resuscitation device or accessory is coupled to the defibrillator 102, the defibrillator can be configured to perform one or more operations and to record specific information related to the one or more operations to the removable memory included in battery 104. For example, if the integrated therapy pad 106 is coupled to the defibrillator 102, the defibrillator can receive electrical signals measured by, for example, one or more sensing electrodes integrated into the therapy pad. The defibrillator 102 can analyze the electrical signals to determine one or more physiological signals for the patient. For example, the one or more physiological signals can include heart rate metrics, RR interval metrics, heart rate variability metrics, premature ventricular complex burden or counts, atrial fibrillation burden metrics, pauses, heart rate turbulence metrics, QRS height, QRS width, changes in a size or shape of morphology of the received ECG information, cosine R-T, artificial pacing, QT interval, QT variability, T wave width, T wave alternans, T-wave variability, and/or ST segment changes. The defibrillator 102 can further analyze the one or more physiological signals to determine if the patient is experiencing a cardiac event such as an arrhythmia and determine whether to provide treatment such as one or more defibrillation shocks to the patient based upon the analysis.

Similarly, the defibrillator 102 can collect information from other accessories that are operably coupled to the defibrillator and store the information in the memory of the accessories. For example, the BVM 110 is coupled to the defibrillator 102, so the defibrillator can determine and record various information from the flow rate sensor such as respiratory rate metrics, inhaled oxygen level information, end-tidal CO2 information, and other similar metrics. In another example, the chest compression sensor 112 is coupled to the defibrillator 102, so the defibrillator can determine and record various information such as chest compression rate information, chest compression depth information, and other similar metrics.

It should be noted that a portable external defibrillator is shown in FIG. 1 by way of example. In certain implementations, a wearable cardio-defibrillator such as a WCD such as the LifeVest® Wearable Cardioverter Defibrillator from ZOLL Medical Corporation (Chelmsford, MA) can be provided as the medical device as described herein.

Figure 2:
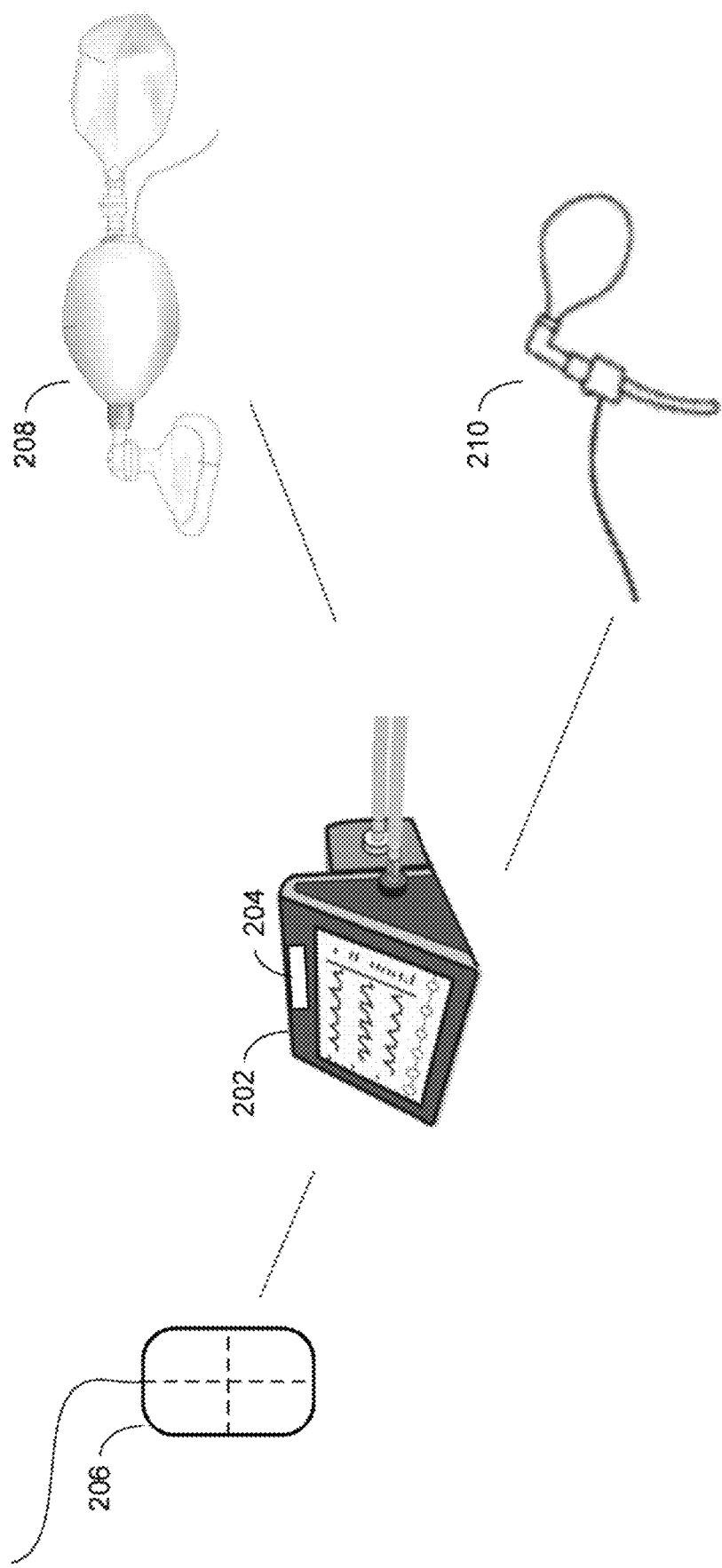
FIG. 2 is a schematic diagram showing an alternative sample medical device and a set of medical device accessories, in accordance with at least one example disclosed herein.

In another example, as shown in FIG. 2, a medical device such as ventilator 202 can include a removable battery 204 that is configured to provide power to the ventilator as well as to record information about operation of the ventilator as described herein.

As further shown in FIG. 2, the ventilator 202 can be configured to operate with various resuscitation accessories. For example, the ventilator 202 can include an electrical connector that is configured to operably couple to one or more accessories such as a chest compression sensor 206, a BVM 208 including, for example, an integrated flow sensor, and breathing assistance device 210 including an endotracheal tube for patient intubation. Depending upon which patient-coupled resuscitation device or accessory is coupled to the ventilator 202, the ventilator can be configured to perform one or more operations and to record specific information related to the operation of the removable memory included in battery 204 in this example. For example, if the chest compression sensor 206 is coupled to the ventilator 202, the ventilator can determine and record various information such as chest compression rate information, chest compression depth information, and other similar metrics. If the BVM 208 of the breathing assistance device 210 is coupled to the ventilator 202, the ventilator can determine and record various information from the flow rate sensor such as respiratory rate metrics, inhaled oxygen level information, end-tidal CO2 information (for systems that integrate CO2 sensing), ventilation tidal volume, ventilation rate, minute volume, and other similar respiration metrics.

In certain situations, treatment of a patient can transition from a first treatment device to a second treatment device. For example, a patient experiencing a cardiac event such as an arrhythmia may first be treated using a publicly available AED mounted on, for example, a wall of an airport. The person administering the initial treatment may be a passerby, a family member or friend of the patient, or another similar person with limited training in using the treatment device. After a period of time, additional people such as emergency medical responders may arrive at the scene and take over treatment of the patient. In such a situation, the emergency medical responders will likely bring more advanced medical treatment devices, such as a defibrillator/monitor with treatment capabilities or a patient monitor with monitoring functionality but absent the ability to provide treatment, and will transition treatment of the patient to those devices. In such an example, transferring any information about the patient and the treatment of the patient to the new treatment device can be advantageous. Accordingly, a patient-coupled resuscitation device and/or other accessory such as those described herein may be equipped with processing and/or memory that enables any and all relevant patient information to be recorded thereon from the first medical device, and then transferred to the second medical device. This allows for a more complete, integrated patient care record that includes device identification and/or usage information, along with the associated patient physiological and treatment information.

The more complete patient care record, including medical treatment information (e.g., patient physiological data, patient characteristics, rescuer performance data) recorded from both the first medical device and the second medical device may then be available for post-case review by other medical personnel who were not present at the scene, without having to collect the data gathered from each device separately, and then having to merge or consolidate the information together. For example, since data gathered by the first medical device is recorded onto and transferred to the second medical device or other computing device via the accessory, the post-case review personnel may be able to view what the patient's presenting ECG rhythm was during the time when the first defibrillation shock(s) were given and also whether CPR (e.g., chest compressions and/or ventilations) was provided to the patient and, if so, further view the overall quality of the CPR, before more highly trained personnel were able to arrive at the scene. The post-case review personnel are also able to view any and all relevant information recorded by the more advanced second medical device as well, and be able to determine from which medical device the information originated.

Figure 3A:
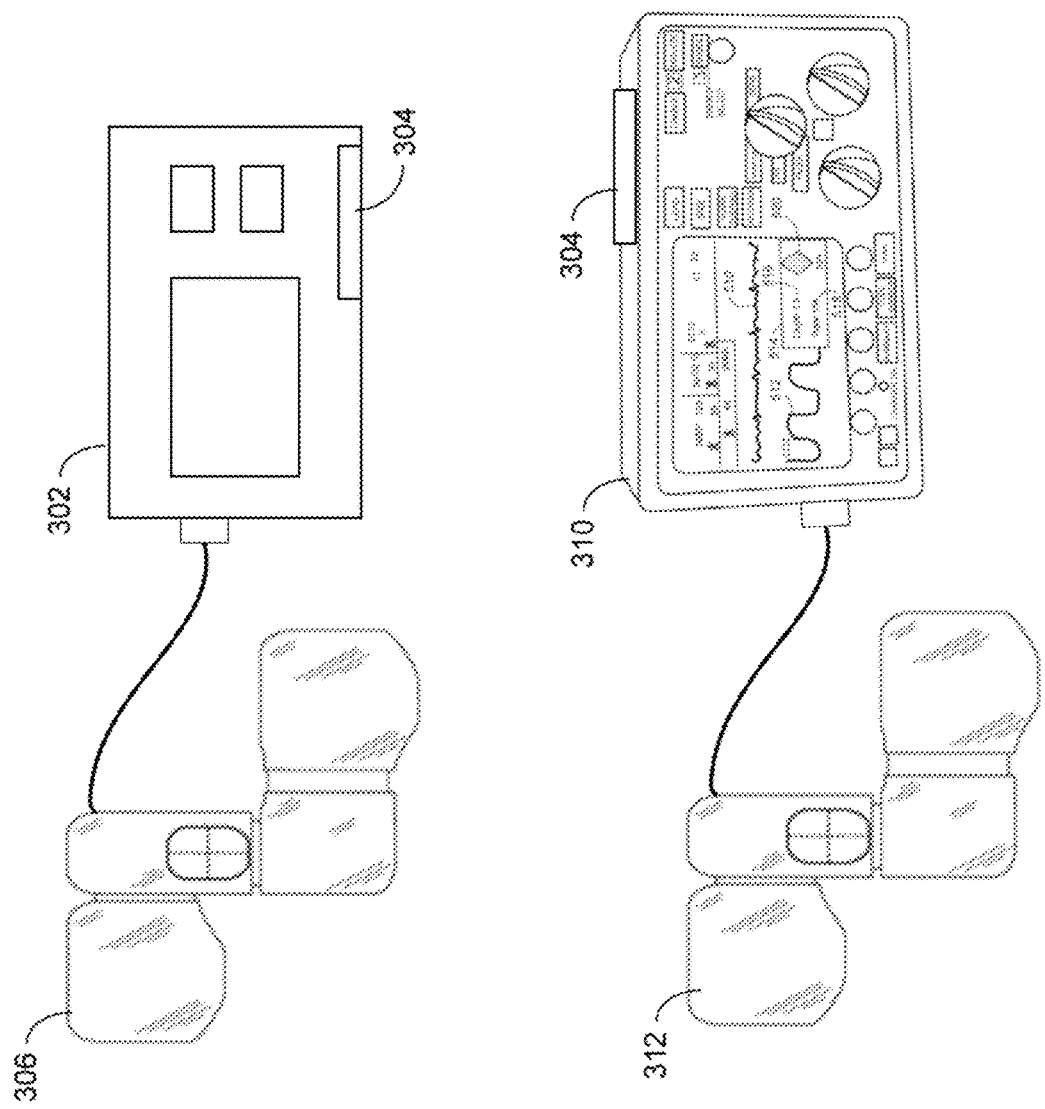
FIG. 3A is a schematic diagram showing a battery being transferred between medical devices, in accordance with at least one example disclosed herein.

For example, as shown in FIG. 3A, a patient can be initially treated by an AED 302 powered by battery 304. The AED 302 can be configured to record information related to the patient as well as treatment specific information onto a memory integrated into battery 304 as described above. In certain implementations, the memory can be integrated into a connector of the battery.

In certain implementations, the AED 302 can monitor patient electrical signals received from the integrated therapy pad 306 and record any patient physiological information determined from the electrical signals to the battery 304. Similarly, the AED can receive information related to any chest compressions applied to the patient from an integrated chest compression sensor included in the integrated therapy pad 306. If the AED 302 delivers one or more defibrillation and/or pacing shocks to the patient, the AED can record information related to the treatment to the battery 304 as well. For example, the information can include energy delivered to the patient in the shock as well as whether the shock successfully returned the patient to a normal cardiac rhythm.

Figure 8E:
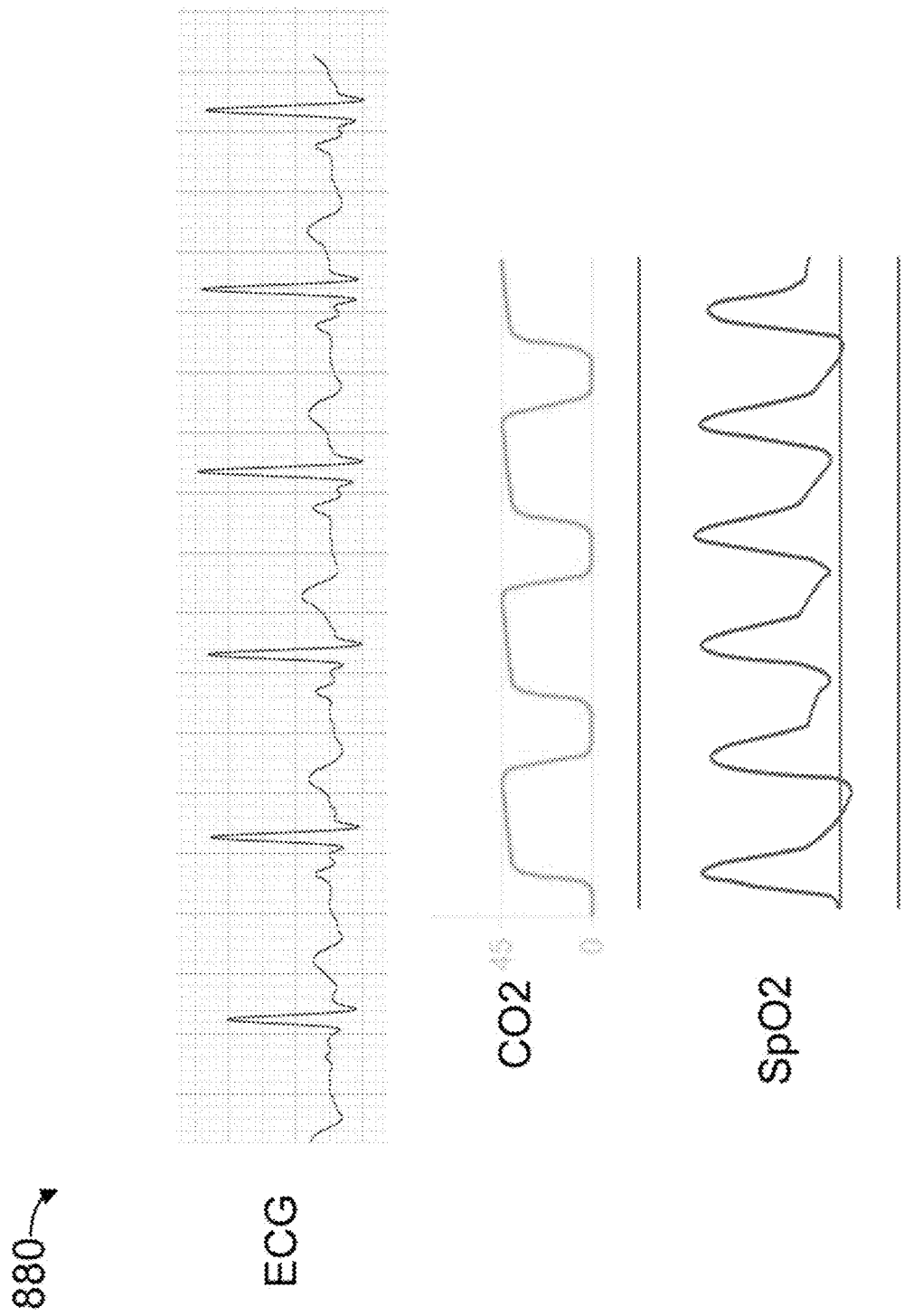
FIG. 8E shows sample waveform data stored in a medical device accessory-based memory, in accordance with at least one example disclosed herein.

In certain implementations, the battery 304 can be configured to store additional information related to the battery itself. For example, the information can include information such as the battery serial number (as assigned, for example, by the battery manufacturer or a medical device manufacturer), remaining capacity information, number of high energy charges, information related to AED functionality (e.g., self-test results, calibration information, electrode pad status/expiration) and other similar battery information. Additional examples of battery information is described below in the discussion of FIG. 8D. When the battery 304 is inserted into a device such as AED 302, the AED can create a battery information file as well that includes information about the battery being used for later reference. For example, the AED battery information file can include battery identification information, battery usage information, current battery status information, and other similar battery information. This AED battery file provides a data structure that can be retrieved to get historical usage information for batteries that have been inserted into a particular medical device such as an AED A specific battery software task can be configured to, when executed, cause a processor to read/write battery data to both the battery memory as described herein as well as to the memory of the AED (or other medical device being powered by the battery). The battery software task can be configured to write additional information such as installation date, self-test information, battery verification information, and any errors associated with the battery. During a self-test, the battery software task can confirm the battery manufacture date, confirm the current date, calculate the battery life consumed, calculate a battery remaining charge, log any errors, check for battery expiration, check the battery voltage, and update a display of the AED to include various information such as battery capacity and a battery expiration date. Upon completion of the self-test, the battery software task can be configured to update the battery consumed charge over time, wait for events indicating that the AED capacitor is charged and update the consumed charge accordingly, and update the AED display with remaining battery capacity information. However, it should be noted that the battery software task as described herein is provided by way of example only. Depending upon system design, the functionality of the battery software task as described herein can be divided among multiple more focused software tasks.

Referring again to FIGS. 3A-3D, upon arrival of emergency medical responders, treatment of the patient can be transferred to the more advanced defibrillator/monitor 310. In this example, the battery 304 can be removed from AED 302 and inserted into defibrillator/monitor 310. Upon insertion, the defibrillator/monitor 310 can access any information stored in the memory of battery 304 and can resume treatment of the patient based upon the information already collected by the AED 302. For example, if a defibrillation shock delivered by the AED 302 was unsuccessful, the defibrillator/monitor 310 can deliver a subsequent defibrillation shock to the patient using integrated therapy pad 312.

It should be noted that two integrated therapy pads 306 and 312 are shown by way of example only in FIG. 3A. In certain implementations, the integrated therapy pad 306 can be disconnected from the AED 302 and coupled to the defibrillator/monitor 310. For example, as shown in FIG. 3B, an integrated therapy pad can be disconnected from a first medical device and coupled to a second medical device while remaining in place on the patient.

Figure 3B:
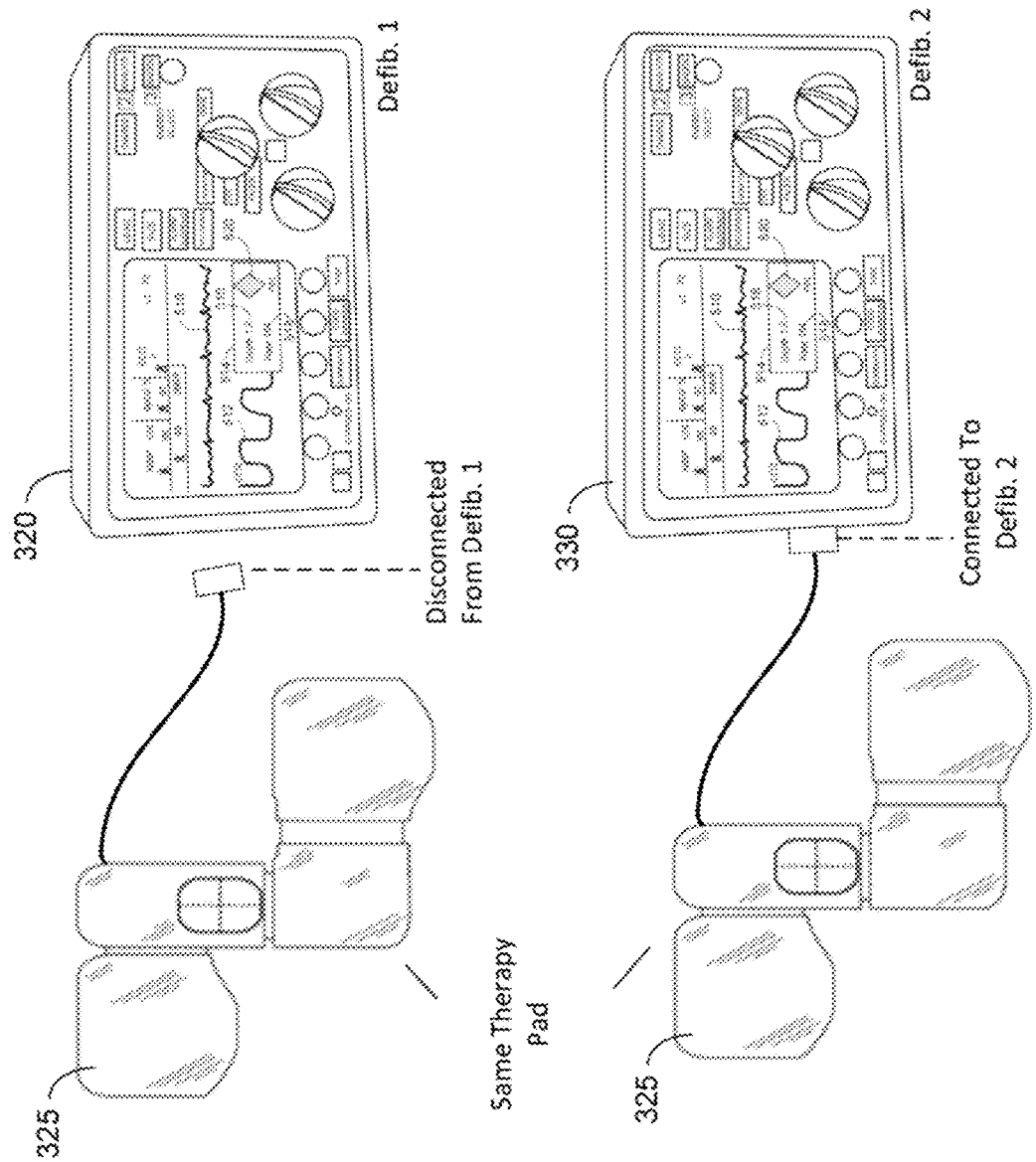
FIG. 3B is a schematic diagram showing an integrated therapy pad being transferred between medical devices, in accordance with at least one example disclosed herein.

More specifically, as shown in FIG. 3B, a medical device such as defibrillator 320 can be operably coupled to an integrated therapy pad 325 that includes, for example, a set of sensing and treatment electrodes as well as a chest compression sensor. A set of first responders can initially place the integrated therapy pad 325 onto a patient that is experiencing, for example, a cardiac event such as an arrhythmia. The defibrillator 320 can monitor and, if necessary, provide treatment to the patient via the integrated therapy pad 325, and while doing so, may record relevant patient and medical information, such as patient physiological data, patient characteristics, rescuer performance data, etc., to the integrated therapy pad 325. At a time when a second set of responders such as trained emergency medical responders arrive, it may be necessary to transfer monitoring and treatment of the patient to a second medical device. As shown in FIG. 3B, the second medical treatment device can be a second defibrillator 330. In this example, the emergency medical responders can disconnect the integrated therapy pad 325 from the first defibrillator 320 and couple the integrated therapy pad to the second defibrillator 330. By doing so, the data recorded by the first defibrillator 320 and written to the non-volatile memory of the integrated therapy pad 325 may be written to the second defibrillator 330, so that all the relevant patient case information is available together.

In certain implementations, a patient-coupled resuscitation device or other similar medical device accessory such as the integrated therapy pad 325 as shown in FIG. 3B can include an integrated memory that is configured to store information, similar to battery 304 as described above in regard to FIG. 3A. For example, the integrated memory in the accessory can be configured to store information about the patient such as measured physiological information. In some examples, the integrated memory in the accessory can be configured to store information about any treatments that have been delivered to the patient. For example, if the first defibrillator 320 has delivered one or more defibrillation shocks to the patient, information about the defibrillation shock can be stored on the memory in the integrated therapy pad 325. Then, when the integrated therapy pad 325 is coupled to the second defibrillator 330, the information about the patient and any potential treatment information stored on the memory can be transferred to the second defibrillator 330. The second defibrillator 330 can then continue treatment of the patient using the patient information and treatment information stored on the memory in the integrated therapy pads 325. Additional information about integrated memory in medical device accessories is provided in the discussion of FIGS. 5-6C below.

Figure 3C:
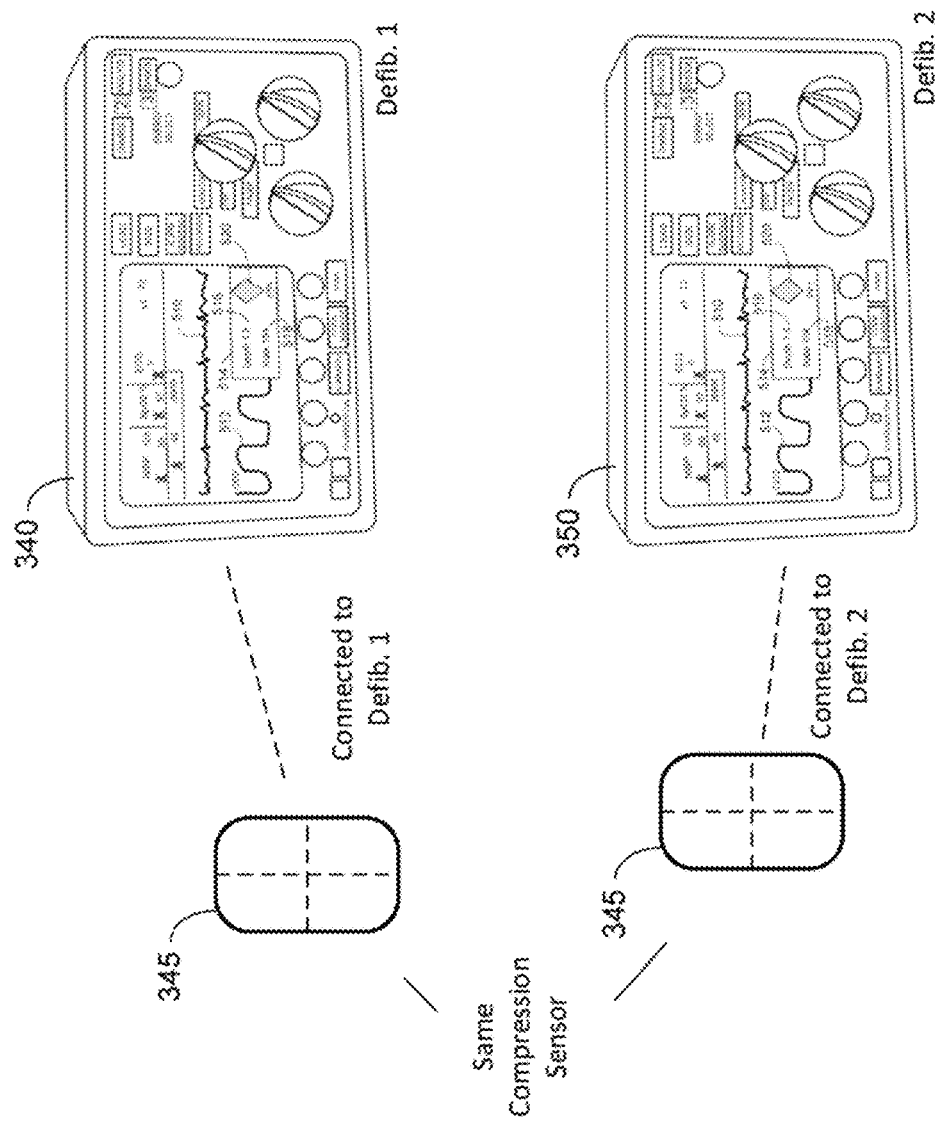
FIG. 3C is a schematic diagram showing a chest compression sensor being transferred between medical devices, in accordance with at least one example disclosed herein.

In certain implementations, additional accessories can be disconnected from a first medical device and operably coupled to a second medical device as described herein. For example, as shown in FIG. 3C, a medical device such as a first defibrillator 340 can be operably coupled to a chest compression sensor 345. Depending upon the capabilities of the first defibrillator 340 and the chest compression sensor 345, a wired or wireless connection can be established. For example, the first defibrillator 340 and the chest compression sensor 345 can be configured to establish a wireless connection using a short-range communication scheme such as Bluetooth® or a near field communication (NFC) protocol.

A set of first responders can initially place the chest compression sensor 345 onto a patient that is experiencing, for example, a cardiac event such as an arrhythmia. If the first responders administer CPR treatment to the patient, the chest compression sensor 345 can monitor and record various information related to the treatment such as average compression rate, average compression depth, maximum compression depth, minimum compression depth, elapsed time of treatment administered, release velocity, and other relevant information. The first defibrillator 340 can monitor and, if necessary, present feedback to the first responders via an integrated display on the device. At a time when a second set of responders such as trained emergency medical responders arrive, it may be necessary to transfer monitoring and treatment of the patient to a second medical device. As shown in FIG. 3c, the second medical treatment device can be a second defibrillator 350. In this example, the emergency medical responders can disconnect the chest compression sensor 345 from the first defibrillator 340 and couple the chest compression sensor 345 to the second defibrillator 350. If there is a wired interface between the first defibrillator 340 and the chest compression sensor 345, this can include disconnecting the chest compression sensor 345 from the first defibrillator and connecting the chest compression sensor 345 to the second defibrillator. If there is a wireless connection between the first defibrillator 340 and the chest compression sensor 345, the emergency medical responders can physically move the first defibrillator away from the chest compression sensor 345 (e.g., more than ten feet away) and place the second defibrillator 350 into closer proximity to the chest compression sensor 345 (e.g., within three to five feet in case of a proximity based detection). The chest compression sensor 345 and the second defibrillator 350 can be configured to automatically establish a wireless connection upon being brought into proximity of one another. In some examples, one or both of the chest compression sensor 345 and one or both of defibrillators 340 and 350 can have a manual connection button that, upon activation (e.g., being pressed by a medical responder) will initiate a wireless connection protocol.

For example, a patient-coupled resuscitation device or other similar accessory and an external medical device can be configured to communicate using a specific wireless connection protocol such as Bluetooth, Zigbee, near-field communications, infrared, and other similar protocols. In certain implementations, if the accessory is configured to communicate with a medical device using Bluetooth, the accessory can be configured to monitor a specific frequency such as 2.45 GHz for a Bluetooth broadcast signal being issued by the medical device. Based upon the type of Bluetooth being used, the broadcast signal may only be detectable within a specific radius of the medical device (e.g., within 30 feet). When positioned within that radius, the accessory and the medical device may exchange authentication information and begin to communicate wirelessly. In another example, the accessory and the medical device can be configured to communicate using another communication protocol such as Zigbee. In such an example, the accessory can monitor a specific frequency such as 2.4 GHz for a Zigbee broadcast signal being issued by the medical device. Upon receiving the broadcast signal, the accessory and the medical device can exchange authentication information and communicate using the Zigbee protocol.

It should be noted that the specific communication protocols and signal frequencies as described above are by way of example only. In certain examples, the accessory can be configured to monitor additional frequency ranges for broadcast communication signals. For example, the accessory can be configured to monitor signals around 850-950 MHz, 2.2-2.6 GHz, 4.75-5.25 GHz, 5.8-6.0 GHz, and other similar frequencies. Similarly, a 30 foot radius in which a broadcast signal is detectable as noted above is provided by way of example only. In certain examples, a wireless communication broadcast radius can include 1-2 feet, 2-5 feet, 5-10 feet, 10-25 feet, and 25-50 feet. It should also be noted that the medical device is described as transmitting the broadcast signal above by way of example only. In some implementations, the accessory can be configured to transmit a wireless communication protocol broadcast signal for detection by one or more medical devices.

Similar to the above discussion of FIG. 3B, the chest compression sensor 345 can include an integrated non-volatile memory that can be configured to store information about the patient as well as patient treatment information including, for example, average compression rate, average compression depth, maximum compression depth, minimum compression depth, release velocity, elapsed time of treatment administered, and other similar information. When the chest compression sensor 345 is coupled to the second defibrillator 350, the information about the patient and any potential treatment information stored on the memory can be transferred to the second defibrillator 350. The second defibrillator 350 can then continue monitoring treatment of the patient using the patient information and treatment information stored on the memory in the chest compression sensor 345 as reference for informing future monitoring and treatment.

Figure 3D:
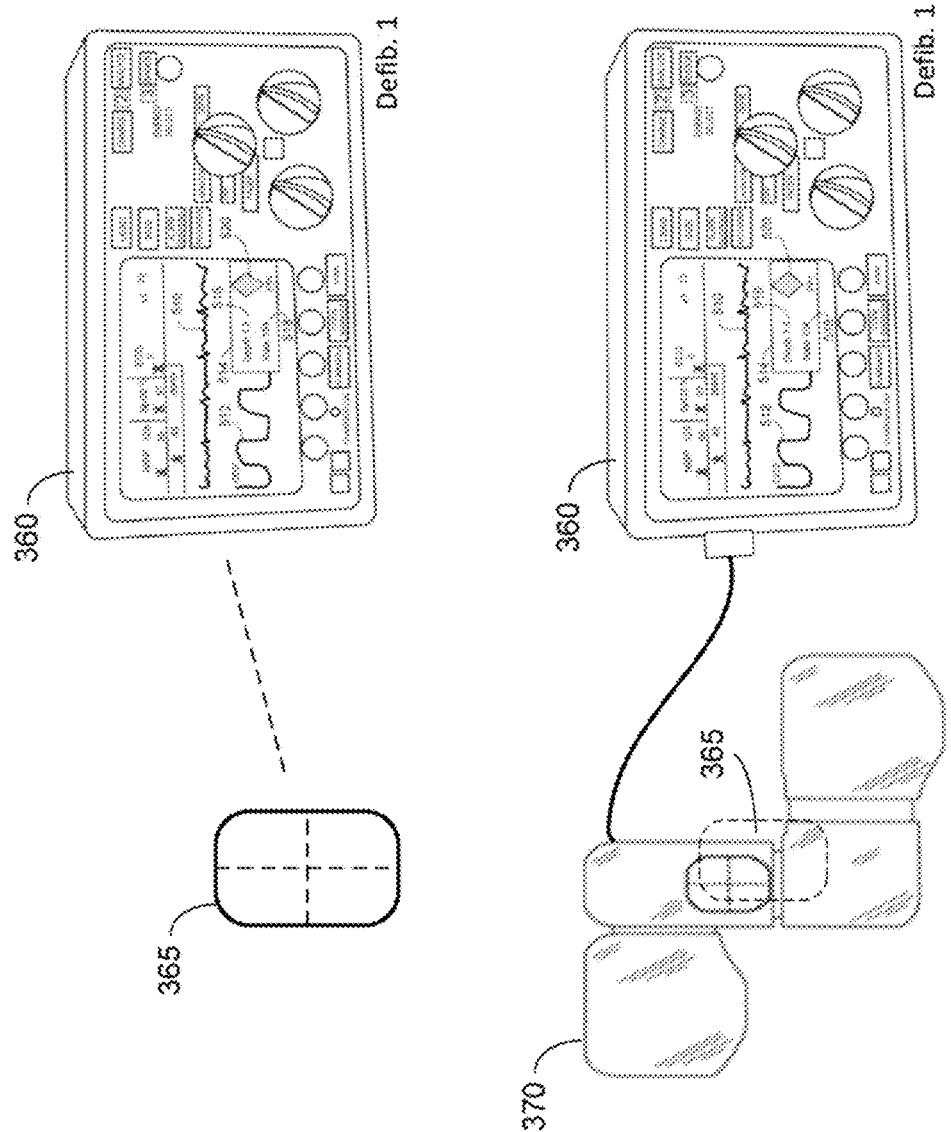
FIG. 3D is a schematic diagram showing an integrated therapy pad being overlaid on a chest compression sensor, in accordance with at least one example disclosed herein.

In addition to transferring information between medical devices, the techniques and processes as described herein can be used to transfer information between medical device accessories as well. For example, as shown in FIG. 3D, a medical device such as a defibrillator 360 can be operably coupled to a patient-coupled resuscitation device or other similar medical device accessory such as chest compression sensor 365. Initial treatment such as CPR can be administered to a patient. Information about the treatment can be recorded by both the defibrillator 360 and the chest compression sensor 365. For example, the chest compression sensor can be configured to monitor and record various information such as average compression rate, average compression depth, maximum compression depth, minimum compression depth, release velocity, CPR fraction (e.g., percentage of time that CPR is actually being given to the patient during periods designated for CPR), percentage of compression depth and rate that are within target ranges, elapsed time of treatment administered, and other similar information. At some point, another accessory can be operably coupled to the defibrillator 360. For example, as shown in FIG. 3D, an integrated therapy pad 370 can be overlaid onto the chest compression sensor 365. The integrated therapy pad 370 can be coupled to the defibrillator 360 and begin monitoring the patient and, if necessary, provide treatment such as a defibrillation shock to the patient. In certain implementations, upon placement over the chest compression sensor 365, the integrated therapy pad 370 can download or otherwise access the information stored on the chest compression sensor. For example, the integrated therapy pad 370 can be configured to establish a wireless connection with the chest compression sensor 365 using a short-range communication protocol such as Bluetooth®. Upon establishing a connection, the integrated therapy pad 370 can access and download the information stored on the memory in the chest compression sensor.

Figure 4:
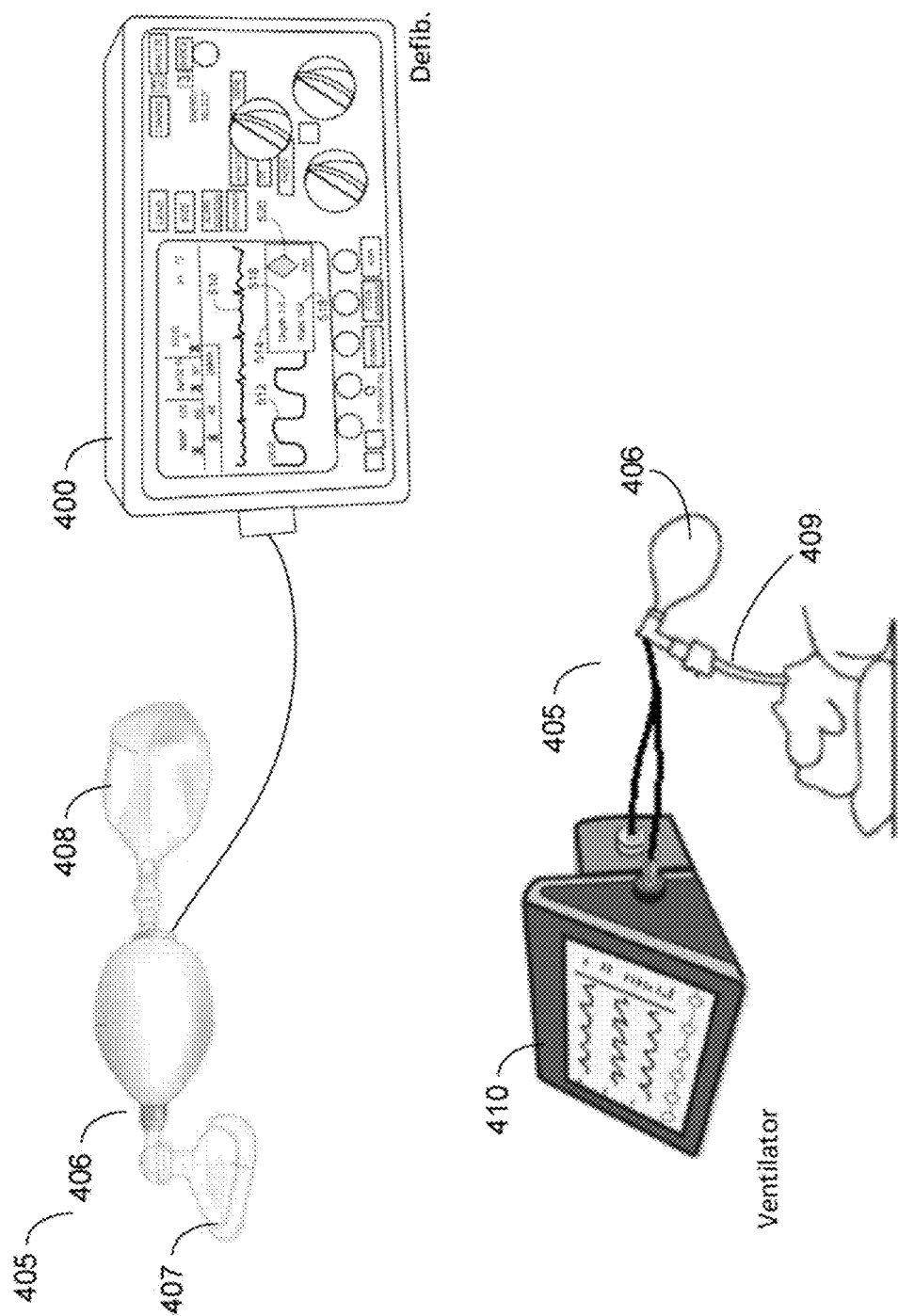
FIG. 4 is a schematic diagram showing a breathing assistance accessory being transferred between medical devices, in accordance with at least one example disclosed herein.

In addition to transferring a patient-coupled resuscitation device and/or other medical device accessory between two medical devices of the same or a similar functionality, a medical device accessory can be transferred between two medical devices that have different overall functionalities. For example, a medical device accessory such as a breathing assistance accessory including a flow sensor can be transferred between a defibrillator and a ventilator. As shown in FIG. 4, during initial patient treatment, a patient-coupled resuscitation device such as breathing assistance accessory 405 can be initially coupled to a defibrillator 400. As shown in FIG. 4, the breathing assistance accessory 405 can include a bag valve mask and flow sensor assembly 406 that includes, for example, a flow sensor configured to measure air flow. The breathing assistance accessory 405 can further include a mask 407 for placement over the patient's mouth and a bag 408 that can be used by a medical responder to pump air into the patient's lungs.

As further shown in FIG. 4, the breathing assistance accessory 405 can be disconnected from the defibrillator 400 and operably coupled to an automatic ventilator 410. Additionally, upon transferring to the automatic ventilator 410, the mask 407 portion of the breathing assistance accessory 405 can be removed, and the valve and sensor assembly 406 can be attached to an endotracheal tube 409 that has been integrated into the patient's airway for automatic ventilation. Depending upon the design of the breathing assistance accessory 405, the bag 408 can also be removed.

Similar to above, when coupled to the defibrillator 400, an integrated memory in the breathing assistance accessory 405 can be storing information measured by the flow sensor. For example, the memory can store information related to rate of air flow, volume of air flow, ventilation tidal volume, minute volume, ventilation rate, percentage of tidal volume or ventilation rate that are within desired target ranges, and other similar air flow information. When disconnected from the defibrillator 400 and coupled to the ventilator 410, the information stored on the memory in the breathing assistance accessory 405 can be transferred to the ventilator as described herein. In certain situations, the resuscitation accessory may be able to record the particular medical device identification to memory, for the benefit of the second medical device or computing device. The second medical device or other computing device may then be able to initiate a network and/or proximity search for the first medical device and establish a communicative connection to exchange relevant medical information without further requiring the accessory.

As an example use scenario, an initial emergency service or responder arrives and monitors the patient using a first defibrillator/monitor equipped with various accessories, such as electrodes and a chest compression sensor in accordance with the present disclosure. The first defibrillator/monitor connected to those accessories records its unique signature or serial number thereto. When another, similar or possibly more advanced, second medical device arrives on the scene, the accessory(ies) are disconnected from the first defibrillator/monitor and connected to the second medical device. The second medical device reads the signature of the first defibrillator/monitor from the accessory, and then initiates a network or proximity search for the particular device with the unique signature. Once that device (first defibrillator/monitor) is discovered, then a communicative connection may be established so as to transfer relevant medical information immediately.

In another example, if an ambulance service is transferring a patient to a hospital, a patient-coupled resuscitation device or other similar accessory disconnected from a first medical device associated with the ambulance service and subsequently connected to a second medical device associated with the hospital would have recorded thereon the signature corresponding to the first medical device associated with the ambulance service. Once the second medical device associated with the hospital reads that there is an identification signature recorded on the resuscitation accessory, the second medical device may initiate a network or proximity search for the first medical device (in this case, the ambulance service may remain nearby and/or stay on the same network so as to be available) and establish a communicative connection to initiate the transfer of relevant medical information. For example, the devices may establish communication via a near field communication (NFC), Bluetooth, WiFi, or other suitable manner, and then initiate data transfer directly, without further requiring the accessory.

In the event that the disconnecting medical device is not maintained in close proximity to the new connecting medical device for a complete data transfer, the device identification signature may still be stored with the record on the newer medical device such that whenever the previous medical device establishes a link back to a wireless/wired connection, the two medical devices may then connect with one another to initiate and/or complete data transfer.

Integrated and Removable Memory in Medical Device Accessories

Figure 5A:
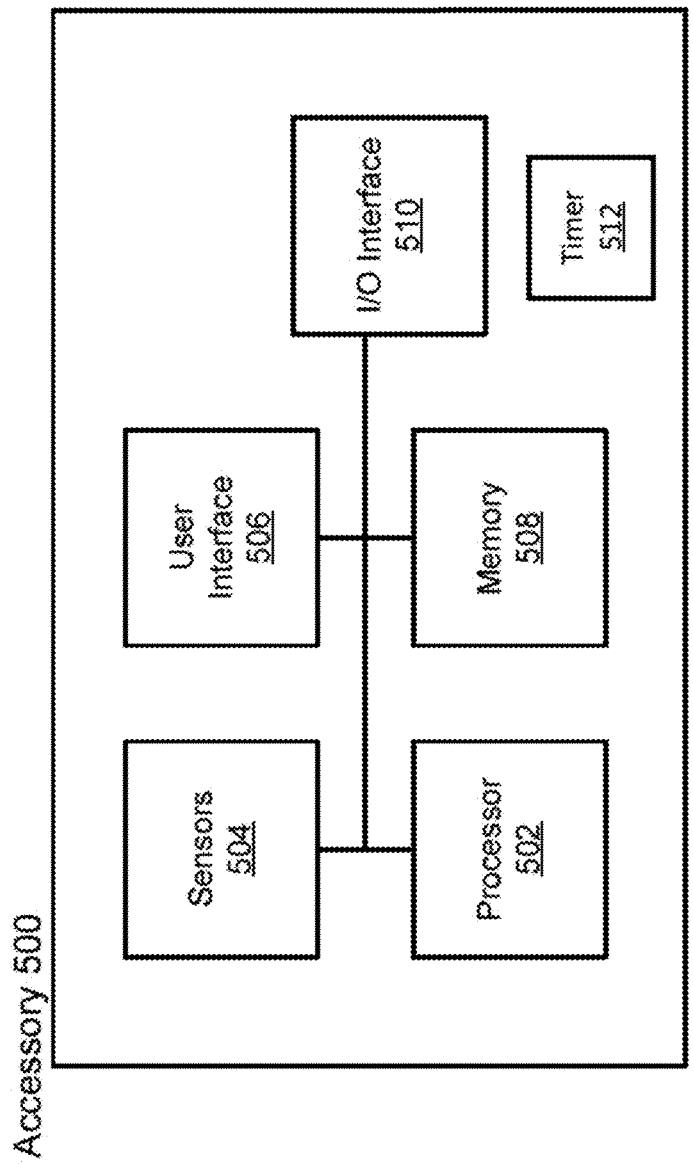
FIG. 5A is a block diagram of a medical device accessory including an integrated memory, in accordance with at least one example disclosed herein.
Figure 6A:
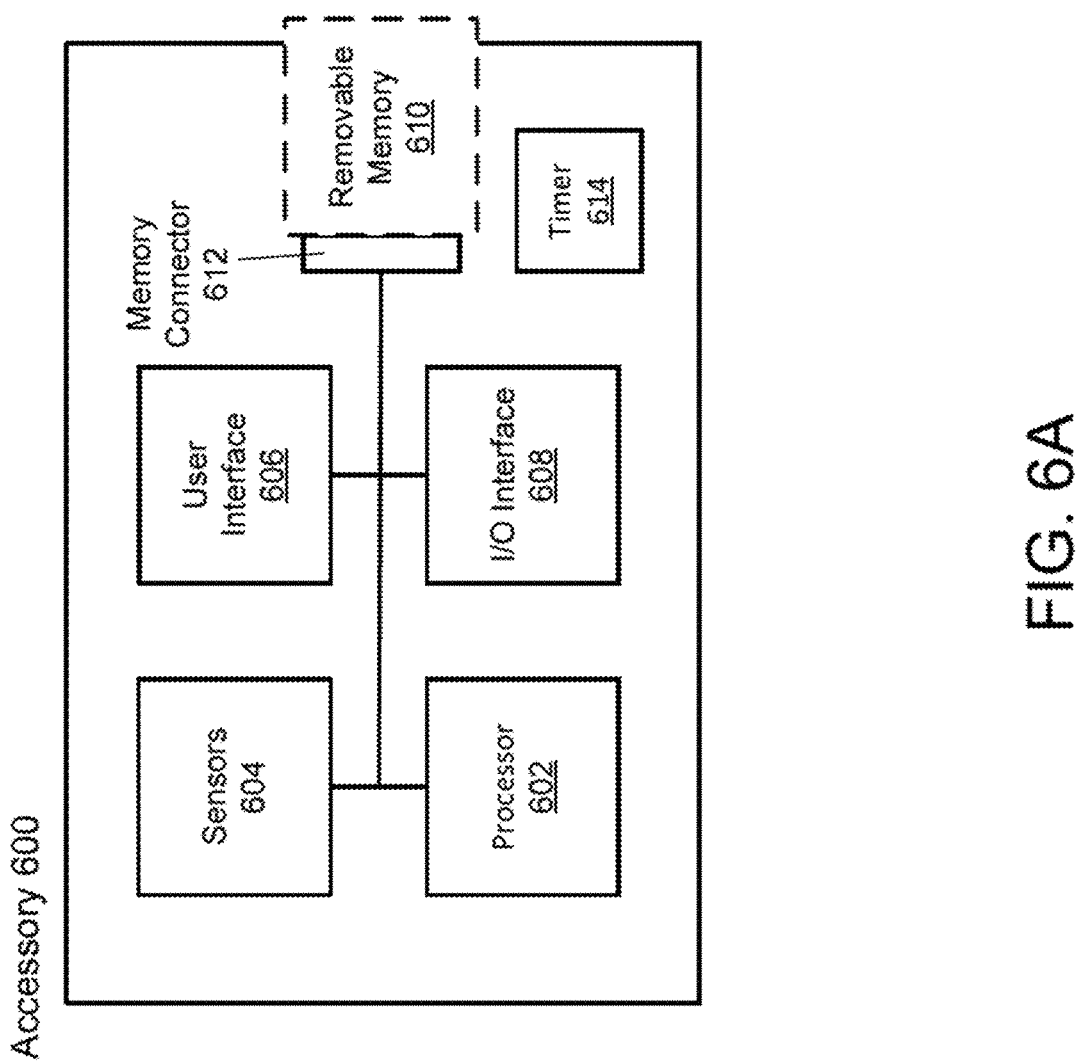
FIG. 6A is a block diagram of a medical device accessory including a removable memory, in accordance with at least one example disclosed herein.

As noted above, a patient-coupled resuscitation device and medical device accessories such as an integrated therapy pad, a chest compression sensor, a breathing assistance accessory such as a BVM, a set of defibrillation electrodes, a battery for powering one or more medical devices, and other similar medical device accessories can include an integrated memory configured to store various information as described herein. For example, as shown in FIG. 5A, a medical device accessory 500 can include various components configured to facilitate collection and storage of information related to operation of the medical device accessory and treatment provided to a patient. As shown in FIG. 5A, the accessory 500 can include a processor 502, one or more sensors 504, a user interface 506, a memory 508, an input/output (I/O) interface 510, and a timer 512. In some examples, the memory 508 used may employ a serial data interface to reduce pincount on connectors between the accessory and the medical device particularly when the memory 508 is configured to be removable as shown in FIG. 6A. For instance, the memory 508 may be the AT24CM02 2 Mb I2C compatible 2-wire Serial EEPROM (MicroChip Inc.) Alternatively, the pincount may be further reduced by using the 2 wire AT21CS01 2 lead with the clock, data and power combined into a single input.

In some implementations, the processor 502 includes one or more processors (or one or more processor cores) that each are configured to perform a series of instructions that result in manipulated data and/or control the operation of the other components of the accessory 500. As referred to herein, the processor 502 can be configured to execute a function where software is stored in a data store (e.g., memory 508) coupled to the processor, the software being configured to cause the processor to proceed through a sequence of various logic decisions that result in the function being executed. The various components that are described herein as being executable by the processor 502 can be implemented in various forms of specialized hardware, software, or a combination thereof. For example, the processor 502 can be a digital signal processor (DSP) such as a 24-bit DSP. The processor 502 can be a multi-core processor, e.g., having two or more processing cores. The processor 502 can be an Advanced RISC Machine (ARM) processor such as a 32-bit ARM processor or a 64-bit ARM processor. The processor 502 can execute an embedded operating system, and include services provided by the operating system that can be used for various functions performed by the accessory 500.

As further shown in FIG. 5A, the one or more sensors 504 can be operably coupled to the processor 502 and configured to provide information to the processor. Depending upon the functionality of accessory 500, the sensors 504 can vary. For example, if the accessory is a chest compression sensor, the sensors 504 can include one or more accelerometers configured to measure chest compression information such as chest compression depth. In another example, if the accessory 500 is a breathing assistance accessory, the sensors 504 can include a flow sensor configured to measure air rate and volume information. Other examples of sensors can include ECG sensing electrodes, vibrational sensors, acoustic sensors, tissue fluid monitors, and other types of motion sensors such as gyroscopes and magnetometers.

As also shown in FIG. 5A, the user interface 506 can be operably coupled to the processor 502. It should be noted that, depending upon the functionality and design of the accessory 500, a user interface may not be included. However, in this example, the accessory includes a user interface 506 that can include one or more physical interface devices such as input devices, output devices, and combination input/output devices and a software stack configured to drive operation of the devices. These user interface 506 can be configured to can render visual, audio, and/or tactile content. Thus, the user interface 506 can receive input or provide output, thereby enabling a user to interact with the accessory 500.

As further shown in FIG. 5A, the memory 508 can be operably coupled to the processor 502. The memory 508 can include one or more of non-transitory computer-readable media, such as flash memory, solid state memory, magnetic memory, optical memory, cache memory, combinations thereof, and others. The memory 508 can be configured to store executable instructions and data used for operation of the accessory 500. In certain examples, the memory 508 can include executable instructions that, when executed, are configured to cause the processor 502 to perform one or more operations. In some examples, the memory 508 can be configured to store information received from, for example, the processor 502 and/or the sensors 504.

Additionally, as shown in FIG. 5A, the I/O interface 510 can be operably coupled to the processor 502. The I/O interface can facilitate the communication of information between the accessory 500 and one or more other devices or entities. For example, the I/O interface 510 can be configured to establish a communication link and facilitate transfer of information stored in memory 508 to another medical device accessory, a medical device, a computing device associated with a healthcare provider or other similar person providing treatment to a patient, and other similar computing devices. For the information stored in memory 508 to be maintained during transition between when it is unplugged from a first device and when the stored information is accessed again, the memory 508 should be non-volatile, e.g. FLASH, EEPROM, battery-backed static memory, etc.

In certain implementations, the I/O interface can be configured to provide a wired or wireless connection. For example, the I/O interface can include a physical electrical connector such as a universal serial bus (USB) port that is configured to provide a wired connection with another computing device for the transfer of information. In some examples, the I/O interface 510 can include communications circuitry for transmitting data in accordance with a Bluetooth® wireless standard for exchanging such data over short distances to an intermediary device. For example, such an intermediary device can be configured as a medical device, another medical device accessory, a smartphone, a tablet, a portable computing device, and/or other devices in proximity of the accessory 500. The intermediary device(s) may in turn communicate the data to a remote server over a broadband cellular network communications link. The communications link may implement broadband cellular technology (e.g., 2.5G, 2.75G, 3G, 4G, 5G cellular standards) and/or Long-Term Evolution (LTE) technology or GSM/EDGE and UMTS/HSPA technologies for high-speed wireless communication. In some implementations, the intermediary device(s) may communicate with a remote server over a Wi-Fi™ communications link based on the IEEE 802.11 standard.

As further shown in FIG. 5A, the timer 512 can be configured to record timing information related to operation of the accessory 500 and the interaction of the accessory with an external medical device. For example, in certain implementations, the internal timer of the external medical device and the timer 512 may not be synchronized. In such an example, the timer 512 can be configured to record timing information to memory 508 that provides additional information related to the operation of the accessory 500 in concert with the external medical device. In some examples, the timer 512 can be synchronized to the time of the external medical device. In other examples, the timer 512 can continue its original timing while adding a marker or other similar indication to a recorded timing information to provide an offset or synchronization point for aligning timing information with the external medical device.

In some examples, the accessory 500 connected to the first external medical device may record timing information (e.g., clock time) of the first external medical device prior to being disconnected. When the accessory 500 is disconnected from a first external medical device, the timer 512 of the accessory 500 may continue to keep time as if the accessory 500 remained connected with the first external medical device. And then when the accessory 500, which has maintained the timing of the first external medical device, is connected to a second external medical device, any difference in time between the first and second external medical devices may be noted, or otherwise corrected for. As an example, when disconnected, the timer 512 can record timing information to the memory 508 indicating the clock time of the first medical device and when the accessory 500 was disconnected. When the accessory is connected to a second external medical device, the second external device can include a different internal time as compared to one or both of the first external medical device and the accessory 500. In such an example, the recorded timing information as stored on memory 508 can be used to synchronize the second medical device timer to the timer of the first medical device. In some examples, the recorded timing information on memory 508 can be used to offset or otherwise adjust timing information as recorded by the second external medical device to provide a synchronized and ordered recording of all treatment events measured by the accessory 500 as administered by both the first external medical device and the second external medical device. Or, when the accessory is connected to the second medical device, the timing difference between the first medical device and the second medical device may simply be noted.

In certain implementations, the accessory 500 can be configured to monitor and provide treatment to a patient as described herein. In such an example, the processor 502 can be configured to store information on the memory 508 about the patient and any treatment provided to the patient. For example, the processor 502 can be configured to store information measured by the sensors 504 to the memory. Additionally, the processor 502 can be configured to store information related to the patient that may be entered on the user interface 506 or otherwise received from an external device such as a medical device that the accessory 500 is connected to. In some examples, the processor 502 can be configured to store information related to any treatment provided to the patient on the memory 508. The treatment information can be based upon measured information from the sensors (e.g., chest compression information that is indicative of CPR treatment being performed) or information received from a medical device such as defibrillation shock information.

Figure 5B:
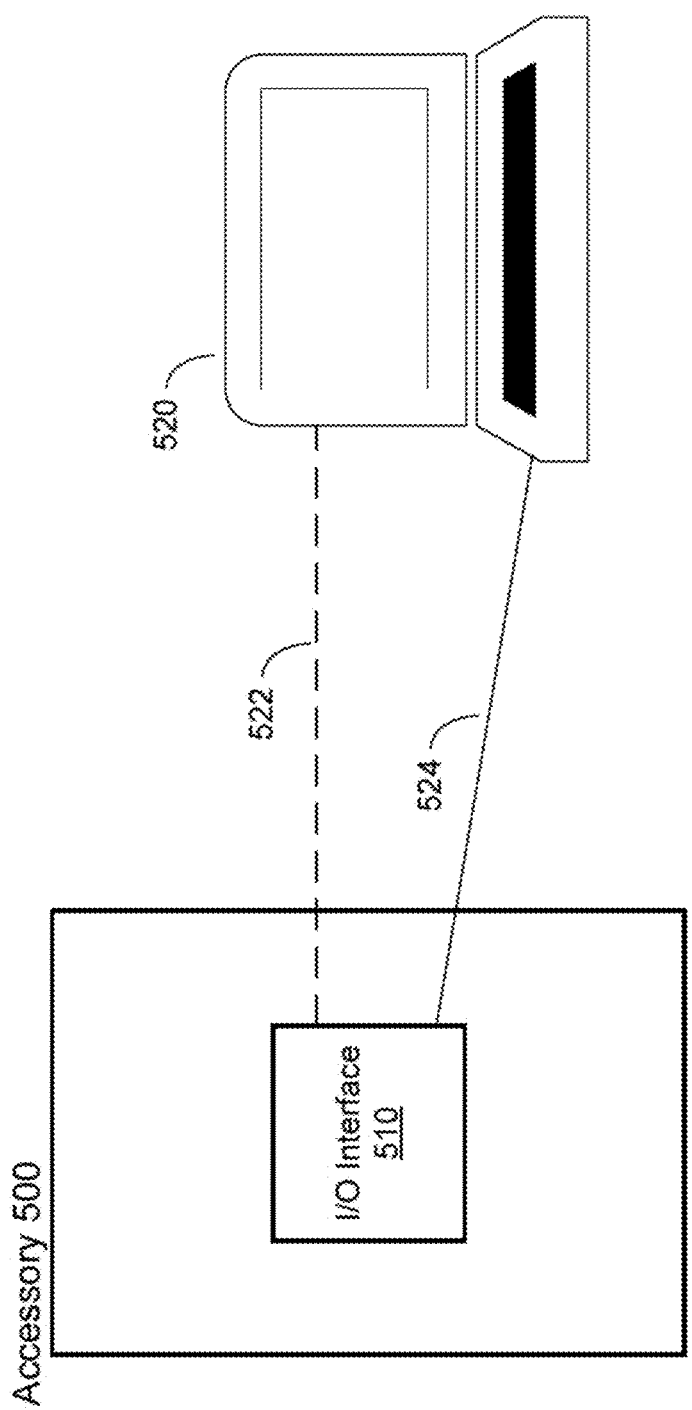
FIG. 5B is a schematic diagram showing the accessory of FIG. 5A operably coupled to a computing device, in accordance with at least one example disclosed herein.

As shown in FIG. 5B, information stored on the accessory 500 can be transferred to another device such as computing device 520. For example, the computing device 520 can be a computer associated with a patient's physician. Following treatment, the physician may want to review the patient's information as stored on the accessory 500. The computing device 520 can establish a connection to the accessory 500 via the I/O interface. For example, as shown in FIG. 5B, the computing device 520 can establish a wireless connection 522 and/or a wired connection 524 with the accessory 500. The physician can then access the information stored on the accessory 500 via, for example, a user interface similar to those as described below in the description of FIGS. 9A and 9B.

Figure 5C:
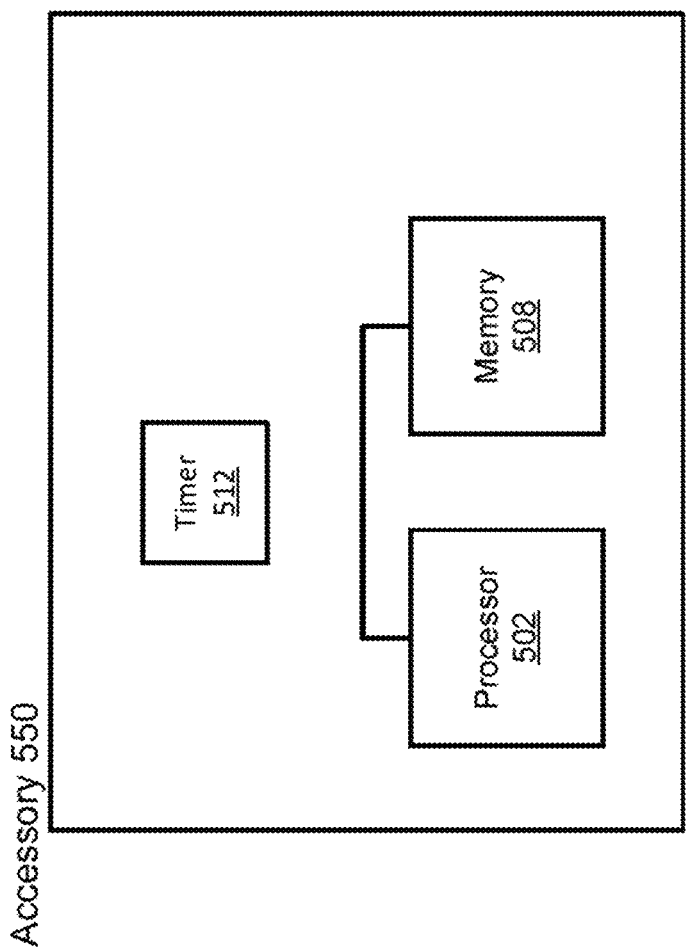
FIG. 5C is a block diagram of an alternative medical device accessory including an integrated memory, in accordance with at least one example disclosed herein.

It should be noted that components shown as integrated into accessory 500 in FIGS. 5A and 5B and described above are provided by way of example only. In some implementations, the accessory can include a reduced set of components as compared to that shown in FIG. 5A. For example, in certain implementations, a sample accessory 550 can include a reduced set of components such as those shown in FIG. 5C. For example, accessory 550 can include processor 502, memory 508, and timer 512. In such an example, the accessory 550 can be configured to record timing information as described above as well as information received from an external medical device. Depending upon the type of patient-coupled resuscitation device or other similar accessory and the problems the accessory addresses, a combination of components between those included in FIG. 5A and those included in FIG. 5C can be included. For example, a patient-coupled resuscitation device or other similar accessory can include a processor, one or more sensors, a memory, and a timer. In some examples, a patient-coupled resuscitation device or other similar accessory as described herein can include a processor, one or more sensors, a memory, an I/O interface, and a timer. As such, the accessory diagrams as shown in FIGS. 5A and 5C are merely provided by way of example only.

In addition to having an integrated memory as described herein, a patient-coupled resuscitation device or other similar accessory can include a removable memory. For example, as shown in FIG. 6A, an accessory 600 can include a processor 602, one or more sensors 604, a user interface 606, an I/O interface 608, and a timer 614. These components can be operably coupled and configured to function in a corresponding manner to similarly named components as shown in FIG. 5A and described above. However, as further shown in FIG. 6A, the memory 610 can be included in a removable module that is configured to be detached or otherwise removed from the accessory 600. For example, the removable memory 610 can be operably coupled to the other components of the accessory 600 via a memory connector 612. The memory connector 612 can be configured to removably receive the removable memory 610 and to establish an electrical connection between the removable memory and the other circuit components of the accessory 600 (e.g., processor 602, sensors 604, user interface 606, and I/O interface 608). In certain implementations, the I/O interface 608 can be configured to communicate directly with the removable memory 610 via the memory connector 612 and act as an intermediary between the removable memory 610 and the other circuit components of the accessory 600. In some examples, timer 614 can be configured to record timing information as described above to the removable memory 610.

In certain examples, the removable memory 610 can be implemented as a commercially available portable memory device such as a USB memory device, a secure digital (SD) memory device, and other similar portable storage devices. The removable memory 610 can be housed within the accessory 600 in a protected area that is not exposed to any potential body fluids or other debris that can result from treatment of a patient. As such, accessing the removable memory 610 may require removal of a portion of a housing of the accessory 600 or another similar physical interaction with the accessory to provide access to the removable memory.

Figure 6B:
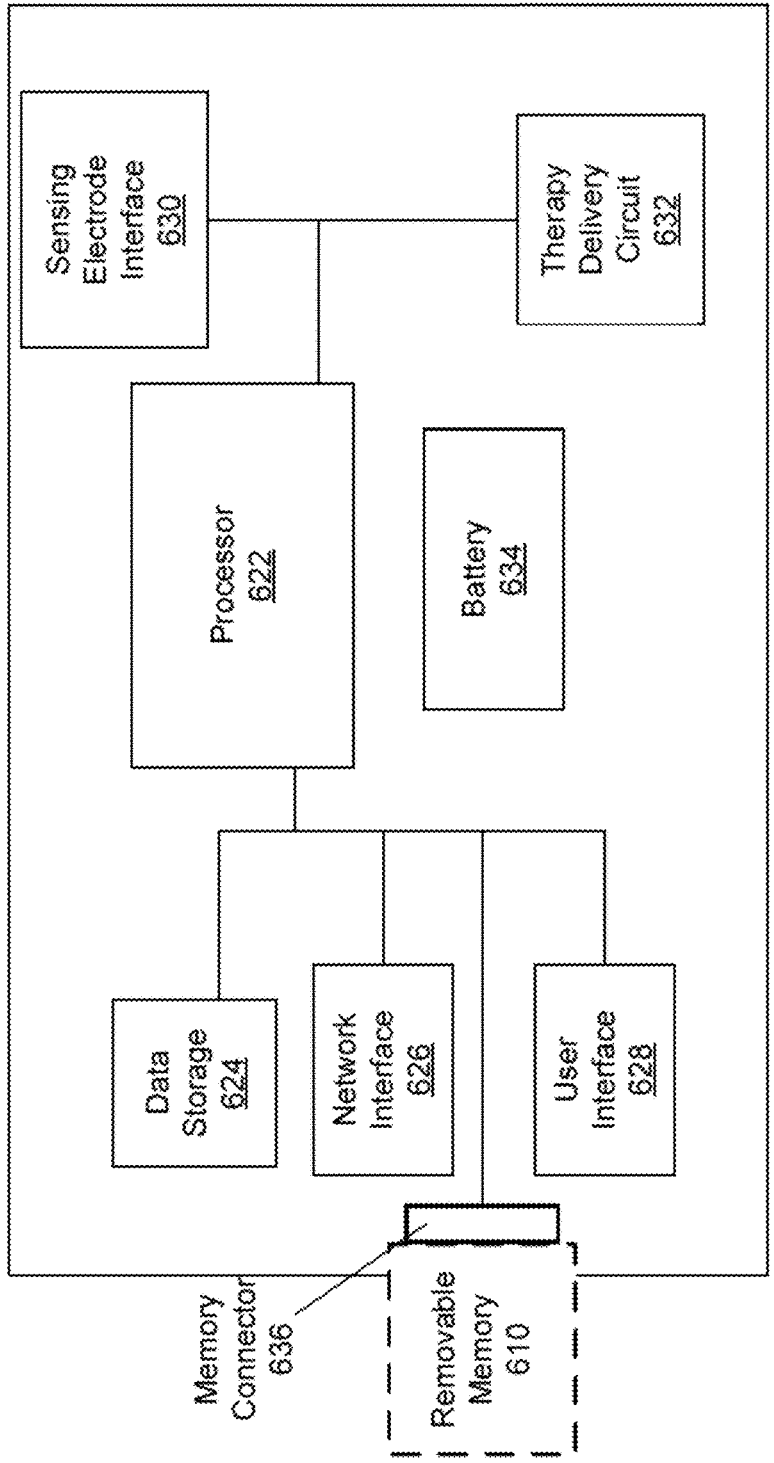
FIG. 6B is a block diagram of a medical device including the integrated memory of FIG. 6A, in accordance with at least one example disclosed herein.

In certain examples, to transfer information contained on the removable memory 610, the removable memory 610 can be removed from the accessory 600 and placed into or otherwise operably coupled to another device. For example, as shown in FIG. 6B, removable memory 610 can be directly connected to a medical device such as defibrillator 620. As described above, during treatment of a patient a first medical device can be replaced or otherwise supplemented with a second medical device. In such an example, information stored about the patient and any treatment provided by the first medical device can be transferred to the second medical device using a removable memory as is shown in FIGS. 6A and 6B and described herein.

Referring back to FIG. 6B, the defibrillator 620 can include a processor 622 configured to perform one or more instructions during operation of the defibrillator as described herein. Additionally, the defibrillator 620 can include a data storage 624, a network interface 626, a user interface 628, a sensing electrode interface 630, a therapy delivery circuit 632, and a battery 634.

Additionally, as shown in FIG. 6B, the defibrillator 620 can include a memory connector 636 that is configured to operably connect to the removable memory 610. Upon connection, the processor 622 can access the removable memory 610 and, if necessary, transfer any information contained on the removable memory to, for example, data storage 624 for local analysis and processing. For example, if a patient has been provided treatment by another medical device, the defibrillator 620 can access this information to determine what treatment has already been provided to the patient and to continue a similar treatment plan with the patient, if necessary.

It should be noted that defibrillator 620, and its associated internal components, are provided by way of example only in FIG. 6B. As noted above, the removable memory 610 can be operably coupled to additional medical devices as described herein such as automated ventilators for the transferring of information as described herein.

Figure 6C:
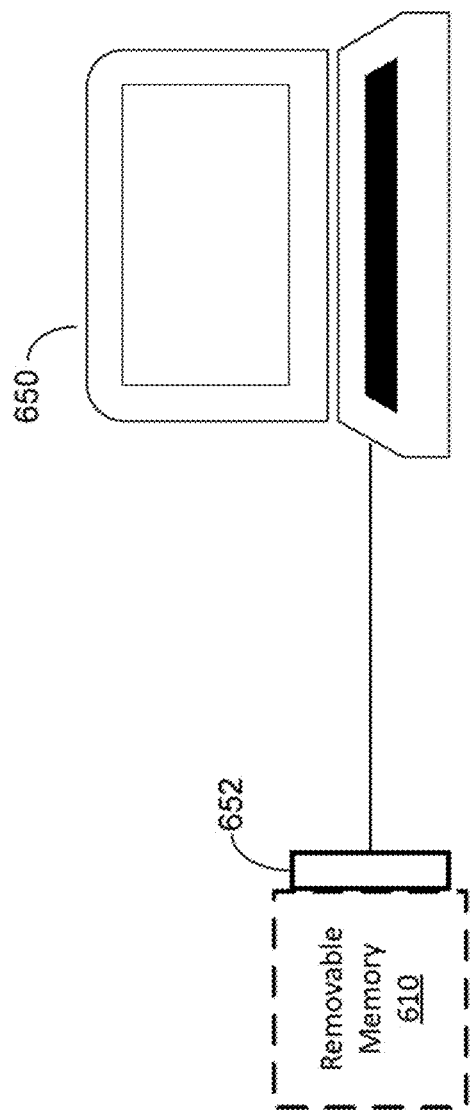
FIG. 6C is a schematic diagram showing the removable memory of FIG. 6A operably coupled to a computing device, in accordance with at least one example disclosed herein.

In addition to transferring the information contained on removable memory 610 to another accessory or a medical device as shown in FIG. 6B, the information can also be transferred to a computing device or docking station that provides a communicative connection to a computing device. As shown in FIG. 6C, information stored on the removable memory 610 can also be transferred to computing device 650. For example, the computing device 650 can be a computer associated with a patient's physician. Following treatment, the physician may want to review the patient's information as stored on the removable memory 610 and as collected by the accessory 600. The removable memory 610 can be operably coupled to a memory connector 652 that is connected to the computing device 650. The physician can then access the information stored on the accessory 600 via, for example, a user interface similar to those as described below in the description of FIGS. 9A and 9B.

It should be noted that the memory connector 652 as shown in FIG. 6C is shown as a separate component by way of example only. Depending upon the type of memory device used as the removable memory 610, the computing device 650 may include a memory connector that provides a direct connection to the removable memory. For example, the removable memory 610 may be a USB Type B storage device. In such an example, the computing device 650 may include a USB Type B port that can directly connect to the removable memory 610.

Figure 7A:
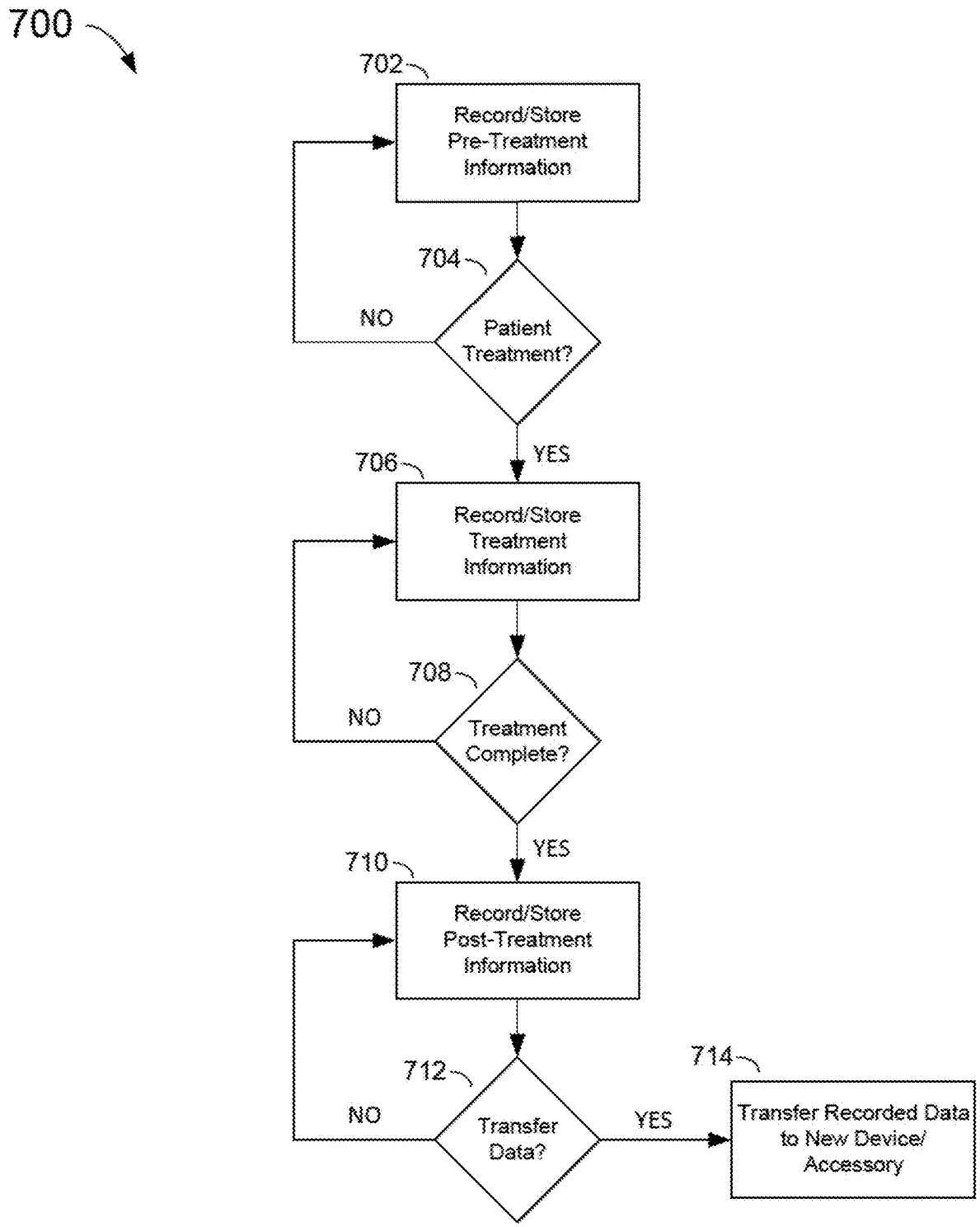
FIG. 7A is a flow diagram of illustrating a process of monitoring and recording information to a medical device accessory-based memory, in accordance with at least one example disclosed herein.

To fully utilize the patient-coupled resuscitation device or other similar accessory-based integrated memory as described herein, one or more processes can be implemented. For example, FIG. 7A illustrates a sample process 700 that provides an overview of using the accessory-based memory as described herein. As shown in FIG. 7A, one or more processing devices such as processors 502 and 602 as described above and/or processor(s) that are part of the medical device with which the accessory is connected can record 702 information collected by one or more medical device accessories prior to patient treatment. For example, the pre-treatment information can include operational information such as battery-specific information as described herein as well as medical device information (e.g., medical device identification, device type, self-test information, calibration information related to, for example, accelerometers or other similar motion sensors in the medical device, medical device status, etc.). The pre-treatment information can also include patient physiological information and patient characteristic information such as patient demographic, history, size, gender, weight information and other information that can be accessed from, for example, the patient's medical record. The processor can determine 704 whether the patient has been treated. For example, patient treatment information can document a patient receiving one or more defibrillation or other treatment shocks, receiving chest compressions, receiving breathing assistance, and other similar treatments as described herein. If the processor does not determine 704 that the patient has received treatment, the processor can continue to record 702 the pre-treatment information.

Though, if the processor does determine 704 that the patient has received treatment, the processor can record 706 treatment information by, for example, storing the above identified patient treatment information. For example, the treatment information can include whether a defibrillation shock was delivered to the patient and specific information about the shock (e.g., what energy level, what the patient's presenting ECG rhythm was that instigated the particular type of treatment). The treatment information can also include chest compression information such as compression rate and depth information and/or release information, as well as breathing assistance information such as air flow rate information as described herein.

The processor can then determine 708 if the treatment is complete. If the processor determines 708 that the treatment is not complete, the processor can continue to record 706 the treatment information. If the processor does determine 708 that the treatment is complete, the processor can then record 710 any post-treatment information. For example, the post-treatment information can include updated operational information such as battery-specific information as described herein as well as medical device information. The post-treatment information can also include updated patient physiological information measured following completion of the patient's treatment.

In certain implementations, the processor can determine 712 whether there is a request to transfer the recorded information. For example, if the patient-coupled resuscitation device or other similar accessory is operably coupled to a new medical device, the new medical device can automatically request a transfer of the recorded information as described herein. If the processor does not determine 712 a request for a transfer of information, the processor can continue to record 710 post-treatment information. If the processor does determine 712 a request for a transfer of data, the processor can transfer 714 at least a portion of the recorded data to the requesting device.

Figure 7B:
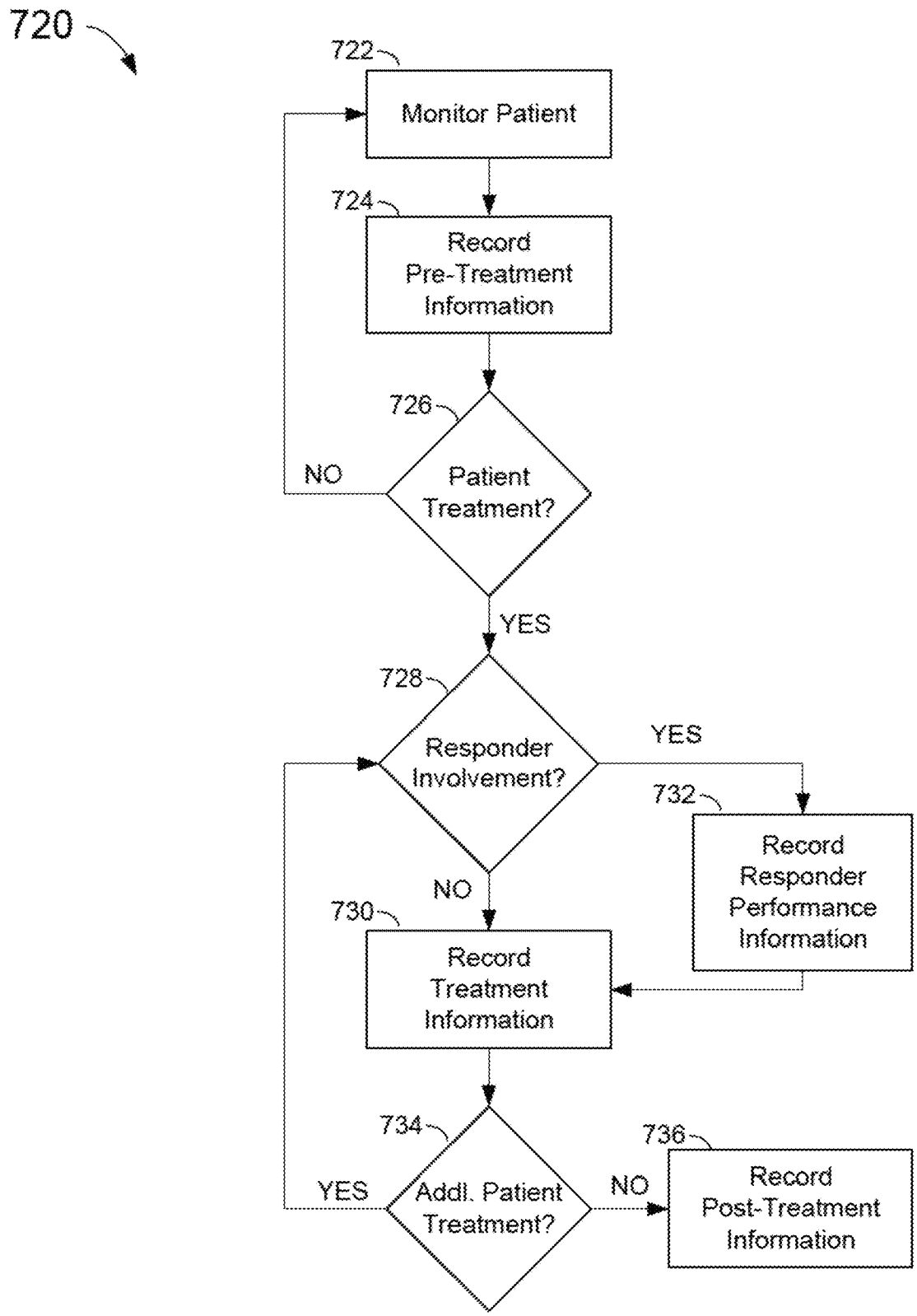
FIG. 7B is a more detailed flow diagram of the process of monitoring for recording information to a medical device accessory-based memory, in accordance with at least one example disclosed herein.

FIGS. 7B and 7C provide more detailed process flows for various portions of the process 700. For example, FIG. 7B illustrates process 720 which includes a more detailed process flow for monitoring a patient and recording information prior to, during, and post treatment. FIG. 7C illustrates process 740 which includes a more detailed process flow for transferring recorded data to another device.

Referring now to FIG. 7B, the process 720 includes a more detailed process flow for monitoring a patient and recording information related to the patient prior to, during, and after treatment by a medical device that includes a patient-coupled resuscitation device or other similar accessory having an integrated memory as described herein. For example, as shown in FIG. 7B, a processor such as processors 502 and 602 as described above and/or processor(s) that are part of the medical device with which the patient-coupled resuscitation device or other similar accessory is connected can monitor 722 a patient. For example, the processor can access information collected by one or more sensors such as sensors 504 and 604 as described above to determine current information about the patient such as patient physiological information. The processor can record 724 this pre-treatment patient information, as well as additional information such as medical device operational information as described herein, to the integrated memory.

While monitoring 722 and recording 724, the processor can further determine 726 whether the patient is receiving any treatment. If the processor determines 726 that the patient is not receiving treatment, the processor can continue to monitor 722 the patient and to record 724 pre-treatment information. If the processor does determine 726 that the patient is receiving treatment, the processor can determine 728 additional information about the treatment such as whether the treatment requires responder involvement. For example, if the patient is receiving CPR, the processor can determine 728 that the treatment does require responder involvement. Conversely, if the patient is receiving a defibrillation shock, the processor may determine 728 that the responder involvement is minimal or altogether absent.

If the processor determines 728 that there is no responder involvement, the processor can record 730 information related to the treatment as described herein. However, if the processor does determine 728 that there is responder involvement in the treatment, the processor can also record 732 responder performance information as well as record 730 the treatment information. For example, if the patient is receiving CPR, the responder performance information can include chest compression rate information, average chest compression depth, maximum chest compression depth, minimum chest compression depth, release velocity, CPR fraction (e.g., percentage of time that CPR is actually being given to the patient during periods designated for CPR), percentage of compression depth and rate that are within target ranges, and other similar responder performance metrics.

Upon recording 730 the treatment information, the processor can determine 734 if the patient is being given additional treatment. If the processor determines 734 that the patient is being given additional treatment, the processor can again determine 728 whether there is responder involvement and can record 732 the responder performance information and record 730 the treatment information as noted above. If the processor determines 734 that the patient is not receiving any additional treatment, the processor can record 736 any post-treatment information as described herein.

FIG. 7C illustrates process 740 which includes a more detailed process flow for transferring information in response to a request for stored information. As shown in FIG. 7C, a processor such as processors 502 and 602 as described above and/or processor(s) that are part of the medical device with which the patient-coupled resuscitation device or other similar accessory is connected, can establish 742 a connection with another device such as a medical device or a computing device as described above. The processor can monitor 744 the connection and determine 746 whether a request for stored information has been received from the connected device. If the processor determines 746 that no request has been received, the processor can continue to monitor 744 the connection. If the processor does determine 746 that a request for stored information has been received, the processor can determine 748 what information has been requested. The processor can then access 750 the requested information from the accessory-based memory and transfer 752 the requested information to the requesting device.

It should be noted that the processes as shown in FIGS. 7A-7C are provided by way of example only and can be modified based upon the teachings of the accessory-based memory techniques as described herein. For example, process 720 as shown in FIG. 7B can be altered to remove determination of the responder involvement if the accessory-based memory is not configured to store such information or if the accessory is designed to operate without responder intervention. Additionally, in certain implementations, process 740 can include encrypting the requested information prior to transferring to the requesting device.

Sample Data Structures

As noted above, a patient-coupled resuscitation device or other similar accessory such as a set of sensing and therapy electrodes can include an integrated non-volatile memory that is configured to store information related to the operation or use of the accessory. For example, with a set of sensing and therapy electrodes as described herein, the memory can be configured to store information measured by and related to the operation of the set of sensing and therapy electrodes. FIG. 8A illustrates a sample overview of an electrode information data structure 800, which may allow for efficient recording, storage, and retrieval of information. As shown in FIG. 8A, the data structure 800 can include various categories of fields such as data identifier fields 805 and data fields 810. Each of the categories of fields can have various fields nested therein. For example, data identifier fields 805 can include a patient ID field 805a, a pre-treatment heartrate field 805b, a pre-treatment blood pressure field 805c, a treatable arrhythmia field 805d, a treatment shock provided field 805e, a number of treatment shocks field 805f, a first treatment shock information field 805g, a second treatment shock information field 805h, a post-treatment heartrate field 805i, and a post-treatment blood pressure field 805j. While data structures described herein may include static fields that provide particular values for certain categories, data structures may also include dynamic fields, where larger feeds of data such as physiological waveforms and other streams of data are recorded over continuous period of time. As further shown in FIG. 8A, each individual data identifier field 805 can have a corresponding data field 810 that includes additional information related to the identified piece of data. For example, ID number field 810a can include a patient identification number such as the patient's social security number, patient record number, insurance information number, and/or other similar identification that can be used to identify the patient being treated. As shown in FIG. 8A, data field 810b can include the patient's pre-treatment heart rate information, and data field 810c can include the patient's pre-treatment blood pressure information. As further shown in FIG. 8A, data field 810d can provide an indication of whether the patient's arrhythmia was treatable, data field 810e can provide an indication as to whether at least one treatment shock was provided to the patient, and data field 810f can provide an indication of how many treatment shocks were provided to the patient. As further shown in FIG. 8A, data field 810g can provide information related to the first treatment shock such as energy delivered and whether the first treatment shock was successful, data field 810h can provide information related to the second treatment shock such as energy delivered and whether the second treatment shock was successful, data field 810i can provide an indication of the patient's post-treatment heart rate, and data field 810j can provide an indication of the patient's post-treatment blood pressure.

It should be noted that the information as shown in data structure 800 as illustrated in FIG. 8A is provided by way of example only. In practice, the data identifier fields 805 as contained within the data structure 800 can include additional information or remove information as shown in FIG. 8A. For example, additional data identifier fields showing device identification information such as device serial number, device capability, and device type can be included. In some examples, treatment shock timing information can be provided such as how long after arrhythmia detection was the first shock delivered, and how long after the first treatment shock was the second treatment shock delivered. It should also be noted that two treatment shocks are shown by way of example only. Similarly, the energy delivered values as shown in data fields 810g and 810h are provided by way of example only.

Depending upon the type of patient-coupled resuscitation device or other similar accessory used, additional data structures can be used to store information related to the operation or use of the accessory. For example, FIG. 8B illustrates a sample chest compression information data structure 820 configured to store information collected from a chest compression sensor as described herein. As shown in FIG. 8B, the data structure 820 can include various categories of fields such as data identifier fields 825 and data fields 830. Each of the categories of fields can have various fields nested therein. For example, data identifier fields 825 can include a patient ID field 825a, a CPR administered field 825b, an average compression rate field 825c, an average compression depth field 825d, a maximum compression depth field 825e, a minimum compression depth field 825f, a chest compression fraction field 825g, a percentage of chest compressions that are within a target depth field 825h, an average release velocity field 825i, and an average pre-shock/post-shock pause field 825j. Or, in some embodiments, the data identifier fields or data structures may store the raw data associated with one or more of the parameters described herein, and the actual calculations for such parameters may be performed by a processor external to the accessory, such as a processor on a separate computing device, mobile device, and/or server.

As further shown in FIG. 8B, each individual data identifier field 825 can have a corresponding data field 830 that includes additional information related to the identified piece of data. For example, ID number field 830a can include a patient identification number such as the patient's social security number, patient record number, insurance information number, and/or other similar identification that can be used to identify the patient being treated. As shown in FIG. 8B, data field 830b can include an indication of whether CPR was administered to the patent, data field 830c can include a calculated average compression rate, data field 830d can include a calculated average compression depth, data field 830e can include a measured maximum compression depth, data field 830f can include a measured minimum compression depth, data field 830g can include a calculated chest compression fraction, data field 830h can include a percentage of chest compressions that were within a target range, data field 830i can include an average release velocity measurement, and data field 830j can include average pre-shock and post-shock pause measurements. In some examples, the data structure 820 can include additional information such as device identification information including, for example, device serial number, device capability, and device type.

In another example, FIG. 8C illustrates a sample airflow sensor information data structure 840 configured to store information collected from an airflow sensor as described herein. As shown in FIG. 8C, the data structure 840 can include various categories of fields such as identifier fields 845 and data fields 850. Each of the categories of fields can have various fields nested herein. For example, data identifier fields 845 can include a patient ID field 845*a*, a breathing assistance administered field 845*b*, a pre-treatment respiration rate field 845*c*, a post-treatment respiration field 845*d*, a pre-treatment end-tidal CO2 field 845*e*, a post-treatment end-tidal CO2 field 845*f*, average tidal volume 845*g*, average minute volume 845*h*, percentage of ventilations that are within a target range 845*i*, and device ID 845*j*.

As further shown in FIG. 8C, each individual data identifier field 845 can have a corresponding data field 850 that includes additional information related to the identified piece of data. For example, ID number field 850*a* can include a patient identification number such as the patient's social security number, patient record number, insurance information number, and/or other similar identification that can be used to identify the patient being treated. As shown in FIG. 8C, data field 850*b* can include an indication of whether breathing assistance was administered to the patent, data field 850*c* can include a measured pre-treatment respiration rate, data field 850*d* can include a measured post-treatment respiration rate, data field 850*e* can include a measured pre-treatment end-tidal CO2 level, and data field 850*f* can include a measured post-treatment end-tidal CO2 level. Data field 850*g* can include a measured average tidal volume 850*g*, data field 850*h* can include an average minute volume, data field 850*i* can include a percentage of ventilations that are within a target range, and data field 850*j* can include device identification information.

It should be noted that the information as shown in data structure 820 as illustrated in FIG. 8B and the information as shown in data structure 840 as illustrated in FIG. 8C is provided by way of example only. In practice, the data identifier fields 825, 845 as contained within the data structures 820, 840 can include additional information or remove information as shown in FIGS. 8B and 8C.

As noted above, a patient-coupled resuscitation device or other similar accessory can further include a battery having an integrated non-volatile memory. In certain implementations, the integrated memory of the battery can be configured to store current and historical operational information related to the battery. For example, FIG. 8D illustrates a sample battery information data structure 860 configured to store information collected from a medical device battery as described herein. As shown in FIG. 8D, the data structure 860 can include various categories of fields such as identifier fields 865 and data fields 870. Each of the categories of fields can have various fields nested herein. For example, data identifier fields 865 can include a battery ID field 865*a*, an energy level field 865*b*, a self-test information field 865*c*, a last alarm information field 865*d*, an alarm type field 865*e*, a lifetime shocks delivered field 865*f*, a shocks delivered since last charge field 865*g*, and a device ID field 865*h* including an indication of what device or devices the battery has been previously used to power.

As further shown in FIG. 8D, each individual data identifier field 865 can have a corresponding data field 870 that includes additional information related to the identified piece of data. For example, battery serial number field 870*a* can include a manufacturer assigned serial number for the battery. As shown in FIG. 8D, data field 870*b* can include a current energy level for the battery, data field 870*c* can include information related to the most recent self-test such as whether the test completed and if there were any errors as well as related calibration information such as most recent date of calibration and any functional changes made during the calibration, data field 870*d* can include information related to the last alarm the battery issued, data field 870*e* can include an indication of what type of alarm was issued, data field 870*f* can include a count of how many shocks the battery has delivered in its lifetime, data field 870*g* can include a count of how many shocks the battery has delivered since its last charge, and data field 870*h* can include one or more device ID numbers indicating what devices the battery has provided power to.

It should be noted that the information as shown in data structure 860 as illustrated in FIG. 8D is provided by way of example only. In practice, the data identifier fields 865 as contained within the data structure 860 can include additional information or remove information as shown in FIG. 8D.

It should also be noted that, in some examples above, the information contained in the data fields as shown in FIGS. 8A-8D includes calculated data. This is provided by way of example only. In some implementations, the patient-coupled resuscitation device or other similar accessory measuring the information such as a set of defibrillation electrodes may not have the processing capabilities to calculate specific information such as that shown in FIGS. 8A-8D and described above. In such implementations, the accessory can provide raw recorded data to a medical device or another processing device as described herein for calculation of the actual values as described herein.

In addition to providing static information such as that shown in FIGS. 8A-8D, a patient-coupled resuscitation device or other similar accessory can also record waveform or other similar time-based information to the accessory-based memory for, for example, transferring to another device for processing and/or analysis. For example, as shown in FIG. 8E, a set of waveforms 880 can be recorded on the memory as raw data for transferring to another device for processing. Or, such waveform data may be pre-processed before transferring to another device for further processing, recording, and/or reporting. As shown in FIG. 8E, the waveforms can include recorded ECG information, recorded CO2 waveforms, and SpO2 waveforms.

Sample User Interfaces

FIG. 9A illustrates a sample view of a user interface screen 900 that can be accessed and utilized by a physician and/or another healthcare provider to initiate a data transfer of information collected during treatment of a patient. For example, the user interface screen 900 can be used to initiate a transfer of some or all of the data as shown in data structures 800, 820, and 840 and described above in relation to FIGS. 8A-8C. A similar user interface screen can be used, for example, by a medical device manufacturer or a device technician to transfer some or all of the data as shown in data structure 860 in FIG. 8D relating to current and historical operational information for a battery including an integrated memory as described herein.

As illustrated in FIG. 9A, the user interface screen 900 includes user interface controls 910, 915, 920, 925, and 930. In some examples, the user interface control 910 provides access to patient specific information such as the cardiac patient's name and an identifier associated with the cardiac patient. In certain implementations, the patient identifier can be a medical records number associated with the cardiac patient, an insurance identification number associated with the cardiac patient, a number that directly identifies the cardiac patient such as a social security number, or another similar identification number. Based upon the patient specific information, the processor can access the patient's medical record. The user interface control 915 can include a button or other selectable control. In some examples, the processor responds to input selecting the user interface control by transferring all patient data associated with treatment of the patient and stored on a memory device to the patient's medical record.

Additionally or alternatively, the user interface control 920 can provide access to a set of available controls 920a-920d that can be used to selectively transfer only a portion of the stored information. As shown, the set of available controls can include, for example, a list of available data options as recorded during patient treatment from which the physician can select. For example, as shown in FIG. 9A, the set of controls 920a-920d includes a patient physiological data control 920a, a rescuer performance data control 920b, a treatment data control 920c, and a device operational data control 920d. The physician can select one or more of controls 920a-920d to provide an indication of what data is to be transferred to the patient's record. For example, the physician may determine that the rescuer performance data should not be transferred to the patient's record. The physician can then select controls 920a, 920c, and 920d as described herein.

Additionally or alternatively, the user interface screen 900 can provide control 925 that can be used to select an output format for the transferred information. As shown, a sample set of available output formats can include a PDF document, a text document, and a spreadsheet. The physician can select one of the options as included in control 925 to provide an indication of what format they would like the output of the transferred data to be formatted in.

As further shown in FIG. 9A, the user interface control 930 includes a set of selectable buttons. In response to receiving a selection of the "submit" button, the processor can transfer data to the patient's record as indicated or selected in controls 920a-920d. In response to receiving a selection of the "clear" button, the processor can delete existing selections and/or entered information from the user interface screen 900. In response to receiving a section of the "cancel" button, the processor can abort the data transfer process.

Figure 9B:
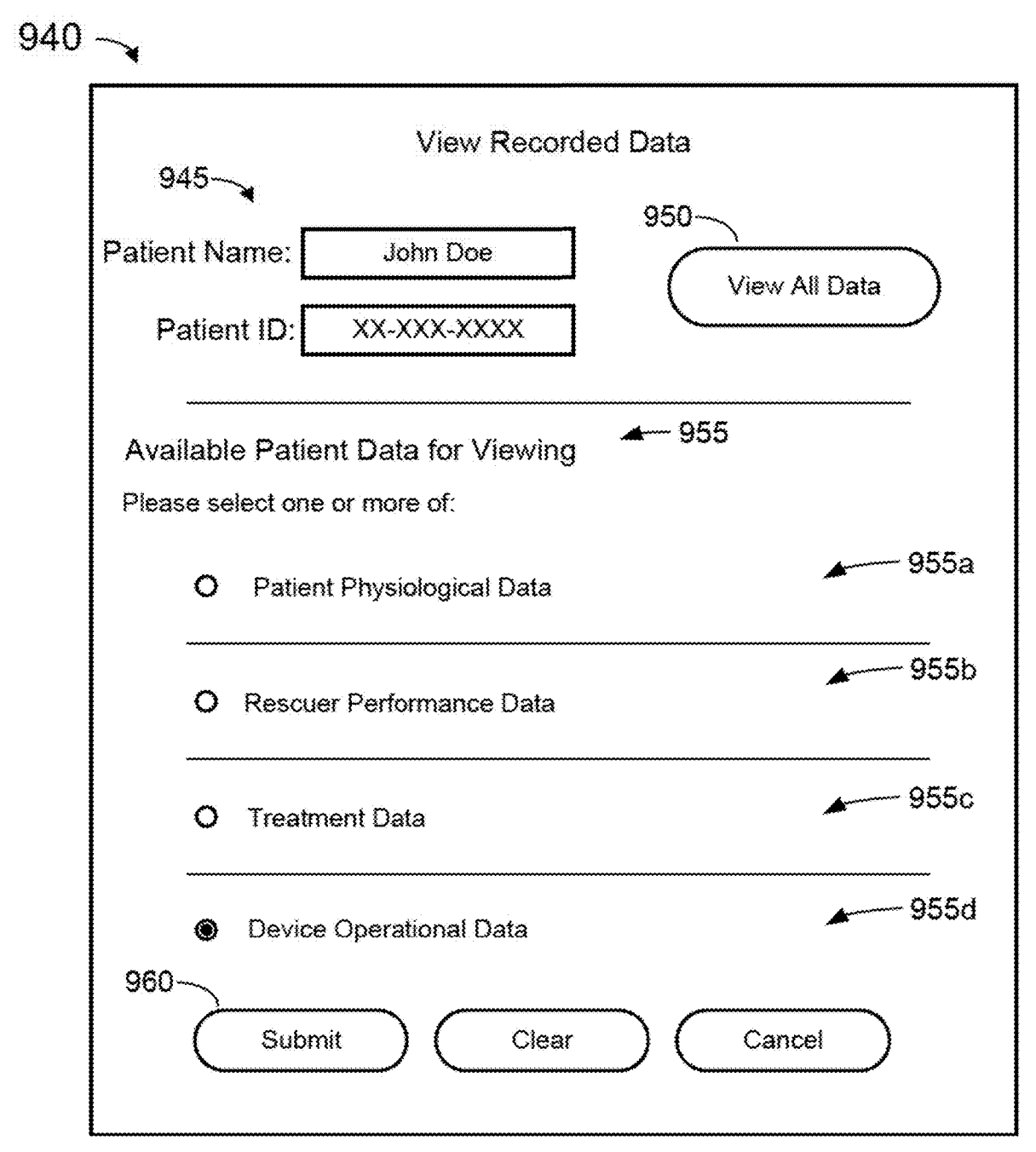

FIG. 9B illustrates a sample view of a user interface screen 940 that can be accessed and utilized by a physician and/or another healthcare provider to immediately access and view some or all of the information collected during treatment of a patient. For example, the user interface screen 940 can be used to view some or all of the data as shown in data structures 800, 820, and 840 and described above in relation to FIGS. 8A-8C. A similar user interface screen can be used, for example, by a medical device manufacturer or a device technician to view some or all of the data as shown in data structure 860 in FIG. 8D relating to current and historical operational information for a battery including an integrated memory as described herein.

As illustrated in FIG. 9B, the user interface screen 940 includes user interface controls 945, 950, 955, and 960. In some examples, the user interface control 945 provides access to patient specific information such as the cardiac patient's name and an identifier associated with the cardiac patient. In certain implementations, the patient identifier can be a medical records number associated with the cardiac patient, an insurance identification number associated with the cardiac patient, a number that directly identifies the cardiac patient such as a social security number, or another similar identification number. Based upon the patient specific information, the processor can access the portion of stored information that is related to the identified patient. The user interface control 950 can include a button or other selectable control. In some examples, the processor responds to input selecting the user interface control by providing all patient data associated with treatment of the patient and stored on a memory device for immediate viewing.

Additionally or alternatively, the user interface control 955 can provide access to a set of available controls 955a-955d that can be used to selectively view only a portion of the stored information. As shown, the set of available controls 955a-955d can include, for example, a list of available data options as recorded during patient treatment from which the physician can select. For example, as shown in FIG. 9B, the set of controls 955a-955d includes a patient physiological data control 955a, a rescuer performance data control 955b, a treatment data control 955c, and a device operational data control 955d. The physician can select one or more of controls 955a-955d to provide an indication of what data the physician would like to view. For example, the physician may determine they are not interested in the rescuer performance data. The physician can then select controls 955a, 955c, and 955d as described herein for immediate viewing.

As further shown in FIG. 9B, the user interface control 960 includes a set of selectable buttons. In response to receiving a selection of the "submit" button, the processor can access and display the information as indicated or selected in controls 955a-955d. In response to receiving a selection of the "clear" button, the processor can delete existing selections and/or entered information from the user interface screen 940. In response to receiving a section of the "cancel" button, the processor can abort the data viewing process.

It should be noted that the user interface screens 900 and 940 as shown in FIGS. 9A and 9B are provided by way of example only and can be modified based upon the design and intended functionality of the information accessing system. For example, user interface screen 900 can further include a control that provides the physician with an option to select a download location for a file transfer. Similarly, user interface screen 940 can include a control that provides the physician with an option to select how to view the information.

Chest Compression Sensor Embodiments

A variety of chest compression sensors can be used in conjunction with the examples described herein. For instance, in some examples, chest compression sensors that are distinct from other medical equipment are provided. In these examples, to decrease the amount of time required to utilize the chest compression sensor in the administration of life-saving CPR, some of the chest compression sensors are configured to automatically initiate operation as needed.

Figure 10A:
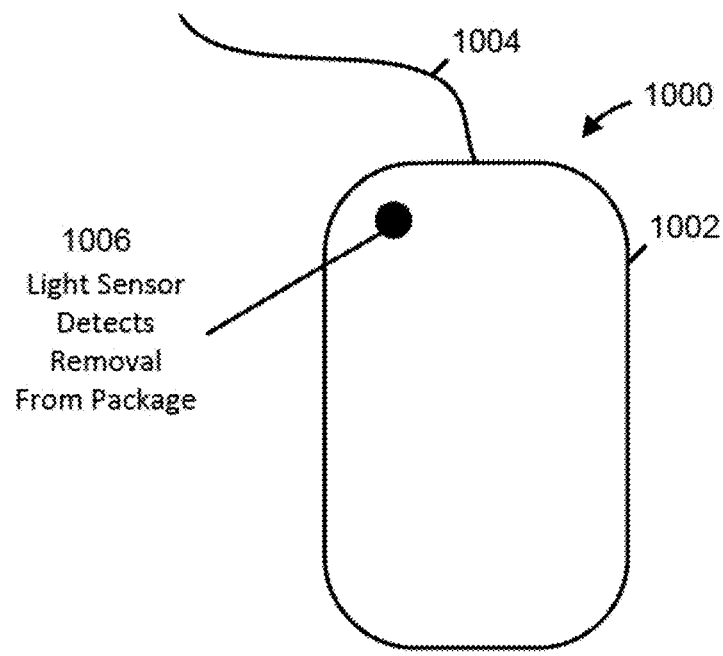
FIGS. 10A and 10B are schematic diagrams of sample chest compression sensors, in accordance with at least one example disclosed herein.

FIG. 10A illustrates one example of such a chest compression sensor, the compression sensor 1000. As shown in FIG. 10A, the compression sensor 1000 includes a housing 1002, a connector 1004, and a photoelectric sensor 1006. The connector 1004 can include a pigtail style connector and can transport power and data for use by the other components of the compression sensor 1000. In some examples, the photoelectric sensor 1006 can detect ambient light and can transmit a detection signal where the ambient light transgresses a threshold value (e.g., 1000 lux). In some examples, the compression sensor 1000 includes additional circuitry (e.g., a microcontroller or other processor) that is coupled to the photoelectric sensor 1006. The additional circuitry can be configured to monitor an output of the photoelectric sensor 1006 for the detection signal. In these examples, the additional circuitry is further configured to initiate powered operation of the compression sensor 1000 in response to receiving the detection signal.

Figure 10B:
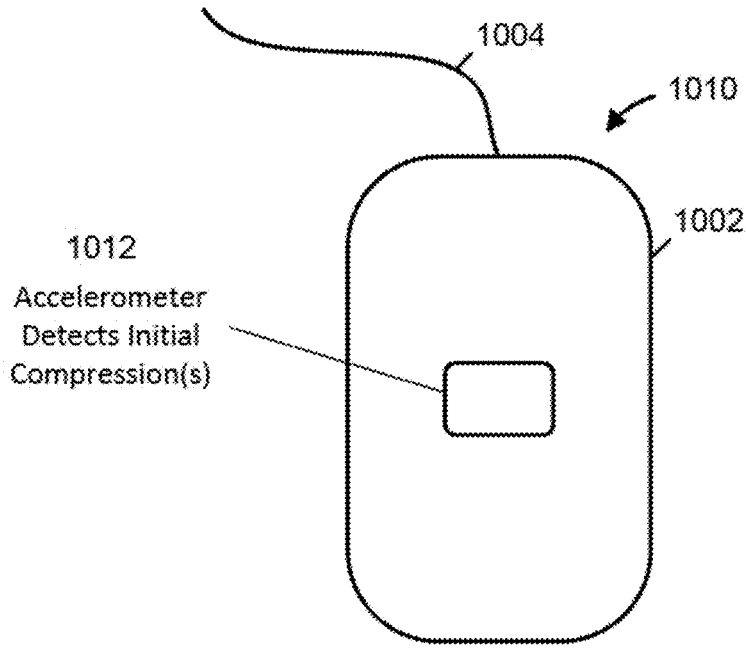

FIG. 10B illustrates another example chest compression sensor 1010 in accordance with some examples. As shown in FIG. 10B, like the compression sensor 1000, the compression sensor 1010 includes a housing 1002 and a connector 1004. The compression sensor 1010 further includes a low-power or self-powered accelerometer 1012. In some examples, the accelerometer 1012 can detect movement and can transmit a detection signal where the movement transgresses a threshold value (e.g., movement sufficient to administer a CPR compression). In certain implementations, the accelerometer 1012 can be calibrated to configure the output resolution of the accelerometer to accurately translate an output voltage of the detection signal of the accelerometer to motion information. The calibration can include applying a known force to the accelerometer 1012 and adjusting the output voltage of the detection signal to an expected result. Calibration information such as the date of the calibration and changes applied to the output voltage of the detection signal can be recorded as medical device information as described herein.

In some examples, the compression sensor 1010 includes additional circuitry (e.g., a microcontroller or other processor) that is coupled to the accelerometer 1012. This additional circuitry is configured to monitor an output of the accelerometer 1012 for the detection signal. In these examples, the additional circuitry is further configured to initiate powered operation of the compression sensor 1000 in response to receiving the detection signal. Other examples are provided herein of a chest compression sensor that initiates compression sensing upon actuation of a switch or when a sufficient amount of force is detected. In some embodiments, the chest compression sensor may include a capacitive force sensor that initiates operation of the compression sensing functionality upon reaching a threshold force (e.g., between 440 and 560 Newtons) such as when the sensor is first subject to compressions. Or, the sensor may include a plastic tab over a battery such that when the tab is pulled, the sensor becomes ready for operation. In other embodiments, the chest compression sensor may include a hall sensor and nearby magnet located within the casing that triggers compression sensing once the hall sensor detects disconnection from the magnet. Another embodiment may employ a plastic tab designed to break upon first compression or a membrane switch triggers compression sensing in the device when pushed.

To be effective, CPR should begin within a very short period of time (e.g., 1-5 minutes) after the onset of cardiac arrest. This requirement can make it difficult to identify and use a defibrillator/monitor in sufficient time so as to provide CPR feedback for the caregiver. In addition, such cardiac arrests are oftentimes respiratory in nature, not requiring defibrillation electrodes. Due at least in part to these factors, devices described herein that provide monitoring of CPR metrics, including a standalone chest compression sensor, may be able to record immediately upon start of CPR without requiting a device to be in the vicinity. Hence, in accordance with embodiments provided herein, the chest compression sensor may itself have measurement, processing, and storage capabilities. Also described herein, the standalone sensor may include a basic level of output feedback, such that a nearby screen is not required. This could be an LCD/E-Ink screen, a set of LED lights, a vibration actuator, and/or a speaker integrated with the chest compression sensor device. Although it can be appreciated that the standalone chest compression sensor may be able to connect to a companion screen in the form of a tablet, display, medical device interface and/or other mode of feedback.

Neo-natal CPR possess special challenges to caregivers due to the diminutive anatomy of the patients. Further, these patients have fragile and sensitive skin, which often makes it undesirable to attach adhesive or abrasive materials typically found in traditional monitoring equipment that could bring harm to their skin. Accordingly, traditional chest compression sensors which come with a defibrillator/monitor that are intended for use with adults present difficulties in providing effective chest compressions to the patient. As such, some examples described herein provide for chest compression sensors designed to overcome these challenges.

Figure 11A:
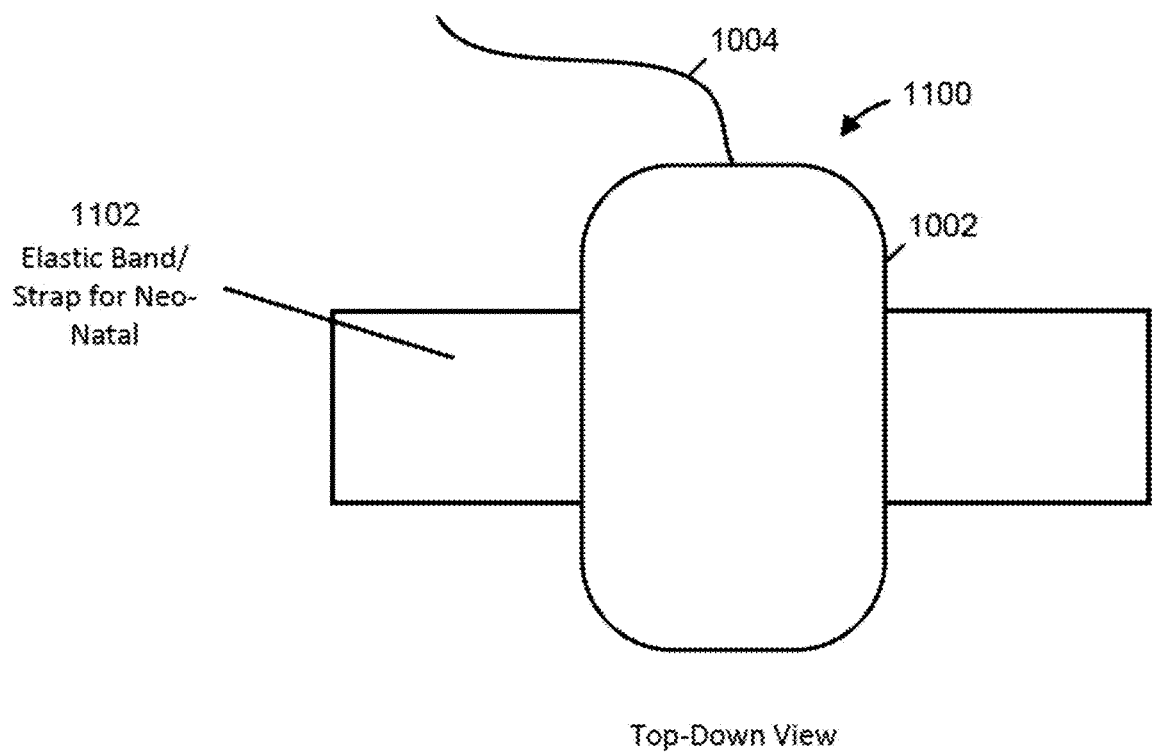
FIG. 11A is a schematic diagram of a sample neo-natal chest compression sensor including a band, in accordance with at least one example disclosed herein.
Figure 11A:
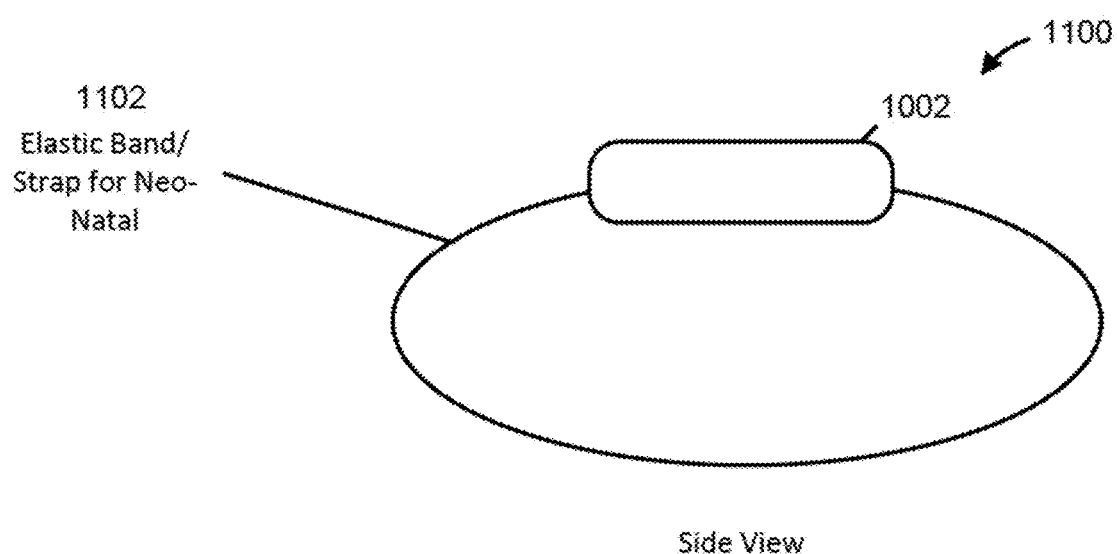

FIG. 11A illustrates one example of a chest compression sensor 1100 that includes features configured to provide better CPR treatment to neo-natal patients. As shown in FIG. 11A, the compression sensor 1100, like the compression sensor 1000, includes a housing 1002 and a connector 1004. The compression sensor 1100 further includes an elastic band 1102 that is configured to expand while being fitted to a patient and then contract to provide a snug fit with minimal lateral movement. For instance, in some examples, the elastic band 1102 is sized to have a resting diameter of approximately 2-5 inches. In this way, the compression sensor 1100 more easily and reliably remains in its fitted location, thereby providing for more accurate CPR readings. Accuracy of CPR performance, such as proper compression depth, is particularly important when dealing with neo-natal patients.

Figure 11B:
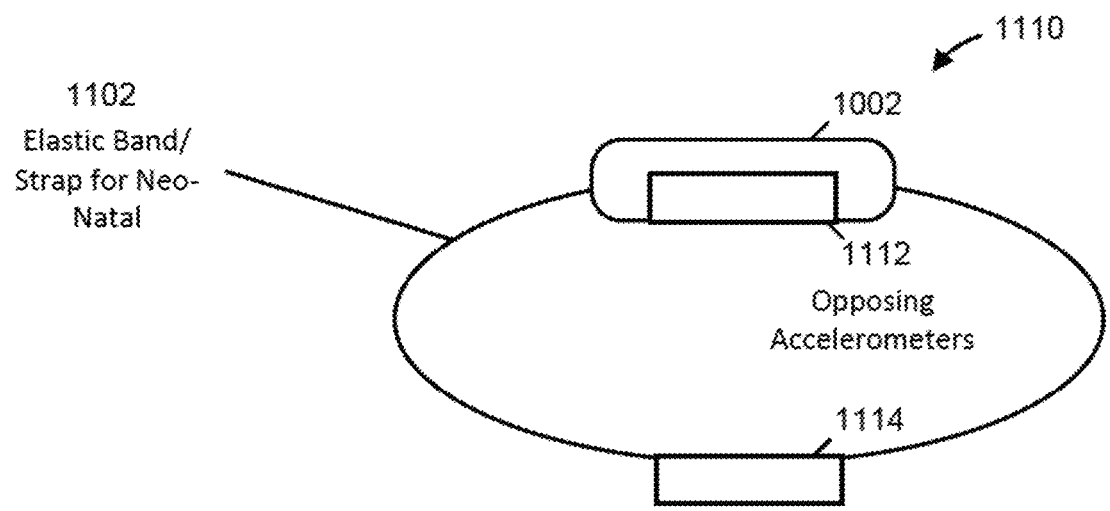
FIG. 11B is a schematic diagram of a sample neo-natal chest compression sensor including opposing sensors, in accordance with at least one example disclosed herein.

FIG. 11B illustrates one example of a chest compression sensor 1110 that includes additional features configured to provide better CPR treatment to neo-natal patients. As shown in FIG. 11B, the compression sensor 1110, like the compression sensor 1100, includes a housing 1002 and an elastic band 1102. The compression sensor 1110 further includes opposing accelerometers 1112 and 1114 that are configured to detect movement toward and away from one another. In some examples, the compression sensor 1110 includes additional circuitry (e.g., a microcontroller or other processor) that is coupled to the opposing accelerometers 1112 and 1114. This additional circuitry is configured to monitor outputs of the opposing accelerometer 1112 and 1114 for the motion signals. By processing motion signals sourced from anterior and posterior locations on the patient, the additional circuitry can generate more precise and accurate CPR readings, which are of particular importance to neo-natal patients. For example, when performing neo-natal CPR, it is often the case that the thumbs of the caregiver are positioned on the anterior chest of the patient and the fingers of the caregiver are positioned on the posterior of the patient. By having motion sensors at both the anterior and posterior regions of the patient, a more accurate determination of chest compression depth can be made.

Figure 12A:
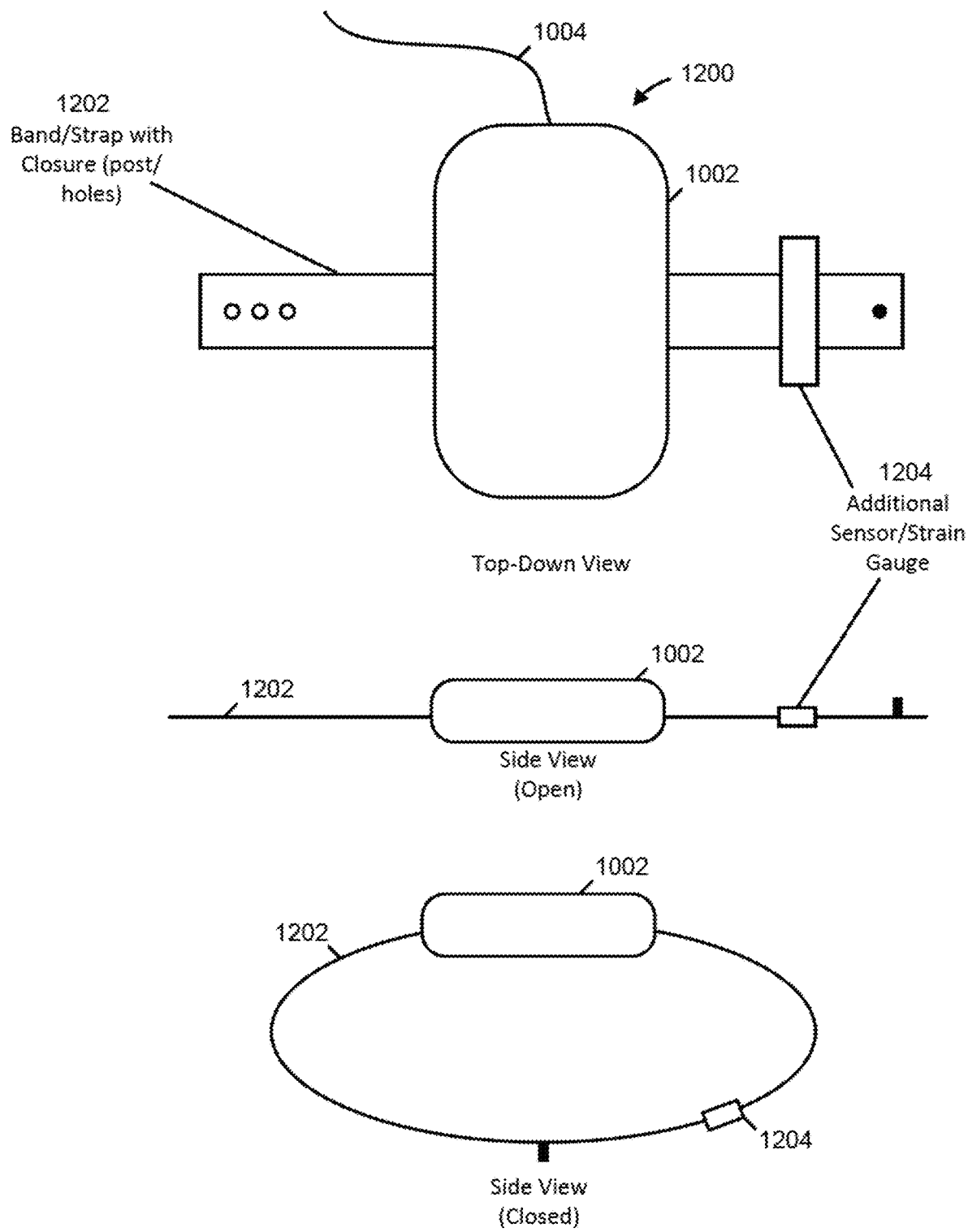
FIGS. 12A-12C are schematic diagrams of alternate closure assemblies for a sample neo-natal chest compression sensor, in accordance with at least one example disclosed herein.
Figure 12B:
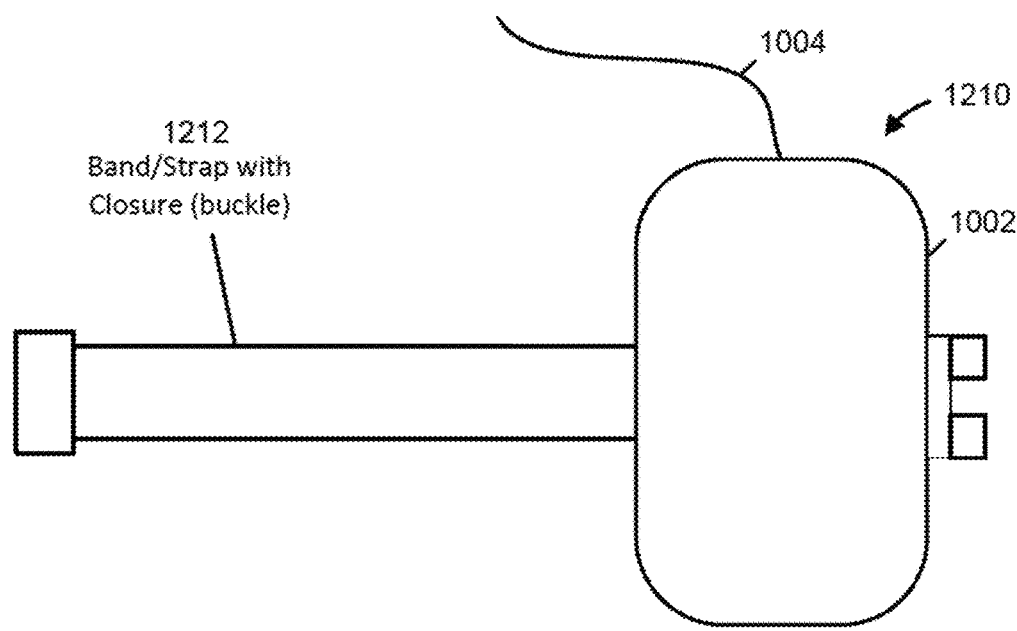
Figure 12C:
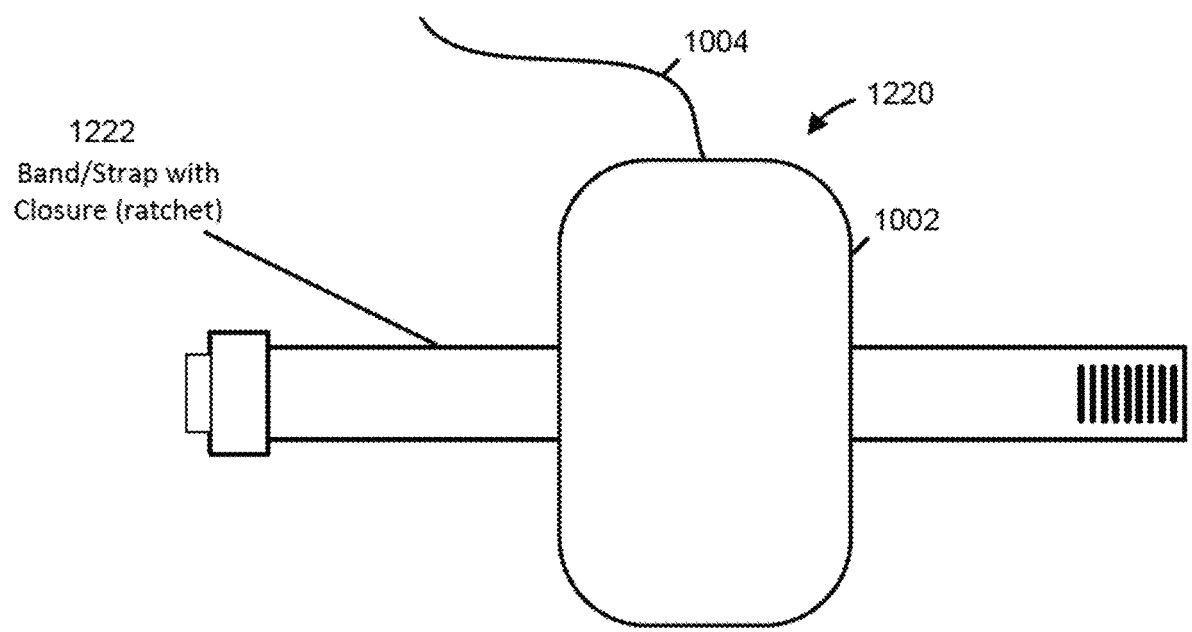

FIG. 12A illustrates one example of a chest compression sensor 1200 that includes additional features configured to provide better CPR treatment to neo-natal patients. As shown in FIG. 12A, the compression sensor 1200, like the compression sensor 1000, includes a housing 1002 and a connector 1004. The compression sensor 1200 further includes a strap 1202 and a strain gauge 1204. The strap 1202 forms a series of apertures that are sized and shaped to receive a post on a distal portion of the strap 1202. In this way, the strap 1202 provides for the compression sensor 1200 to be snugly fitted to the thorax of variously sized patients, including neo-natal patients. The strain gauge 1204 can detect deformation of the strap 1202 and can transmit a signal indicative of the deformation. In some examples, the compression sensor 1200 includes additional circuitry (e.g., a microcontroller or other processor) that is coupled to the strain gauge 1204. This additional circuitry is configured to monitor outputs of the strain gauge for the deformation signals. By processing deformation signals, the additional circuitry can generate more precise and accurate CPR readings, which are of particular importance to neo-natal patients. In certain implementations, a calibration curve may be used to correlate the diameter of the strap with the amount of strain on the strap, making it possible to monitor patient circumference and estimate absolute chest depth of compression and chest deformation that may occur from chest remodeling/deformation that occurs during compressions. FIGS. 12B and 12C illustrate two examples of chest compression sensors 1210 and 1220 that includes additional features configured to provide better CPR treatment to neo-natal patients. As shown in FIG. 12B, the compression sensor 1210, like the compression sensor 1000, includes a housing 1002 and a connector 1004. The compression sensor 1210 includes a strap 1212 that includes a buckle closure. The buckle closure can include a receptacle 1213 and an insert 1214. As shown in FIG. 12B, the insert 1214 is positioned adjacent to the compression sensor housing 1002. Such an arrangement allows for a CPR administrator to position the compression sensor 1210 properly on the patient's sternum while buckling the strap 1212. Thus, a need to adjust the position of the compression sensor 1210 once affixed to the patient's thorax is reduced, thereby reducing the overall time required before CPR can be administered to the patient.

As shown in FIG. 12C, the compression sensor 1220, like the compression sensor 1000, includes a housing 1002 and a connector 1004. The compression sensor 1220 further includes a strap 1222. The strap 1222 includes a ratchet closure for affixing the compression sensor 1220 to a neo-natal patient. In some examples, the rachet closure can include measurement indicators that enable a CPR administrator to easily measure the circumference of the neo-natal patient's thorax, which can be helpful in diagnosing certain conditions.

It should be noted that the adjustable closures as shown in FIGS. 12A-12C are provided by way of example only, and additional adjustable closures can be used. For example, a slidable connector, a hook-and-loop connector, and other similar adjustable connectors can be included on the straps as described above to provide for an adjustable fit for a compression sensor.

Use-Case Examples

In an example, a cardiac patient may experience an arrhythmia while walking through a public space such as a shopping mall. Upon noticing the patient experiencing the arrhythmia, a bystander can step in as a first responder. The first responder can access an AED that is mounted on the wall nearby and open the therapy pad attached to the AED. The first responder can remove the patient's shirt and position the therapy pad on the patient's chest, following the instructions as printed on the pad. The first responder can then activate the AED. The AED may issue an alert including a verbal warning that the AED is monitoring the patient and may provide treatment. The AED may also provide an indication that the patient is not experiencing an arrhythmia that is treatable with a therapy shock and that the patient should be administered CPR. The first responder, or another bystander that is trained in CPR, may begin to administer CPR to the patient. After some time, the patient may improve or continue to deteriorate. If the patient continues to deteriorate, the AED may determine that the patient can now be treated with a defibrillation shock and issue warning as such. The AED may then deliver the shock to the patient via the therapy pad. During monitoring and treatment of the patient, an integrated memory in the therapy pad is recording pre-treatment information, treatment information, and post-treatment information as described herein.

At some point in the above example, trained medical responders arrive on the scene and take over treatment of the patient. The trained medical responders can disconnect the therapy pad from the AED and connect to a defibrillation device they brought. The information stored in the memory of the therapy pad can be automatically loaded onto the new defibrillation device which can continue treatment in line with the prior treatment delivered by the AED.

To continue the above example, the trained emergency responders can transfer the patient to the hospital, continuing to provide treatment to the patient on the way to the hospital. Upon arrival at the hospital, the patient may be disconnected from any portable equipment brought by the emergency medical responders and connected to hospital equipment. In such an example, a removable memory such as a battery having an integrated memory or a removable memory device as described herein can be removed from the trained emergency responder's equipment and transferred to the hospital equipment. Similar to above, the hospital equipment can access patient and treatment information for the patient and continue an appropriate course of treatment for the patient.

In another example, a removable memory associated with a medical device carried by a trained emergency responder can be accessed to evaluate the performance of the responder. For example, data collected by a chest compression sensor can be accessed and evaluated to determine how efficiently and effectively the responder is performing CPR on patients.

In another example, a physician may wish to analyze patient data from immediately before the patient was treated for an arrhythmia. The physician can access a removable memory from, for example, a therapy pad that includes physiological information for the patient as collected immediately prior to treatment of the patient. As described herein, the physician can access the information and review information such as ECG metrics for the patient immediately before the patient was treated.

Example Medical System Overviews

Figure 13A:
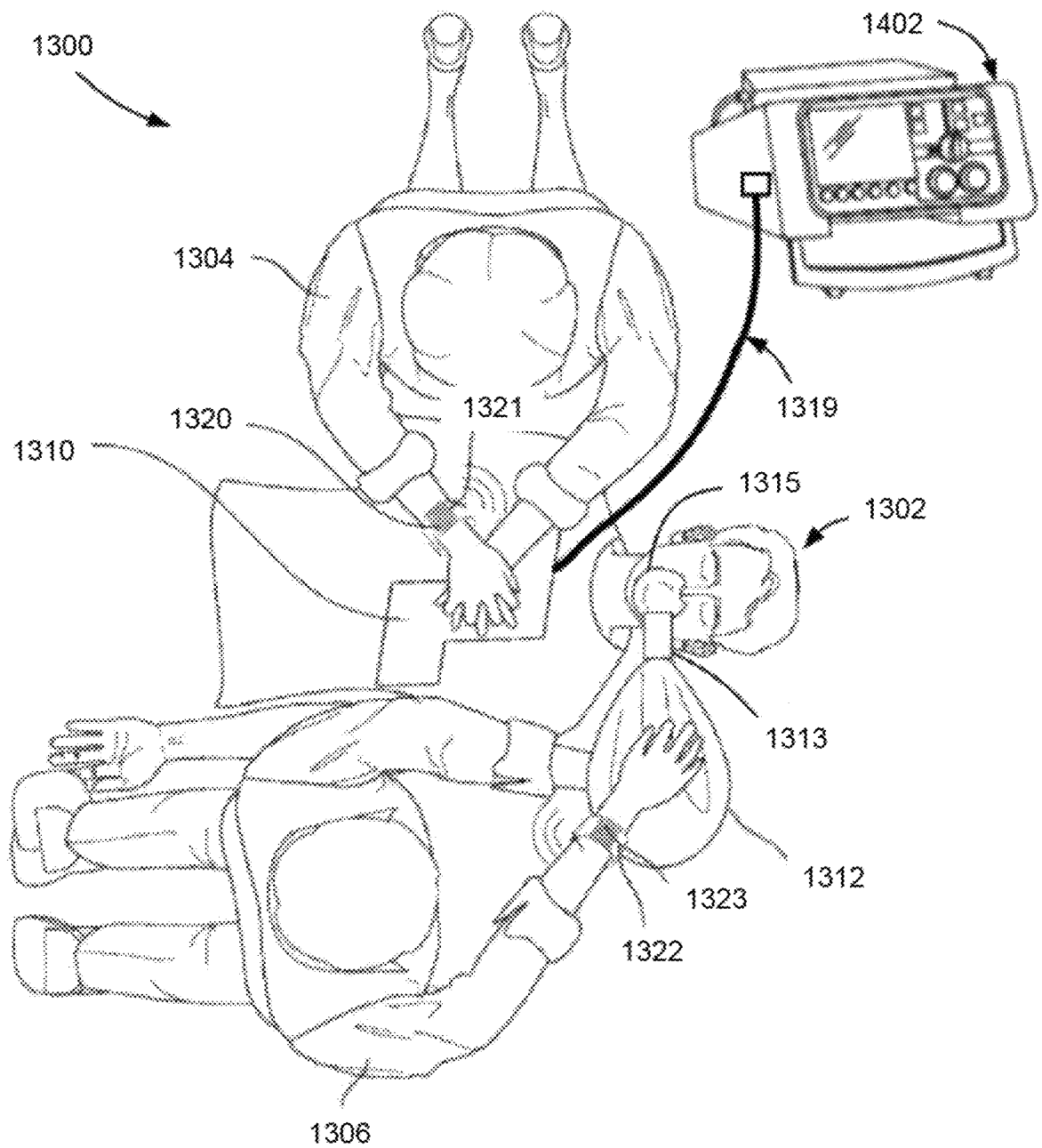
FIG. 13A is a schematic diagram of an example medical system, in accordance with at least one example disclosed herein.

FIG. 13A is a schematic illustration of an example of a patient management and treatment system 1300, including a medical device 1402 (e.g., patient monitoring device such as an automated external defibrillator or professional style monitor/defibrillator as described herein), electrode assembly 1310, and rescuers 1304, 1306 providing medical treatment to a patient 1302. While several embodiments presented herein describe the medical device 1402 as implementing the processor(s) for analyzing data from the sensor(s), determining next steps in the treatment procedure, and providing output via a user interface, it can be appreciated that other portable computing devices such as a tablet or other computing device can perform steps in accordance with the present disclosure. Additionally, the portable computing devices can be used in conjunction with medical device 1402.

In this example, rescuers 1304, 1306 are in position and providing care to the patient 1302, with rescuer 1304 providing chest compressions to the torso of the patient 1302, and rescuer 1306 providing ventilation using ventilation bag 1312, which is connected to a ventilation valve 1313 and a mask 1315. As noted above, these components (1312, 1313, 1315) are often collectively referred to as a bag-valve-mask (BVM). While not illustrated, the BVM is often connected to a source of "medical oxygen," which is used as an oxygen supply to the bag 1312, so that oxygen can be delivered during ventilation.

Generally, the rescuers 1304, 1306 can be lay-rescuers who were near the patient 1302 when the patient required care, or may be trained medical personnel such as doctors, firefighters, paramedics, combat medics, or emergency medical technicians, for example. Although two rescuers 1304, 1306 are illustrated, in alternative embodiments additional rescuers (not shown) may also be involved in treating the patient or only one rescuer may provide treatment. As used hereinafter, the term rescuer may generally be understood to include a person that is aiding in acute care treatment of the patient 1302 during an emergency medical situation and may be actively engaged in resuscitation activity of the patient, such as in providing cardiopulmonary resuscitation. Additionally, similar terms such as clinician, user, or caregiver are generally understood to be interchangeable when used herein to describe a person giving acute medical and/or resuscitative aid to the patient.

Additionally, while the present system is described with respect to a BVM and manual ventilations, a portable automatic ventilator could be used to provide oxygen and ventilate the patient. The EMV+® or Z Vent™, both manufactured by ZOLL Medical Corporation of Chelmsford, Mass. are examples of portable ventilators. Likewise, the rescue scenario may occur in a hospital or ambulance where an automatic ventilator may also be available (e.g., ZOLL 731 Ventilators provided by ZOLL Medical Corporation).

Control and coordination for the medical event is typically controlled by the medical device 1402. In a typical implementation, the medical device 1402 is a defibrillator, automated external defibrillator (AED), ventilator system, or medical patient monitor, to list a few examples. Alternatively, the medical device 1402 could even be mobile computing device such as a tablet-based computer, smartphone, or wearable computing and interface device (e.g., smart watch or head mounted optical display) that is controlled by the rescuers 1304, 1306, for example, in coordinating resuscitation activities, evaluating or otherwise communicating with on-site and/or remote medical personnel, or otherwise providing information useful for the rescuer(s) in treating the patient.

The medical device 1402 is connected to an electrode assembly 1310 via a wired connection 1319 from the medical device to the electrode assembly 1310. In this implementation, the medical device (e.g., defibrillator, or patient monitor) can take a generally common form, and may be a professional style defibrillator which can also function as a medical monitor, such as the R-SERIES®, X-SERIES®, M-SERIES®, or E-SERIES® provided by ZOLL Medical Corporation of Chelmsford, Mass., a ventilator (e.g., portable ventilator), such as the 731 Ventilator provided by ZOLL Medical Corporation, or an automated external defibrillator (AED), such as the AED PLUS®, or AED PRO® provided by ZOLL Medical Corporation.

In addition, the medical device 1402 could take the form of an integrated system of devices (defibrillator, vital signs monitor, ventilator, or mechanical CPR chest compression device, for example) with either a composite, single-system embodiment or one that uses a series of discrete devices that are dynamically integrated through wired and/or wireless communication to function as a single integrated system.

This optionally wired connection 1319 enables data from sensors in the electrode assembly to transmit information to the medical device 1402, and the wired connection 1319 also allows energy to be sent from the medical device 1402 to the electrode assembly 1310, in scenarios in which the medical device is a defibrillator or automated external defibrillator. In alternative embodiments, for example, in scenarios in which the medical device is a tablet or monitor, the wired connection may be replaced with a wireless connection. While not expressly shown in the figures, the BVM component(s) as well as other treatment and/or sensing devices (e.g., oxygen saturation sensors, accelerometers, air flow sensors) can also be communicatively coupled with the medical device 1402. For example, in embodiments where the BVM incorporates sensors (e.g., oxygen sensor, capnography, flow sensor, air flow module), such sensors can be in communication with the more central medical device 1402. As noted herein, sensors for obtaining data relevant to gas parameters characteristic of the patient airway can be provided as separate components or can be integrated together into a single component.

The electrode assembly 1310 is shown on the patient 1302 in a typical position. The electrode assembly 1310, in this example, is an assembly that combines an electrode positioned high on the right side of the patient's torso, a separate electrode positioned low on the left side of the patient's torso, and a sensor package located over the patient's sternum. The electrode assembly 1310 can further include a sensor package, which, in this example, is obscured in the figure by the hands of rescuer 1304. This sensor package can include a motion sensor (e.g., accelerometer(s), velocity sensor, distance sensor) or similar sensor package that can be used in cooperation with a computer in the medical device 1402 to monitor performance (e.g., compression depth, compression rate, and release) of the chest compressions, patient movement or positioning. Additionally, a microphone can also be included with, or separately from, the electrode assembly 1310 to obtain auscultation data (e.g., acoustic signals) of internal sounds of the patient 1302. The microphone can be used to obtain signals related to heart sounds, breathing sounds or gastric sounds, for example.

In the illustrated example, the medical device 1402 communicates wirelessly with the wrist-worn devices 1320, 1322 to present information and/or guidance to the rescuers 1304, 1306. For example, information related to chest compressions, heart rate, or other relevant information (e.g., SpO2, ETCO2) related to the intubation process can be visually presented on the displays 1321, 1323. Additionally, vibration components and/or audible sound generators on the wrist-worn devices 1320, 1322 can provide feedback. Such feedback can include information about physical status of the patient 1302, guidance and feedback related to ventilation or cardio pulmonary resuscitations of the patient 1302, and/or specific context-sensitive or prioritized instructions to perform critical interventions/tasks to ensure patient safety or optimal therapeutic management. Haptic and audible feedback can have the added benefit of providing a notification to the rescuer while not requiring the rescuer to divert his/her attention from the task at hand. This is as opposed to a visual display, which would typically require the rescuer to turn his/her head to view whatever is presented on the visual display.

In still yet another embodiment, the rescuers may use head-mounted heads-up display systems (not shown). The benefit of wearable heads-up devices is that they allow focus to remain on the patient 1302 while at the same time providing a continuous interface to relevant data.

Figure 13B:
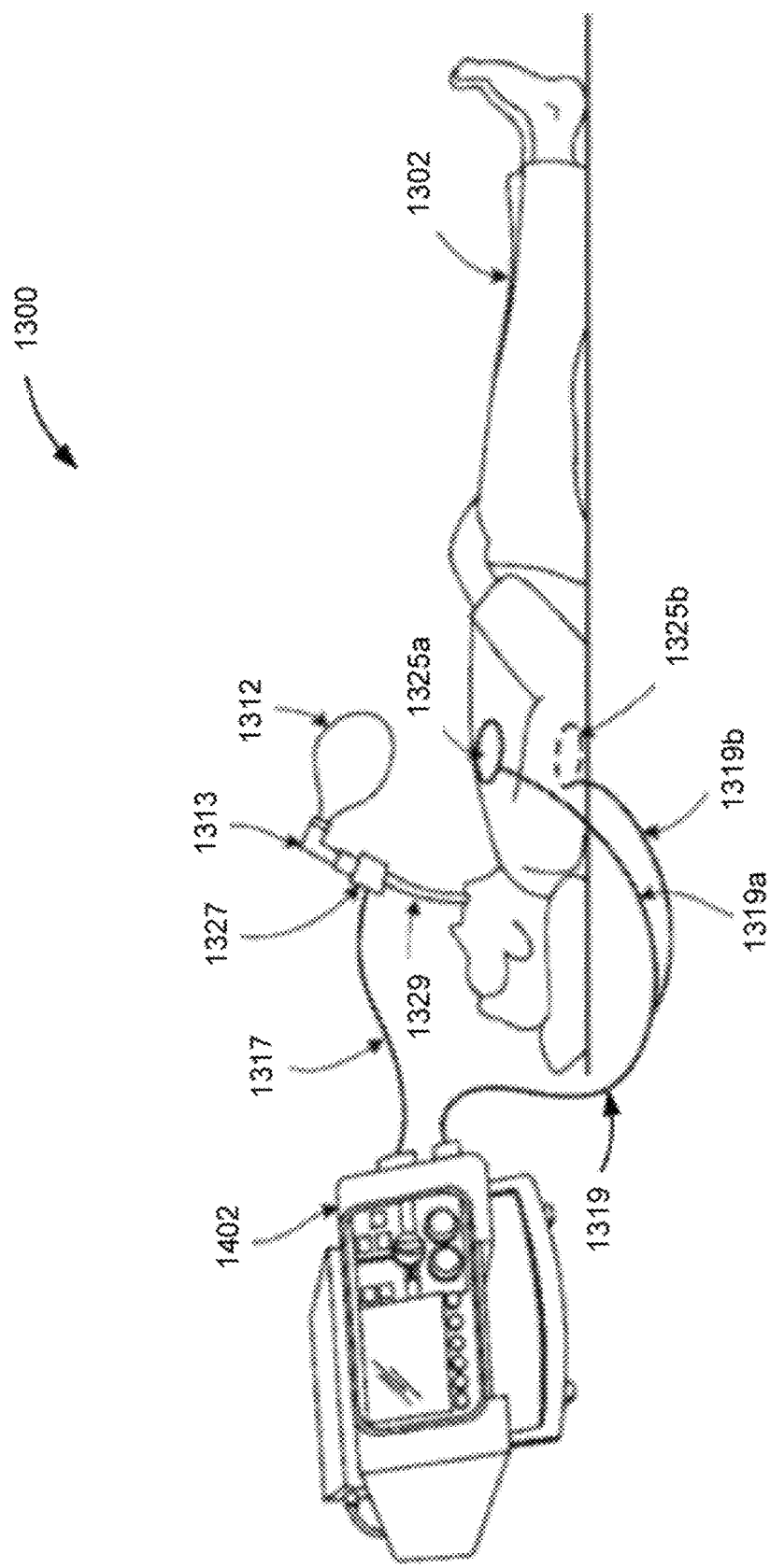
FIG. 13B is an alternate schematic diagram of an example medical system, in accordance with at least one example disclosed herein.

FIG. 13B is a schematic illustration of an example of the airway management system 1300, including the medical device 1402, electrodes, and endotracheal tube 1329 post intubation. That is, during post-intubation, the ET tube has been placed in the trachea of the patient and the patient is being physiologically monitored while ventilations are administered (e.g., by a BVM or ventilator).

In general, a tracheal tube is a catheter that is inserted into the trachea of patient 1302 to establish and maintain an open airway and to ensure adequate exchange of oxygen and carbon dioxide. An endotracheal tube, such as the endotracheal tube 1329, is a specific type of tracheal tube that is usually inserted through the patient's mouth or nose. Many airway tubes such as an endotracheal tube 1329 can be used with embodiments of the present device to provide a patent airway for ventilation and monitoring.

The ventilation bag 1312 is coupled to the ventilation valve 1313. As shown in this example, the mask is no longer required once the endotracheal tube is inserted into the patient. In accordance with embodiments of the present disclosure, one or more airway sensors 1327 (e.g., can include one or more of oxygen sensor, capnography sensor, flow sensor, etc.) can be situated between the ventilation bag 1312 and the endotracheal tube 1329 to allow monitoring of the inspiratory and expiratory gas, for example, as a result of manual ventilation performed using the ventilation bag 1312, and/or monitoring of patient breathing. As is typical, the ventilation bag 1312 and valve 1313 allow the rescuer to actively ventilate the patient 1302 by squeezing the bag or for the patient to spontaneously breathe, while in both instances the patient's exhaled gas exits back through the valve allowing for bidirectional monitoring. Alternatively, the ventilation bag 1312, can be augmented to provide supplemental O2 from a separate O2 source (e.g., oxygen tank).

In the illustrated embodiment, the airway sensor(s) 1327 includes one or more sensors to measure various physiologic and/or airway gas measurement signals during both inspiration and expiration that includes: oxygen (O2), carbon dioxide (CO2), gas flow rate and volume, airway pressure, gas temperature, and gas humidity, to list a few examples. Additionally, processing resources in either the airway sensor(s) 1327 or medical device 1402 are able to calculate additional physiologic and/or airway gas measurement parameters such as breath volume, breathing rate, O2 consumption, CO2 elimination rate, respiratory quotient, airway leak and other calculated values, for instance.

Communication cable 1317 can be any type of communication cable or set of wires, which allows data exchange between the medical device 1402 and the airway sensor(s) 1327 such as but not limited to an RS-232 cable, Universal Serial Bus (USB) cable or Ethernet cable. Communication between the medical device 1402 and the airway sensor(s) 1327 could also be wireless communication such as IEEE 802.11 wireless local area network (WLAN) or low-power radio frequency (RF) communication such as Bluetooth, to list a few examples.

Electrodes 1325a and 1325b are electrically coupled to the medical device 1402 using cables 1319a and 1319b. Electrodes 1325a and 1325b are positioned across the subject's thoracic cavity and attached to the subject, one electrode anterior and the other electrode posterior to the patient, for example. In the embodiment, electrodes 1325a and 1325b are capable of measuring an electrocardiogram (ECG) signal from the patient. The electrodes 1325a and 1325b can also be suitable electrodes for measuring a transthoracic impedance of a subject. In some embodiments, the electrodes 1325a, 1325b can be high-voltage electrodes capable of transmitting electrotherapy to the patient, such as for electrical defibrillation and/or cardiac pacing treatment.

The medical device 1402 is configured with electrodes 1325a and 1325b that are capable of providing therapeutic shocks, if needed, as well as to monitor changes in the transthoracic impedance of the patient 1302. If the endotracheal tube 1329 is properly placed in the subject's trachea and the subject's lungs are ventilated using a ventilation bag 1312 and valve 1313 (or via a mechanical ventilator), then the medical device 1402 detects a change in impedance across the subject's thorax between electrodes 1325a and 1325b. If the endotracheal tube 1329 is not properly placed; for example, it was placed in the subject's esophagus, or has become dislodged, the medical device 1402 will detect that the impedance change across the subject's thorax does not indicate that effective ventilation is being administered and can alert the user with a context-sensitive alarm message using audible and/or visual alarm indicators on the medical device 1402. Alternatively, or in addition, a capnography sensor is provided in the patient airway (e.g., mainstream or sidestream). In this embodiment, if the endotracheal tube 1329 is properly placed in the subject's trachea, then the medical device 1402 detects CO2 (e.g., end tidal CO2 or ETCO2) indicative of proper tube placement; and if the endotracheal tube 1329 is not properly placed or has become dislodged, the medical device 1402 will fail to detect CO2 waveform indicative of proper intubation, and can alert the user with a context-sensitive alarm message using audible and/or visual alarm indicators on the medical device 1402. The medical device 1402 can be in communication with other devices, such as wrist-worn devices 1320, 1322, heads up display devices, for example, for alerting the necessary caregiver(s).

Figure 14:
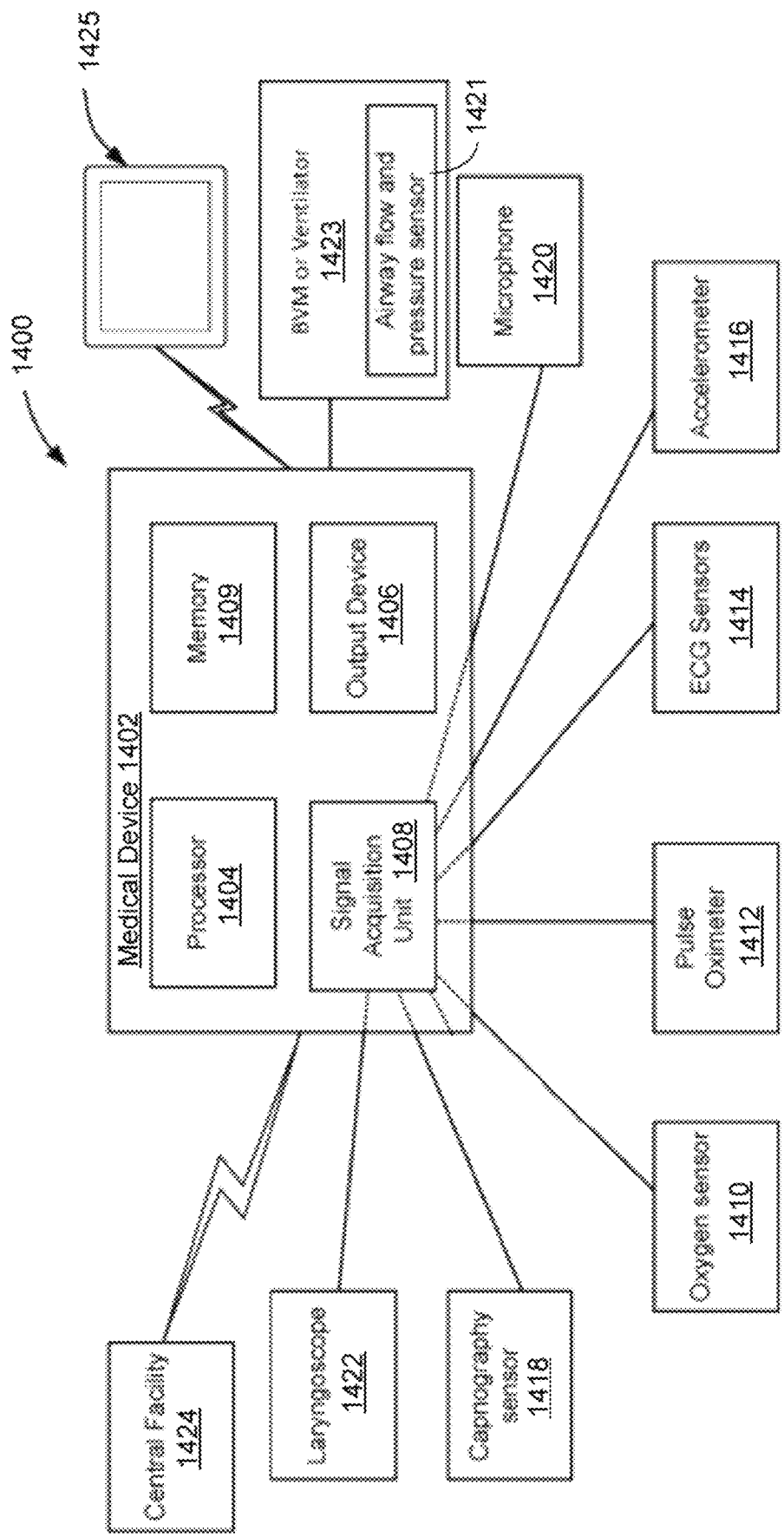
FIG. 14 is a block diagram of an example medical system, in accordance with at least one example disclosed herein.

FIG. 14 is a block diagram of a patient treatment system 1400, including the medical device 1402, airway sensor(s) 1327, device sensors 1410-1422, which measure intubation parameters, peripherals (e.g., ventilator 1423 and portable computing device 1425), and a central facility 1424. The medical device 1402 typically includes a processor 1404 for executing instructions of software running on the medical device 1402, memory 1409 to store the software and sensor information received from the sensors, a signal acquisition unit 1408 to receive sensor information from the sensors 1410-1422, and an output device 1406 to provide feedback to the rescuers, which is typically a display. The output device 1406 can further include one or more speakers for providing audible feedback, or other components for providing other types of feedback, such as haptic/tactile. Generally, a suitable display can be made from a wide variety of materials as described above. Additionally, the screen can be touchscreen display, which is a combined input/output device, which enables user interaction of the medical device 1402 by touching the output device 1406.

Additionally or alternatively, the patient treatment system 1400 can further include a portable computing device 1425 (e.g., tablet, smartphone, laptop computer) in communication with the medical device 1402. In one example, the portable computing device 1425 can mirror the display of the medical device 1402 or can provide a secondary display of information relevant to the user of the portable computing device 1425. For instance, in certain situations, the activities of different users at the emergency scene can differ, hence, it can be preferable for each of the displays (e.g., on the medical device, on the portable computing device, on another device, etc.) to differ according to the job performed by the associated user. Additionally, the portable computing device 1425 can include general information (e.g., dosage charts), medical procedure checklists, and/or other protocols that are typically used during an intubation procedure. Additionally, it can include additional checklists and/or protocols for other medical situations (e.g., instructions on the performance of CPR, or instructions on how to assemble the BVM, how to hook the patient up the ventilator, and other similar instructions). Additionally, the portable computing device would provide a quality assurance report that includes: a list of completed and uncompleted tasks, the time tasks were completed, the required time for each of the tasks, event markers, alarms that occurred, relevant physiologic data as well as other data that demonstrates the performance of the procedure.

Additionally, the portable computing device 1425 can include the ability to allow the user to enter patient information (e.g., height, weight, and gender) via a touchscreen display. The portable computing device can also include internet connectivity (e.g., via Wi-Fi or 3G/4G wireless mobile telecommunication networks) to enable the rescuer to access additional patient information from the central facility, for example.

Respiratory gas monitoring provides a noninvasive method to monitor a range of physiologic or airway gas measurement data that indicates the pattern of ventilation, its effectiveness, the patient's metabolic state, endotracheal tube placement and cardiopulmonary functioning. The present system embodies a multifunction sensor module; however, the medical device 1402 is also capable of providing the performance using a series of individual sensor modules to measure O2 and CO2 gas concentrations, gas flow and airway pressure.

An oxygen sensor 1410 typically measures the amount of oxygen present in the flow of gas through the patient's airway, and can be used to measure gas parameters in accordance with the present disclosure. The oxygen sensor can be equipped to measure the proportion of oxygen in the gas being analyzed. An example of an oxygen sensor that can be incorporated as an airway sensor is the Fibox 4 trace provided by PreSens Precision Sensing from Regensburg, Germany. Accordingly, when the oxygen sensor is placed in the patient airway, a percentage or amount readout of oxygen that is present within the airway can be recorded. In one embodiment, the oxygen sensor is attached to an inner surface of another airway sensor, such as a flow sensor or capnography sensor, or can be located elsewhere along the patient airway. Oxygen is measured contactless through a transparent vessel wall. Preferably, the sensor has a measurement range of oxygen. In an embodiment, an oxygen sensitive coating can be immobilized on a 125 μm flexible transparent polyester foil. In addition, the sensor could also use other oxygen measurement methods such as a galvanic cell or paramagnetic techniques for example.

A pulse oximeter 1412 that provides a measurement of the oxyhemoglobin saturation of the patient can be used to measure physiological parameters in accordance with embodiments described herein. Typically, the pulse oximeter is attached to the patient's finger, but could also be attached to other locations (e.g., finger, palm, toe, sole or ear, for example). In such cases, the sensor is typically placed at a thin part of the patient's body, such as the fingertip or earlobe, and the device passes multiple wavelengths of light through the body to a photodetector on the other side. The changing absorbance at each of the wavelengths can allow for the medical device/sensor to determine the respective absorbance due to pulsing arterial blood. Alternatively, or in addition, a near infrared sensor for measuring muscle oxygenation content and tissue pH could also be implemented to monitor the effective blood flow and tissue oxygenation. Rather than detection through transmission, the reflectance of the multiple wavelengths of light by thicker tissues allow for levels of oxygen at that location to be measured. In the illustrated example, the electrocardiogram sensors 1414 are part of the defibrillator electrodes and measure electrical activity of the patient's heart, although it can be appreciated that ECG leads separate from the defibrillation electrodes can be employed. An accelerometer 1416 or other motion sensor can be employed to measure movements of the patient and/or rescuer, for example, in moving the patient or applying chest compressions to the patient. In alternative embodiments, the motion of the patient could be sensed by a sternal compression sensor, which is part of the electrode assembly 1310 or a separate component entirely. Additionally, the accelerometer could be located on the tube 1329 (e.g., at a proximal location) or the rescuers 1304, 1306.

A flow sensor 1421 for measuring the flow rate and volume of air flowing through the patient's airway can be used to measure gas parameters in accordance with various embodiments. The flow sensor 1421 is typically located within the airway of the patient, in fluid communication with the portable ventilator or BVM 1423. The flow sensor can be in communication with the medical device and, hence, can provide information concerning the flow rate and volume in the patient's airway. Any suitable flow sensor can be employed, such as for example, a differential pressure sensor. The flow sensor can be similar to that described in U.S. Patent Publication 2017/0266399, entitled "Flow Sensor for Ventilation," which is hereby incorporated by reference in its entirety. Accordingly, the flow sensor can provide measurements of inspiratory flow to the patient (e.g., provided by positive pressure breath ventilations) and expiratory flow from the patient (e.g., air breathed out from the patient).

One or more airway sensors 1327 can be employed, for monitoring various characteristics of the air flow within the patient's airway. The airway sensor(s) can include a capnography sensor 1418. For example, the capnography sensor 1418 can be equipped to measure gas parameters, such as the concentration and partial pressure of carbon dioxide (CO2) in the respiratory gases of the subject. Signals/data from the capnography sensor 1418 can be further processed to determine physiological parameters, such as end-tidal CO2 of the patient. In addition, the airway sensor(s) can include a flow sensor that communicates information related to the subject's inspiratory and expiratory gas flow. The airway sensor(s) can further communicate information related to the concentration and partial pressure of respiratory gases, oxygen and water vapor for example. As discussed herein, the airway sensor(s) can include, for example, capnography for measuring CO2, an oxygen sensor for measuring the amount of oxygen, and/or a flow sensor for measuring the rate and volume of flow within the patient's airway, separate or integrated together.

While the illustrated embodiment identifies certain types of sensors, those skilled in the art will recognize that additional sensors could be implemented as well. Likewise, while the specification identifies specific intubation parameters in describing various examples of present system, alternative sensors which perform identical or similar functions can be implemented for enabling the medical device to determine whether steps in an airway management procedure have or have not been completed, for effectively assisting the rescuer in properly carrying out the procedure.

The medical device 1402 can include additional components such as a microphone 1420 to capture acoustic information of the patient 1302 such as the sounds of the patient breathing or sounds of their heart beating. Additionally, or alternatively, the medical device can further include one or more microphones to capture voice commands from the rescuers 1304, 1306.

Furthermore, a video laryngoscope 1422 is also connected to the medical device 1402, which can provide information used as a positioning parameter for the airway management system to determine the current step in the RSI procedure. Laryngoscopes enable rescuers to look at the back of the throat (oropharynx), voice box (larynx) and identify the vocal cords, which provide the critical landmark for insertion of an endotracheal tube into the trachea. Use of a video laryngoscope aids the user in visualizing critical anatomy while also allowing a range of patient-rescuer positions from which to view the airway and insert the endotracheal tube. Additionally, the video laryngoscope provides for a digital recording of the procedure that allows for secondary confirmation of tube placement and post-case review. In an alternative embodiment, the digital recording from the laryngoscope would allow for use of image analysis that could provide additional confirmation that the endotracheal tube was properly placed.

In one embodiment, the medical device 1402 communicates with a central facility 1424. The communication between the central facility 1424 and medical device can be via wireless technologies, like Bluetooth, or wireless telephone networks (e.g., 3G/4G wireless mobile telecommunication networks), or possibly even the Enhanced 911 (or E911) network. The wireless networks are typically secured that require password authentication to access the wireless network. The central facility 1424 can be third-party location that stores and/or analyzes information received from the medical device 1402. The central facility is generally an emergency response center (e.g., 9-1-1 dispatch), back-end component such as a server, hospital, or ambulance, to list a few examples.

Figure 15:
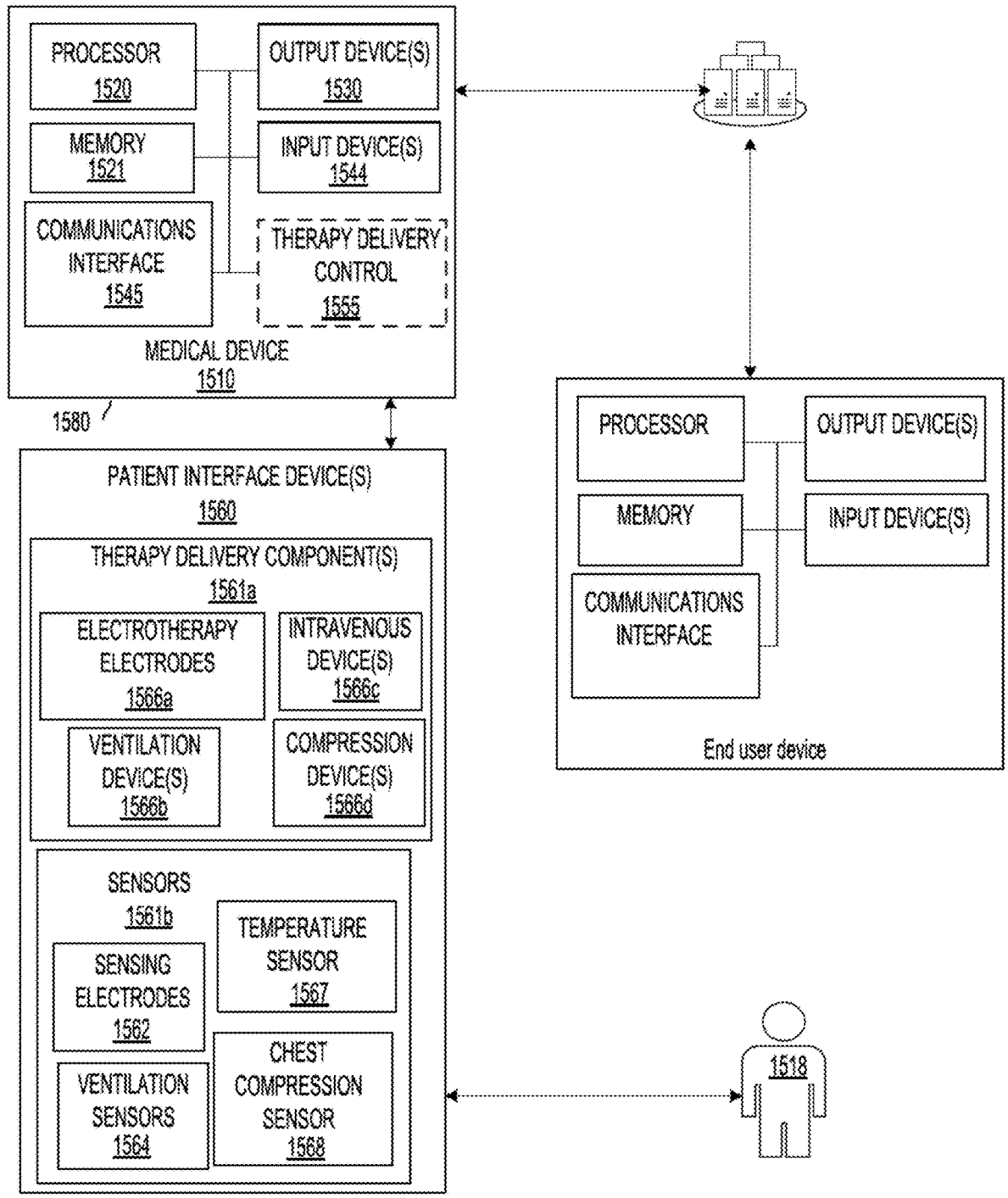
FIG. 15 is a schematic diagram illustrating a medical device in accordance with at least one example disclosed herein.

Referring to FIG. 15, examples of components of a medical device 1510 and are shown schematically. The medical device 1510 can include a processor 1520, a memory 1521, one or more output devices 1530, one or more user input devices 1544, and a communications interface 1545. The communications interface 1545 can include any of a variety of transmitters and/or receivers. For instance, in some examples, the communications interface 1545 includes one or more of an NFC tag, an RFID tag, a barcode and a QR code.

In various implementations, the medical device 1510 can be a defibrillator, patient monitor, defibrillator/monitor, an automated compression device, a therapeutic cooling device, an extracorporeal membrane oxygenation (ECMO) device, a ventilation device, combinations thereof, or another type of medical device configured to couple to one or more therapy delivery components to provide therapy to the patient. In an implementation, the medical device 1510 can be an integrated therapy delivery/monitoring device within a single housing 1580. The single housing 1580 can surround, at least in part, the therapy delivery components and the monitoring components.

The patient interface device(s) 1560 can include one or more therapy delivery component(s) 1561*a* and/or one or more sensor device(s) 1561*b*. The medical device 1510 can be configured to couple to the one or more therapy delivery component(s) 1561*a*. In combination, the medical device 1510 and the one or more therapy delivery components can provide therapeutic treatment to the patient 1518. In an implementation, the medical device 1510 can include or incorporate the therapy delivery component(s) 1561*a*. The therapy delivery component(s) 1561*a* are configured to deliver therapy to the patient and can be configured to couple to the patient. For example, the therapy delivery component(s) 1561*a* can include one or more of electrotherapy electrodes including defibrillation electrodes and/or pacing electrodes, chest compression devices (e.g., one or more belts or a piston), ventilation devices (e.g., a mask and/or tubes), drug delivery devices, etc. The medical device 1510 can include the one or more therapy delivery component(s) 1561*a* and/or can be configured to couple to the one or more therapy delivery component(s) 1561*a* to provide medical therapy to the patient. The therapy delivery component(s) 1561*a* can be configured to couple to the patient 1518. For example, a healthcare provider can attach the electrodes to a patient 1518 and the medical device 1510 (e.g., a defibrillator or defibrillator/patient monitor) can provide electrotherapy to the patient via the defibrillation electrodes. These examples are not limiting of the disclosure as other types of medical devices, therapy delivery components, sensors, and therapy are within the scope of the disclosure.

The first medical device 1510 can be, for example, a therapeutic medical device capable of delivering a medical therapy. For example, the medical therapy can be electrical therapy (e.g. defibrillation, cardiac pacing, synchronized cardioversion, diaphragmatic or phrenic nerve stimulation) and the first medical device 1510 can be a defibrillator, a defibrillator/monitor and/or another medical device configured to provide electrotherapy. As another example, the medical therapy can be chest compression therapy for treatment of cardiac arrest and the first medical device 1510 can be a mechanical chest compression device such as a belt-based chest compression device or a piston-based chest compression device. As other examples, the medical therapy can be ventilation therapy, therapeutic cooling or other temperature management, invasive hemodynamic support therapy (e.g. Extracorporeal Membrane Oxygenation (ECMO)), etc. and the medical device 1510 can be a device configured to provide a respective therapy. In an implementation, the medical device 1510 can be a combination of one or more of these examples. The therapeutic medical device can include patient monitoring capabilities via one or more sensors. These types of medical therapy and devices are examples only and not limiting of the disclosure.

The medical device 1510 can include, incorporate, and/or be configured to couple to the one or more sensor(s) 1561*b* which can be configured to couple to the patient 1518. The sensor(s) 1561*b* are configured to provide signals indicative of sensor data (e.g., first sensor data) to the medical device 1510. The sensor(s) 1561*b* can be configured to couple to the patient. For example, the sensor(s) 1561*b* can include cardiac sensing electrodes, a chest compression sensor, and/or ventilation sensors. The one or more sensors 1561*b* can generate signals indicative of physiological parameters of the patient 1518. For example, the physiological parameters can include one or more of at least one vital sign, an ECG, blood pressure, heart rate, pulse oxygen level, respiration rate, heart sounds, lung sounds, respiration sounds, tidal $CO_2$, saturation of muscle oxygen (SMO2), arterial oxygen saturation (SpO2), cerebral blood flow, electroencephalogram (EEG) signals, brain oxygen level, tissue pH, tissue fluid levels, physical parameters as determined via ultrasound images, parameters determined via near-infrared reflectance spectroscopy, pneumography, and/or cardiography, etc. Additionally or alternatively, the one or more sensors 1561b can generate signals indicative of chest compression parameters, ventilation parameters, drug delivery parameters, fluid delivery parameters, etc.

In addition to delivering therapy to the patient, the therapy delivery component(s) 1561a can include, be coupled to, and/or function as sensors and provide signals indicative of sensor data (e.g., second sensor data) to the medical device 1510. For example, the defibrillation electrodes can be configured as cardiac sensing electrodes as well as electrotherapy delivery devices and can provide signals indicative of transthoracic impedance, electrocardiogram (ECG), heart rate and/or other physiological parameters. As another example, a therapeutic cooling device can be an intravenous cooling device. Such a cooling device can include an intravenous (IV) device as a therapy delivery component configured to deliver cooling therapy and sense the patient's temperature. For example, the IV device can be a catheter that includes saline balloons configured to adjust the patient's temperature via circulation of temperature controlled saline solution. In addition, the catheter can include a temperature probe configured to sense the patient's temperature. As a further example, an IV device can provide therapy via drug delivery and/or fluid management. The IV device can also monitor and/or enable monitoring of a patient via blood sampling and/or venous pressure monitoring (e.g., central venous pressure (CVP) monitoring).

The medical device 1510 can be configured to receive the sensor signals (e.g., from the therapy delivery component(s) 1561a and/or the sensor(s) 1561b) and to process the sensor signals to determine and collect the patient data. The patient data can include patient data which can characterize a status and/or condition of the patient (e.g., physiological data such as ECG, heart rate, respiration rate, temperature, pulse oximetry, non-invasive hemoglobin parameters, capnography, oxygen saturation (SpO2), end tidal carbon dioxide (EtCO2), invasive blood pressure (IBP), non-invasive blood pressures (NIBP), tissue pH, tissue oxygenation, Near Infrared Spectroscopy (NIRS) measurements, etc.). Additionally or alternatively, the patient data can characterize the delivery of therapy (e.g., chest compression data such as compression depth, compression rate, etc.) and/or the patient data can characterize a status and/or condition of the medical equipment used to treat the patient (e.g., device data such as shock time, shock duration, attachment of electrodes, power-on, etc.).

The components of 1520, 1521, 1530, 1544, 1545, and 1555 of the medical device 1510 are communicatively coupled (directly and/or indirectly) to each other for bi-directional communication.

Although shown as separate entities in FIG. 15, the one or more of the components of the device 1510 can be combined into one or more discrete components and/or can be part of the processor 1520. The processor 1520 and the memory 1521 can include and/or be coupled to associated circuitry to perform the functions described herein.

In an implementation, the devices 1510 can be a therapeutic medical device configured to deliver medical therapy to the patient 1518. Thus, the device 1510 can optionally include the therapy delivery control module 1555. For example, the therapy delivery control module 1555 can be an electrotherapy delivery circuit that includes one or more capacitors configured to store electrical energy for a pacing pulse or a defibrillating pulse. The electrotherapy delivery circuit can further include resistors, additional capacitors, relays and/or switches, electrical bridges such as an H-bridge (e.g., including a plurality of insulated gate bipolar transistors or IGBTs), voltage measuring components, and/or current measuring components. As another example, the therapy delivery control module 1555 can be a compression device such as an electro-mechanical controller configured to control a mechanical compression device. As a further example, the therapy delivery control module 1555 can be an electro-mechanical controller configured to control drug delivery, temperature management, ventilation, and/or other type of therapy delivery. Alternatively, some examples of the medical device 1510 cannot be configured to deliver medical therapy to the patient 1518 but can be configured to provide patient monitoring and/or diagnostic care.

The medical device 1510 (e.g., a first medical device) can incorporate and/or be configured to couple to one or more patient interface device(s) 1560. The patient interface device(s) 1560 can include one or more therapy delivery component(s) 1561a and one or more sensor(s) 1561b. The one or more therapy delivery component(s) 1561a and the one or more sensor(s) 1561b sensor can provide one or more signals to the medical device 1510 via wired and/or wireless connection (s).

The one or more therapy delivery components 1561a can include electrotherapy electrodes (e.g., the electrotherapy electrodes 1566a), ventilation device(s) (e.g., the ventilation devices 1566b), intravenous device(s) (e.g., the intravenous devices 1566c), compression device(s) (e.g., the compression devices 1566d), etc. For example, the electrotherapy electrodes can include defibrillation electrodes, pacing electrodes, and/or combinations thereof. The ventilation devices can include a tube, a mask, an abdominal and/or chest compressor (e.g., a belt, a cuirass, etc.), etc. and combinations thereof. The intravenous devices can include drug delivery devices, fluid delivery devices, and combinations thereof. The compression devices can include mechanical compression devices such as abdominal compressors, chest compressors, belts, pistons, and combinations thereof. In various implementation, the therapy delivery component(s) 1561a can be configured to provide sensor data and/or be coupled to and/or incorporate sensors. For example, the electrotherapy electrodes can provide sensor data such as transthoracic impedance, ECG, heart rate, etc. Further the electrotherapy electrodes can include and or be coupled to a chest compression sensor. As another example, the ventilation devices can be coupled to and/or incorporate flow sensors, gas species sensors (e.g., oxygen sensor, carbon dioxide sensor, etc.), etc. As a further example, the intravenous devices can be coupled to and/or incorporate temperature sensors, flow sensors, blood pressure sensors, etc. As yet another example, the compression devices can be coupled to and/or incorporate chest compression sensors, patient position sensors, etc. The therapy delivery control module 1555 can be configured to couple to and control the therapy delivery component(s) 1561a.

In various implementations, the sensor(s) 1561b can include one or more sensor devices configured to provide sensor data that includes, for example, but not limited to electrocardiogram (ECG), blood pressure, heart rate, pulse oxygen level, respiration rate, heart sounds, lung sounds, respiration sounds, tidal CO2, saturation of muscle oxygen (SMO2), arterial oxygen saturation (SpO2), cerebral blood flow, electroencephalogram (EEG) signals, brain oxygen level, tissue pH, tissue fluid levels, images and/or videos via ultrasound, laryngoscopy, and/or other medical imaging techniques, near-infrared reflectance spectroscopy, pneumography, cardiography, and/or patient movement. Images and/or videos can be two-dimensional or three-dimensional.

The sensor(s) 1561b can include sensing electrodes (e.g., the sensing electrodes 1562), ventilation sensors (e.g., the ventilation sensors 1564), temperature sensors (e.g., the temperature sensor 1567), chest compression sensors (e.g., the chest compression sensor 1568), etc. For example, the sensing electrodes can include cardiac sensing electrodes. The cardiac sensing electrodes can be conductive and/or capacitive electrodes configured to measure changes in a patient's electrophysiology, for example to measure the patient's ECG information. In an implementation, the sensing electrodes can be configured to measure the transthoracic impedance and/or a heart rate of the patient 1518. The ventilation sensors can include spirometry sensors, flow sensors, pressure sensors, oxygen and/or carbon dioxide sensors such as, for example, one or more of pulse oximetry sensors, oxygenation sensors (e.g., muscle oxygenation/pH), O2 gas sensors and capnography sensors, and combinations thereof. The temperature sensors can include an infrared thermometer, a contact thermometer, a remote thermometer, a liquid crystal thermometer, a thermocouple, a thermistor, etc. and can measure patient temperature internally and/or externally. The chest compression sensor can include one or more motion sensors including, for example, one or more accelerometers, one or more force sensors, one or more magnetic sensors, one or more velocity sensors, one or more displacement sensors, etc. The chest compression sensor can be, for example, but not limited to, a compression puck, a smart-phone, a hand-held device, a wearable device, etc. The chest compression sensor can be configured to detect chest motion imparted by a rescuer and/or an automated chest compression device (e.g., a belt system, a piston system, etc.). The chest compression sensor can provide signals indicative of chest compression data including displacement data, velocity data, release velocity data, acceleration data, compression rate data, dwell time data, hold time data, blood flow data, blood pressure data, etc. In an implementation, the sensing electrodes and/or the electrotherapy electrodes can include or be configured to couple to the chest compression sensor.

Figure 16:
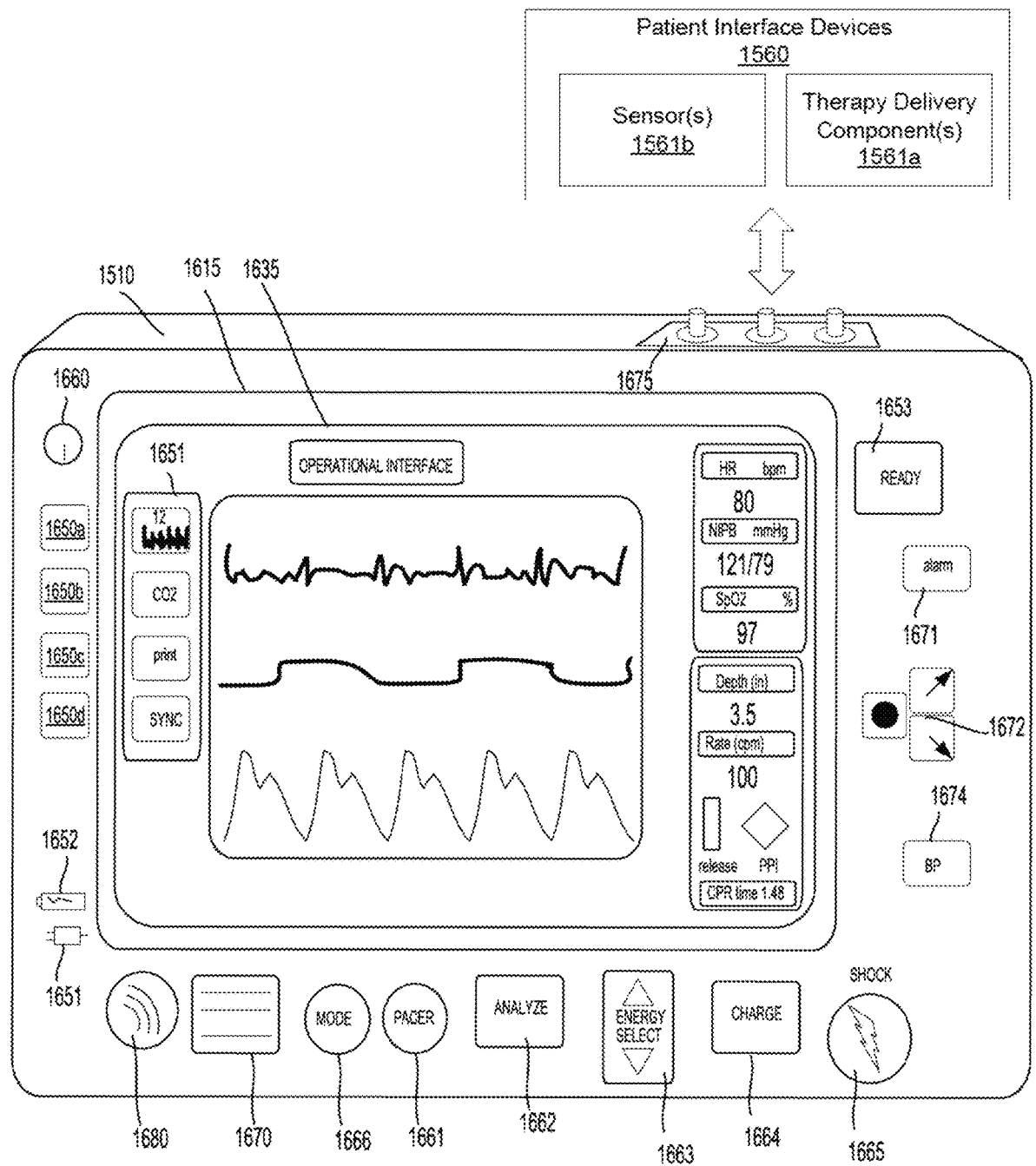
FIG. 16 is a schematic diagram illustrating another medical device in accordance with at least one example disclosed herein.

Referring to FIG. 16, an example of a medical device with an operational interface is shown. The medical device 1510 is shown in FIG. 16 as a patient monitor/defibrillator. This configuration of the medical device 1510 is an example only and not limiting of the disclosure. In various implementations, the medical device 1510 can be a defibrillator, patient monitor, defibrillator/monitor, an automated compression device, a therapeutic cooling device, an extracorporeal membrane oxygenation (ECMO) device, a ventilation device, combinations thereof, or another type of medical device configured to couple to one or more therapy delivery components to provide therapy to the patient. In an implementation, the medical device 1510 can be an integrated therapy delivery/monitoring device that includes a single housing. The single housing can surround, at least in part, the therapy delivery components and the monitoring components. In an implementation, the medical device 1510 can be a modular therapy delivery/monitoring device.

The medical device 1510 can include one or more output or input/output devices, for example, a display screen 1615. A processor of the medical device 1510 can control the display screen 1615 to selectively display the operational interface 1635. The operational interface 1635 as shown in FIG. 16 is an example only and elements can be rearranged, combined, altered, or deleted. As discussed in further detail below, selective display refers to the ability of the processor to select amongst various available display modes which can include an operational interface only display mode.

The operational interface 1635 can provide patient data received by the medical device 1510 from the patient interface device(s) 1560 (e.g., the therapy delivery component(s) 1561*a* and/or from the sensor(s) 1561*b*). For example, the medical device 1510 can be configured to couple to the patient interface device(s) 1560 via the one or more connection ports 1675. The operational interface 1635 can provide the patient data in real-time as the signals are received and processed by the processor 1520 of the medical device 1510.

The therapy delivery component(s) 1561*a* are configured to deliver therapy to the patient and can be configured to couple to the patient. For example, the therapy delivery component(s) 1561*a* can include one or more of electrotherapy electrodes including defibrillation electrodes and/or pacing electrodes, chest compression devices, ventilation devices, drug delivery devices, etc. In addition to delivering therapy to the patient, the therapy delivery component(s) 1561*a* can include, be coupled to, and/or function as sensors and provide signals indicative of sensor data (e.g., first sensor data) to the medical device 1510. For example, the therapy delivery component(s) 1561*a* can be defibrillation and/or pacing electrodes and can provide signals indicative of transthoracic impedance, electrocardiogram (ECG), heart rate and/or other physiological parameters.

The sensor(s) 1561*b* are configured to provide signals indicative of sensor data (e.g., second sensor data) to the medical device 1510. The sensor(s) 1561*b* can be configured to couple to the patient. For example, the sensor(s) 1561*b* can include cardiac sensing electrodes, a chest compression sensor, and/or ventilation sensors.

The medical device 1510 can be configured to receive the sensor signals (e.g., from the therapy delivery component(s) 1561*a* and/or the sensor(s) 1561*b*) indicative of patient data for the patient and configured to process the sensor signals to determine and collect the patient data. The patient data can include patient data which can characterize a status and/or condition of the patient (e.g., physiological data such as ECG, heart rate, pulse oximetry, non-invasive hemoglobin parameters, capnography, oxygen and CO2 concentrations in the airway, invasive and non-invasive blood pressures, tissue pH, tissue oxygenation, near infra-red spectroscopy, etc.). Additionally or alternatively, the patient data can characterize the delivery of therapy (e.g., chest compression data such as compression depth, compression rate, etc.) and/or the patient data can characterize a status and/or condition of the medical equipment used to treat the patient (e.g., device data such as shock time, shock duration, attachment of electrodes, power-on, etc.).

In addition to the display screen 1615, the medical device 1510 can include one or more other output devices such as, for example, a speaker 1670. The processor 1520 can be configured to control the speaker 1670 to provide audible instructions, a metronome (e.g., a chest compression metronome), feedback, and/or physiological information for a user of the medical device 1510. The medical device 1510 can further include device status indicators and/or device operation controls. For example, device status indicators can include a power-on indicator 1651, a battery charge indicator 1652, and/or a device ready indicator 1653. The device operation controls can include a power-on control 1660, a pacer mode control 1661, a heart rhythm analyze control 1662, a defibrillation energy selection control 1663, a charge control 1664, a shock delivery control 1665, a general mode control 1666, an alarm control 1671, one or more display navigation controls 1672, and a sensor control 1674. Activation of the sensor control 1674 can cause an associated patient data sensor to capture patient data and provide the data to the medical device 1510. The display screen 1615 can provide the captured patient data. For example, activation of the sensor control 1674 can cause a blood pressure sensor to measure the patient's blood pressure and can cause the operational interface 1635 to display the measured blood pressure in response to activation of the sensor control 1674. The medical device 1510 can include one or more soft-keys 1650*a*, 1650*b*, 1650*c*, 1650*d*, one or more soft-key labels 1651, and/or an NFC tag 1680. The NFC tag 1680 can enable the medical device 1510 to communicatively couple with another device, such as a mobile computing device or a wireless enabled medical device accessory as described herein.

What is claimed is:

1. A defibrillation electrode for use with a plurality of defibrillation devices, the defibrillation electrode comprising:
   a connector configured to operably couple the defibrillation electrode to at least one of a first defibrillation device and a second defibrillation device;
   a skin contacting portion configured to contact skin of a patient; and
   a housing comprising non-volatile memory and associated circuitry, the non-volatile memory and associated circuitry configured to:
   store a device identifier readable by the first defibrillation device and the second defibrillation device to identify the defibrillation electrode,
   receive medical treatment information from the first defibrillation device via the connector, the medical treatment information comprising at least one of: patient physiological data, patient characteristic data, and rescuer performance data,
   receive timing information of the medical treatment information from the first defibrillation device via the connector, wherein the timing information of the medical treatment information comprises a time at which the medical treatment information was recorded by the first defibrillation device,
   record the medical treatment information, and
   transfer, upon detecting an electrical connection to the second defibrillation device, the medical treatment information to the second defibrillation device.

2. The defibrillation electrode of claim 1, wherein the medical treatment information is recorded by the first defibrillation device during monitoring of the patient prior to and/or during treatment of the patient.

3. The defibrillation electrode of claim 1, wherein the device identifier comprises type and serial information for at least one of the first defibrillation device and the second defibrillation device to record.

4. The defibrillation electrode of claim 1, wherein the device identifier provides for authentication with at least one of the first defibrillation device and the second defibrillation device for secure transfer of the medical treatment information.

5. The defibrillation electrode of claim 1, further comprising timing circuitry operable to independently track time elapsed since the time at which the medical treatment information was recorded by the first defibrillation device.

6. The defibrillation electrode of claim 1, wherein the non-volatile memory and associated circuitry is configured to record the medical treatment information from the first defibrillation device before the transfer of the medical treatment information to the second defibrillation device.

7. The defibrillation electrode of claim 6, wherein the non-volatile memory and associated circuitry is configured to record the medical treatment information from the first defibrillation device when the connector is engaged with the first defibrillation device, and transfer the medical treatment information to the second defibrillation device when the connector is engaged with the second defibrillation device.

8. The defibrillation electrode of claim 1, wherein the medical treatment information further comprises summary information recording critical patient events requiring treatment, shock information for any delivered shocks, pacing summary data, and indications of alarm events.

9. The defibrillation electrode of claim 1, configured to be operably removed from one of the plurality of defibrillation devices and operably coupled to a computing device.

10. The defibrillation electrode of claim 1, wherein the non-volatile memory and associated circuitry are further configured to:
    determine whether the defibrillation electrode is within a proximity of a remote device;
    establish, in response to a determination that the defibrillation electrode is within the proximity, an operable connection with the remote device; and
    transfer at least a portion of the medical treatment information to the remote device.

11. The defibrillation electrode of claim 10, wherein the transfer of at least the portion of the medical treatment information to the remote device occurs automatically when the operable connection is established between the defibrillation electrode and the remote device.

12. The defibrillation electrode of claim 10, wherein the transfer of at least the portion of the medical treatment information to the remote device occurs in response to a user-provided request to transfer subsequent to establishing the operable connection between the defibrillation electrode and the remote device.

13. The defibrillation electrode of claim 1, wherein to record the medical treatment information comprises encrypting the medical treatment information prior to recording.

14. The defibrillation electrode of claim 1, wherein the patient physiological data comprises one or more of patient ECG data, heart rate data, ECG waveform data, end-tidal CO2 data, CO2 waveform data, pulse oximetry data, blood oxygenation data, blood pressure data, and respiratory rate data.

15. The defibrillation electrode of claim 1, wherein the patient characteristic data comprises one or more of patient height data, patient weight data, patient gender indication, patient physical measurement data, and patient history information.

16. The defibrillation electrode of claim 1, wherein the rescuer performance data comprises one or more of chest compression performance data, ventilation performance data, rescuer treatment information, and drug infusion information.

17. The defibrillation electrode of claim 1, wherein the medical treatment information comprises device operational data comprising one or more of defibrillation shock delivery information, defibrillation shock energy information, and ventilator flow information.

18. The defibrillation electrode of claim 1, wherein
    the connector is configured to be operably coupled to the first defibrillation device during a first treatment event and
    at least one of a processor operably coupled to the non-volatile memory and software is further configured to record at least one parameter associated with the first treatment event to the non-volatile memory.

19. The defibrillation electrode of claim 18, wherein the connector is further configured to be decoupled from the first defibrillation device and operably coupled to the second defibrillation device such that the medical treatment information stored on the non-volatile memory is accessible to the second defibrillation device.

20. The defibrillation electrode of claim 1, wherein the non-volatile memory is configured to be operably removed from the defibrillation electrode and operably coupled to a second defibrillation electrode.

21. The defibrillation electrode of claim 1, wherein the non-volatile memory is configured to be operably removed from the defibrillation electrode and operably coupled to a computing device.

22. The defibrillation electrode of claim 1, wherein the non-volatile memory is integrated into the connector.

23. The defibrillation electrode of claim 1, wherein at least a portion of the skin contacting portion is further configured to deliver a defibrillation shock to the patient during treatment.

* * * * *